(12) United States Patent
Bindi et al.

(10) Patent No.: US 10,918,642 B2
(45) Date of Patent: Feb. 16, 2021

(54) N-(SUBSTITUTED-PHENYL)-SULFONAMIDE DERIVATIVES AS KINASE INHIBITORS

(71) Applicant: Nerviano Medical Sciences S.R.L., Nerviano (IT)

(72) Inventors: Simona Bindi, Milan (IT); Davide Carenzi, Travedona Monate (IT); Ilaria Motto, Nerviano (IT); Maurizio Pulici, Caponago (IT)

(73) Assignee: Nerviano Medical Sciences S.R.L., Nerviano (IT)

( * ) Notice: Subject to any disclaimer, the term of this patent is extended or adjusted under 35 U.S.C. 154(b) by 0 days.

(21) Appl. No.: 16/721,267

(22) Filed: Dec. 19, 2019

(65) Prior Publication Data
US 2020/0121686 A1    Apr. 23, 2020

Related U.S. Application Data

(62) Division of application No. 16/312,061, filed as application No. PCT/EP2017/064904 on Jun. 19, 2017, now Pat. No. 10,561,660.

(30) Foreign Application Priority Data

Jun. 21, 2016 (EP) .................................. 16175386

(51) Int. Cl.
| | |
|---|---|
| C07D 487/04 | (2006.01) |
| A61K 31/519 | (2006.01) |
| C07D 513/04 | (2006.01) |
| A61P 37/00 | (2006.01) |
| A61P 25/28 | (2006.01) |
| A61P 35/00 | (2006.01) |
| A61K 31/4355 | (2006.01) |
| A61K 31/4365 | (2006.01) |
| C07D 491/048 | (2006.01) |
| C07D 495/04 | (2006.01) |

(52) U.S. Cl.
CPC ........ *A61K 31/519* (2013.01); *A61K 31/4355* (2013.01); *A61K 31/4365* (2013.01); *A61P 25/28* (2018.01); *A61P 35/00* (2018.01); *A61P 37/00* (2018.01); *C07D 487/04* (2013.01); *C07D 491/048* (2013.01); *C07D 495/04* (2013.01); *C07D 513/04* (2013.01)

(58) Field of Classification Search
CPC ............................ C07D 487/04; A61K 31/519
See application file for complete search history.

(56) References Cited

U.S. PATENT DOCUMENTS

| | | | |
|---|---|---|---|
| 6,001,839 A | 12/1999 | Calderwood et al. | |
| 10,561,660 B2 * | 2/2020 | Bindi | ...................... A61P 25/28 |

FOREIGN PATENT DOCUMENTS

| | | |
|---|---|---|
| WO | 2000017202 A1 | 3/2000 |
| WO | 2015136463 A1 | 9/2015 |

OTHER PUBLICATIONS

Axten J.M., et al., "Discovery of 7-methyl-5-(1-{[3-(trifluoromethyl)phenyl]acetyl}-2,3-dihydro-1H-indol-5-yl)-7H-pyrrolo [2,3-d]pyrimidin-4-amine (GSK2606414), a potent and selective first-in-class Inhibitor of protein kinase (PERK)", Journal of Medicinal Chemistry, vol. 22, No. 16, Aug. 23, 2012, pp. 7193-7207.

Search Report and Written Opinion of PCT/EP2017/064904 dated Aug. 22, 2017.

* cited by examiner

*Primary Examiner* — Golam M Shameem
(74) *Attorney, Agent, or Firm* — Silvia Salvadori, P.C.; Silvia Salvadori

(57) ABSTRACT

The invention relates to N-(substituted-phenyl)-sulfonamide compounds, which are extremely useful as inhibitors of protein kinases (e.g. PERK kinase) and accordingly can be used for the treatment of cell proliferative disorders, such as cancer, or diseases associated with activated unfolded protein response pathways, such as Alzheimer's disease. The present invention also provides methods for preparing these compounds, pharmaceutical compositions comprising these compounds, and methods of treating diseases utilizing pharmaceutical compositions comprising these compounds.

(I)

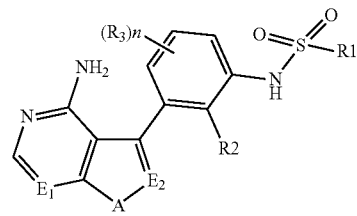

1 Claim, No Drawings
Specification includes a Sequence Listing.

SEQUENCE LISTING

<160> NUMBER OF SEQ ID NOS: 1

<210> SEQ ID NO 1
<211> LENGTH: 15
<212> TYPE: PRT
<213> ORGANISM: Artificial
<220> FEATURE:
<223> OTHER INFORMATION: peptide substrate

<400> SEQUENCE: 1

Leu Leu Ser Glu Leu Ser Arg Arg Arg Ile Arg Ser Ile Asn Lys
1               5                   10                  15

N-(SUBSTITUTED-PHENYL)-SULFONAMIDE DERIVATIVES AS KINASE INHIBITORS

This application is a Divisional Application of U.S. application Ser. No. 16/312,061 filed Dec. 20, 2018, which is a U.S. national stage of PCT/EP2017/064904 filed on 19 Jun. 2017, which claims priority to and the benefit of European Patent Application No. 16175386.8 filed on 21 Jun. 2016, the contents of which are incorporated herein by reference in their entirety.

The invention relates to N-(substituted-phenyl)-sulfonamide compounds, which are extremely useful as inhibitors of protein kinases (e.g. PERK kinase) and accordingly can be used for the treatment of cell proliferative disorders, such as cancer, or diseases associated with activated unfolded protein response pathways, such as Alzheimer's disease. The present invention also provides methods for preparing these compounds, pharmaceutical compositions comprising these compounds, and methods of treating diseases utilizing pharmaceutical compositions comprising these compounds.

The endoplasmic reticulum (ER) represents the main subcellular compartment involved in folding and maturation of proteins destined for organelles and the extracellular space. Several kinds of stresses can alter the function of the ER, including hypoxia, alteration of protein glycosylation, depletion of luminal ER calcium, or changes in ER redox status (Wang M. and Kaufman R. J., Nat Rev Cancer. 2014 (9):581-97). These conditions provoke the accumulation of unfolded or misfolded proteins inside the ER which culminates in the activation of a series of adaptive mechanisms which are referred to as the Unfolded Protein Response (UPR) (Hetz C., Chevet E. and Harding H. P., Nat. Rev. Drug Discov. 2013, 12, 703-719) aimed to restore protein-folding homeostasis. These include an increase in the level of chaperone proteins to favor protein re-folding, degradation of the misfolded proteins, and arrest of translation to reduce the burden of proteins entering the ER. However, if cell damage is sufficiently severe or prolonged, UPR signalling results in cell death by apoptosis (Kim I., Xu W., and Reed J. C., Nat Rev Drug Disc. 2008 (7):1013-1030).

The UPR is typically associated to the maintenance of cellular homeostasis in specialized secretory cells, such as pancreatic β cells, salivary glands and plasma B cells, where the high demand for protein synthesis and secretion requires an efficient and tightly controlled protein homeostasis. However, UPR is involved in many other physiological processes, including lipid and cholesterol metabolism, energy control, inflammation and cell differentiation (Wang M. and Kaufman R. J., Nat Rev Cancer. 2014 (9):581-97). The large number of activities mediated by UPR reflects in the role of ER stress in the progression of diseases such as cancer, neurodegenerative disorders and diabetes.

In mammals, there are three classes of sensors of ER stress (Hetz C., Chevet E. and Harding H. P., Nat. Rev. Drug Discov. 2013, 12, 703-719): inositol-requiring enzyme 1α (IRE1 or ERN1, both α and β isoforms); activating transcription factor 6 (ATF6; both α and β isoforms); and protein kinase RNA-like ER kinase (PERK or EIF2AK3). Dimerization and autophosphorylation of IRE1α implies a conformational change that activates its RNase activity resulting in the excision of a 26-nucleotide intron of the mRNA that encodes the transcription factor X-box binding protein 1 (XBP1). This ultimately leads to the expression of a more stable and active form of this protein, known as XBP1s, which transactivates a subset of target genes involved in protein folding, ER-associated protein degradation (ERAD), protein translocation to the ER, and protein secretion (Chen, Y. and Brandizzi, F. Trends Cell Biol. 2013, 547-555).

ATF6α is a transmembrane protein located in the ER, which upon ER stress, translocates to the Golgi complex where it is processed releasing a cytosolic fragment, ATF6f. This is a transcription factor that regulates the expression of genes of the ERAD pathway (Haze, K., Yoshida, H., Yanagi, H., Yura, T. & Mori, K., Mol. Biol. Cell 1999, 10, 3787-3799).

The activation of PERK, as that of IRE1, involves dimerization, trans-autophosphorylation and the formation of large clusters. Upon activation PERK phosphorylates eukaryotic translation initiator factor 2α (eIF2α), which leads to the inhibition of protein synthesis, thus reducing the number of nascent proteins that enter the ER. This has an important pro-survival effect on the cell per se, but, in addition, it also allows the translation of mRNAs such as that of the activating transcription factor 4 (ATF4), which controls the expression of genes that encode proteins involved in redox processes and amino acid metabolism. ATF4 also regulates the expression of important genes involved in apoptosis, including the transcription factor C/EBP-homologous protein (CHOP) and growth arrest and DNA damage-inducible 34 (GADD34), which participates in a feedback loop to dephosphorylate eIF2α, restoring protein synthesis. (Pytel D., Majsterek I. and Diehl J. A., Oncogene 2015 (35):1207-1215).

Tumor cells are likely to be dependent on active UPR signaling, as during their growth they are often hypoxic and deprived of nutrient due to insufficient blood supply and abnormal blood vessel function (Rzymski T. and Harris A. L., Clin. Cancer Res. 2007, 13(9): 2537-2540). In fact, activation of the UPR has been observed in clinical specimens. Human tumors, including those derived from cervical carcinomas, glioblastomas (Bi M., Naczki C., Koritzinsky M., Fels D., Blais J., Hu N., Harding H., Novoa I., Varia M., Raleigh J., et al., EMBO J. 2005 (24): 3470-81), hepatocellular carcinomas (Nakagawa H., Umemura A., Taniguchi K., Burgada J. F., Dhar D., Ogata H., Zhong Z., Valasek M. A., Seki E., Hidalgo J., Koike K. and Kaufman R. J., Cancer Cell 2014(26): 331-343) and breast cancers (Andruska N., Zheng X., Yang X., Helferich W. G., and Shapiro D. J., Oncogene 2015, 34(29): 3760-3769), show levels of proteins involved in UPR higher than in normal tissues, possibly indicating a stronger dependence of cancer cells on protein homeostasis and functional ER in order to survive.

Besides, aberrant activation of the unfolded protein response is involved in a wide variety of other pathologies, such as ocular diseases, obesity, diabetes (e.g. type 1 diabetes), stroke, myocardial infarction, cardiovascular disease, atherosclerosis, arrhythmias, viral infections, inflammatory diseases, neurodegenerative diseases (such as prion-related diseases, amyotrophic lateral sclerosis, Alzheimer's, Huntington's and Parkinson's disease), and the like. (Wang M. and Kaufman R. J., Nature 2016(529):326-335). Therefore, inhibition of the UPR with small molecules capable of blocking the activity of PERK and other components of the UPR will result in an anticancer effect, as well as in the possibility to treat diseases where there is an activated unfolded protein response.

SUMMARY OF THE INVENTION

Three examples of classes of compounds inhibitors of PERK are represented by the substituted indoline derivatives disclosed in application WO2011/119663 and the substituted pyrrolidinone derivatives disclosed in application WO2015/136463, both in the name of Glaxosmithkline LLC, and the substituted quinazolamine derivatives disclosed in application WO2014/161808 in the name of Janssen Pharmaceutica NV.

Novel classes of pyrrolo[2,3d]pyrimidines and 4-aminopyrrolopyrimidines, useful as serine/threonine or tyrosine kinase inhibitors, are respectively disclosed in WO98/41525 in the name of Knoll AG and WO00/17202 in the name of Basf AG.

Other kinase inhibitors represented by fused ring heteroaryl compounds are described in WO2010/045542 in the name of The Regents of the University of California.

However, there is a strong need for novel compounds which inhibit PERK kinase activity useful for the treatment or prevention of cancer, in particular secretory cancer types, neurodegenerative diseases (such as amyotrophic lateral sclerosis, prion-related diseases, Huntington's, Alzheimer's and Parkinson's disease), and the like, as well as diabetes, obesity, ocular diseases, stroke, myocardial infarction, cardiovascular disease, atherosclerosis, arrhythmias, viral infectious and inflammatory diseases. It is accordingly an object of the present invention to provide such compounds.

DETAILED DESCRIPTION OF THE INVENTION

The present inventors have now discovered that compounds of formula (I), described below, are kinase inhibitors and in particular are inhibitors of PERK, and therefore, are useful in therapy as antitumor agents.

Accordingly, a first object of the present invention is to provide an N-(substituted-phenyl)-sulfonamide represented by formula (I),

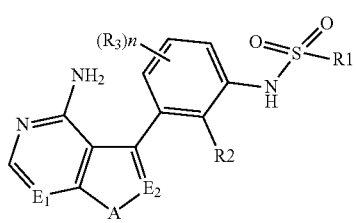

(I)

wherein:

n is 0, 1 or 2;

R1 is an optionally substituted group selected from straight or branched $(C_1-C_8)$ alkyl, $(C_2-C_8)$ alkenyl, $(C_2-C_8)$ alkynyl, $(C_3-C_8)$ cycloalkyl, $(C_3-C_8)$ cycloalkenyl, heterocyclyl, aryl and heteroaryl;

R2 and R3 are independently halogen, cyano, OR4 or an optionally substituted group selected from straight or branched $(C_1-C_8)$ alkyl, $(C_2-C_8)$ alkenyl, $(C_2-C_8)$ alkynyl and $(C_3-C_8)$ cycloalkyl, wherein
  R4 is an optionally substituted group selected from straight or branched $(C_1-C_8)$ alkyl, $(C_2-C_8)$ alkenyl, $(C_2-C_8)$ alkynyl and $(C_3-C_8)$ cycloalkyl;
  $E_1$ and E2 are independently CH or N;
  A is O, S or NR5, wherein
  R5 is hydrogen or an optionally substituted group selected from straight or branched $(C_1-C_8)$ alkyl, $(C_2-C_8)$ alkenyl, $(C_2-C_8)$ alkynyl, $(C_3-C_8)$ cycloalkyl, $(C_3-C_8)$ cycloalkenyl, heterocyclyl, aryl and heteroaryl; and tautomers, hydrates, solvates, N-oxides and pharmaceutically acceptable salts thereof.

The present invention also provides methods of preparing the N-(substituted-phenyl)-sulfonamide compounds represented by formula (I), prepared through a process consisting of standard synthetic transformations.

The present invention also provides a method for treating diseases caused by and/or associated with dysregulated protein kinase activity, particularly protein kinase RNA-like ER kinase (PERK or EIF2AK3) which comprises administering to a mammal, in need thereof, an effective amount of an N-(substituted-phenyl)-sulfonamide compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma, including bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

In addition, the method of the present invention provides tumor angiogenesis and metastasis inhibition as well as the treatment of organ transplant rejection and host versus graft disease.

Another preferred method of the present invention is to treat specific cellular proliferative disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

Another preferred method of the present invention is to treat autoimmune and neurodegenerative diseases, in particular transplant rejection, skin disorders including psoriasis, allergies, asthma, rheumatoid arthritis (RA), multiple sclerosis, systemic lupus erythematosus (SLE), Crohn's disease, prion-related diseases, Alzheimer's disease, degenerative nerve diseases, encephalitis, stroke, Parkinson's disease, amyotrophic lateral sclerosis, Huntington's disease and Pick's disease.

Another preferred method of the present invention is to treat Alzheimer's disease, which comprises administering to a subject in need thereof an effective amount of a compound of Formula (I).

Another preferred method of the present invention is to treat stroke, which comprises administering to a subject in need thereof an effective amount of a compound of Formula (I).

Another preferred method of the present invention is to treat Type 1 diabetes, which comprises administering to a subject in need thereof an effective amount of a compound of Formula (I).

Another preferred method of the present invention is to treat a disease state selected from: myocardial infarction, cardiovascular disease, atherosclerosis, arrhythmias, obesity, ocular diseases and inflammatory diseases, which comprises administering to a subject in need thereof an effective amount of a compound of Formula (I).

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising one or more compounds of formula (I) or a pharmaceutically acceptable salt thereof, as defined above, and at least one pharmaceutically acceptable excipient, carrier or diluent.

The present invention further provides a pharmaceutical composition comprising a compound of formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, cdks inhibitors, tubulin binding agents, topoisomerase I inhibitors, topoisomerase II inhibitors, and the like.

Moreover the invention provides an in vitro method for inhibiting the protein kinase RNA-like ER kinase (PERK or EIF2AK3) activity which comprises contacting the said protein with an effective amount of a compound of formula (I) as defined above.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

As such, unless otherwise provided, when in compounds of formula (I) $E_2$ is nitrogen, A is NR5 and R5 is hydrogen, only one of the following tautomeric forms of formula (Ia) or (Ib) is indicated, the remaining one has still to be intended as comprised within the scope of the invention:

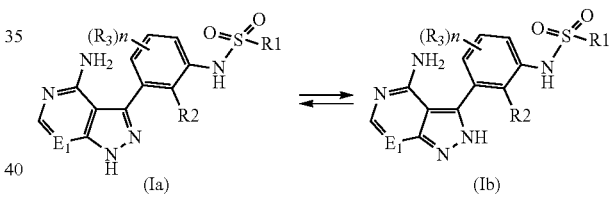

In cases wherein compounds may exist in other tautomeric forms, such as keto-enol tautomers, each tautomeric form is contemplated as being included within this invention whether existing in equilibrium or predominantly in one form.

With the term "straight or branched ($C_1$-$C_8$) alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "($C_3$-$C_8$) cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like. The heterocyclyl ring can be optionally further fused or linked to aromatic and non-aromatic carbocyclic and heterocyclic rings.

With the term "$(C_2-C_8)$ alkenyl" we intend an aliphatic $(C_2-C_8)$ hydrocarbon chain containing at least one carbon-carbon double dond and which can be straight or branched. Representative examples include, but are not limited to, ethenyl, 1-propenyl, 2-propenyl, 1- or 2-butenyl, and the like.

With the term "$(C_2-C_8)$ alkynyl" we intend an aliphatic $(C_2-C_8)$ hydrocarbon chain containing at least one carbon-carbon triple dond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated 7-electron bond system. Non limiting examples of such aryl groups are phenyl, α- or β-naphthyl or biphenyl groups.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

According to the present invention and unless otherwise provided, any of the above R1, R2, R3, R4 and R5 group may be optionally substituted, in any of their free positions, by one or more groups, for instance 1 to 6 groups, independently selected from: halogen, nitro, oxo groups (=O), cyano, $(C_1-C_8)$ alkyl, polyfluorinated $(C_1-C_8)$ alkyl, polyfluorinated $(C_1-C_8)$ alkoxy, $(C_2-C_8)$ alkenyl, $(C_2-C_8)$ alkynyl, hydroxyalkyl, aryl, arylalkyl, heteroaryl, heteroarylalkyl, heterocyclyl, heterocyclylalkyl, $(C_3-C_8)$ cycloalkyl, hydroxy, $(C_1-C_8)$ alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term halogen atom we intend a fluorine, chlorine, bromine or iodine atom.

With the term cyano we intend a —CN residue.

With the term nitro we intend a —NO$_2$ group.

With the term polyfluorinated alkyl or polyfluorinated alkoxy we intend any of the above straight or branched $(C_1-C_8)$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $(C_1-C_8)$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines.

Preferably, object of the present invention are compounds of formula (I) wherein n is 0 or 1; R1 is an optionally substituted group selected from $(C_3-C_8)$ cycloalkyl, aryl and heteroaryl; R2 is halogen or $(C_1-C_8)$ alkyl; A is S or NR5 and R3, R4, $E_1$, $E_2$ and R5 are as defined above. More preferably, object of the present invention are compounds of formula (I) wherein n is 0; R1 is an optionally substituted aryl or heteroaryl; R2 is halogen; A is NR5 and R3, R4, $E_1$, $E_2$ and R5 are as defined above.

Even more preferably, object of the present invention are compounds of formula (I) wherein n is 0; R1 is an optionally substituted aryl; R2 is halogen; $E_1$ is N; $E_2$ is CH; A is NR5, wherein R5 is an optionally substituted group selected from straight or branched $(C_1-C_8)$ alkyl and $(C_3-C_8)$ cycloalkyl; and R3 and R4 are as defined above.

Specific, not limiting, preferred compounds (cmpds.) of the invention, whenever appropriate in the form of pharmaceutically acceptable salts, are the following:
1) N-[3-(4-Amino-7-methyl-7H-pyrrolo[2,3-d]pyrimidin-5-yl)-2-fluoro-phenyl]-3-chloro-4-methoxy-benzenesulfonamide (cmpd 1);
2) N-[3-(4-Amino-7-isopropyl-7H-pyrrolo[2,3-d]pyrimidin-5-yl)-2-fluoro-phenyl]-3-chloro-4-methoxy-benzenesulfonamide (cmpd 2);
3) N-[3-(4-Amino-7-(1-methyl-piperidin-4-yl)-7H-pyrrolo[2,3-d]pyrimidin-5-yl]-2-fluoro-phenyl)-5-chloro-2-fluoro-4-methoxy-benzenesulfonamide (cmpd 3);

4) N-[3-(4-Amino-7-(1-methyl-piperidin-4-yl)-7H-pyrrolo[2,3-d]pyrimidin-5-yl]-2-fluoro-phenyl)-3-chloro-4-methoxy-benzenesulfonamide (cmpd 4);

5) N-[3-(4-Amino-7-(1-cyclopropyl-piperidin-4-yl)-7H-pyrrolo[2,3-d]pyrimidin-5-yl]-2-fluoro-phenyl)-3-chloro-4-methoxy-benzenesulfonamide (cmpd 5);

6) N-[3-(4-Amino-7-(1-isopropyl-piperidin-4-yl)-7H-pyrrolo[2,3-d]pyrimidin-5-yl]-2-fluoro-phenyl)-3-chloro-4-methoxy-benzenesulfonamide (cmpd 6);

7) N-[3-(4-Amino-1-methyl-1H-pyrazolo[3,4-d]pyrimidin-3-yl)-2-fluoro-phenyl]-5-chloro-2-fluoro-4-methoxy-benzenesulfonamide (cmpd 9);

8) N-[3-(4-Amino-7-methyl-7H-pyrrolo[2,3-d]pyrimidin-5-yl)-2-fluoro-phenyl]-4-methoxy-3-methyl-benzenesulfonamide (cmpd 12);

9) N-[3-(4-Amino-7-methyl-7H-pyrrolo[2,3-d]pyrimidin-5-yl)-2-fluoro-phenyl]-3-chloro-benzenesulfonamide (cmpd 13);

10) N-[3-(4-Amino-7-methyl-7H-pyrrolo[2,3-d]pyrimidin-5-yl)-2-fluoro-phenyl]-4-bromo-2-fluoro-benzenesulfonamide (cmpd 22);

11) N-[3-(4-Amino-7-methyl-7H-pyrrolo[2,3-d]pyrimidin-5-yl)-2-fluoro-phenyl]-5-chloro-2-fluoro-4-methoxy-benzenesulfonamide (cmpd 24);

12) N-[3-(4-Amino-7-methyl-7H-pyrrolo[2,3-d]pyrimidin-5-yl)-2-fluoro-phenyl]-3,4-dichloro-benzenesulfonamide (cmpd 25);

13) N-[3-(4-Amino-7-methyl-7H-pyrrolo[2,3-d]pyrimidin-5-yl)-2-fluoro-phenyl]-3,5-dichloro-benzenesulfonamide (cmpd 26);

14) N-[3-(4-Amino-7-methyl-7H-pyrrolo[2,3-d]pyrimidin-5-yl)-2-fluoro-phenyl]-4-methoxy-3,5-dimethyl-benzenesulfonamide (cmpd 29);

15) N-[3-(4-Amino-7-methyl-7H-pyrrolo[2,3-d]pyrimidin-5-yl)-2-fluoro-phenyl]-3,4,5-trifluoro-benzenesulfonamide (cmpd 32);

16) 5-Bromo-6-chloro-pyridine-3-sulfonic acid [3-(4-amino-7-methyl-7H-pyrrolo[2,3-d]pyrimidin-5-yl)-2-fluoro-phenyl]-amide (cmpd 33);

17) N-[3-(4-Amino-1-methyl-1H-pyrazolo[3,4-d]pyrimidin-3-yl)-2-fluoro-phenyl]-4-methoxy-3-methyl-benzenesulfonamide (cmpd 34);

18) N-[3-(4-Amino-1-methyl-1H-pyrazolo[3,4-d]pyrimidin-3-yl)-2-fluoro-phenyl]-3-chloro-4-methoxy-benzenesulfonamide (cmpd 35);

19) N-{3-[4-Amino-7-(tetrahydro-pyran-4-yl)-7H-pyrrolo[2,3-d]pyrimidin-5-yl]-2-fluoro-phenyl}-4-methoxy-3-methyl-benzenesulfonamide (cmpd 36);

20) N-{3-[4-Amino-7-(tetrahydro-pyran-4-yl)-7H-pyrrolo[2,3-d]pyrimidin-5-yl]-2-fluoro-phenyl}-3-chloro-4-methoxy-benzenesulfonamide (cmpd 37);

21) N-{3-[4-Amino-7-(1-methyl-piperidin-4-yl)-7H-pyrrolo[2,3-d]pyrimidin-5-yl]-2-fluoro-phenyl}-4-methoxy-3-methyl-benzenesulfonamide (cmpd 38);

22) N-{3-[4-Amino-7-(1-cyclopropyl-piperidin-4-yl)-7H-pyrrolo[2,3-d]pyrimidin-5-yl]-2-fluoro-phenyl}-4-methoxy-3-methyl-benzenesulfonamide (cmpd 39);

23) N-{3-[4-Amino-7-(1-isopropyl-piperidin-4-yl)-7H-pyrrolo[2,3-d]pyrimidin-5-yl]-2-fluoro-phenyl}-4-methoxy-3-methyl-benzenesulfonamide (cmpd 40);

24) N-{3-[4-Amino-7-(1-ethyl-piperidin-4-yl)-7H-pyrrolo[2,3-d]pyrimidin-5-yl]-2-fluoro-phenyl}-4-methoxy-3-methyl-benzenesulfonamide (cmpd 41);

25) N-[3-(4-Amino-7-methyl-7H-pyrrolo[2,3-d]pyrimidin-5-yl)-2-fluoro-phenyl]-2-fluoro-4-methoxy-5-methyl-benzenesulfonamide (cmpd 44);

26) N-[3-(4-Amino-7-methyl-7H-pyrrolo[2,3-d]pyrimidin-5-yl)-2-fluoro-phenyl]-4-bromo-2,5-difluoro-benzenesulfonamide (cmpd 46);

27) 5-Chloro-thiophene-2-sulfonic acid [3-(4-amino-7-methyl-7H-pyrrolo[2,3-d]pyrimidin-5-yl)-2-fluoro-phenyl]-amide (cmpd 47);

28) 5-Bromo-thiophene-2-sulfonic acid [3-(4-amino-7-methyl-7H-pyrrolo[2,3-d]pyrimidin-5-yl)-2-fluoro-phenyl]-amide (cmpd 48);

29) N-[3-(4-Amino-7-methyl-7H-pyrrolo[2,3-d]pyrimidin-5-yl)-2-fluoro-phenyl]-4-bromo-3-methyl-benzenesulfonamide (cmpd 52);

30) N-{3-[4-Amino-1-(1-methyl-piperidin-4-yl)-1H-pyrazolo[3,4-d]pyrimidin-3-yl]-2-fluoro-phenyl}-5-chloro-2-fluoro-4-methoxy-benzenesulfonamide (cmpd 61);

31) N-[3-(4-Amino-1-piperidin-4-yl-1H-pyrazolo[3,4-d]pyrimidin-3-yl)-2-fluoro-phenyl]-5-chloro-2-fluoro-4-methoxy-benzenesulfonamide (cmpd 62);

32) N-[3-(4-Amino-1-piperidin-4-yl-1H-pyrazolo[3,4-d]pyrimidin-3-yl)-2-fluoro-phenyl]-3-chloro-4-methoxy-benzenesulfonamide (cmpd 63);

33) N-[3-(4-Amino-7-piperidin-4-yl-7H-pyrrolo[2,3-d]pyrimidin-5-yl)-2-fluoro-phenyl]-4-methoxy-3-methyl-benzenesulfonamide (cmpd 64);

34) N-{3-[4-Amino-7-(1-methyl-piperidin-4-yl)-7H-pyrrolo[2,3-d]pyrimidin-5-yl]-2-fluoro-phenyl}-3,4-dichloro-benzenesulfonamide (cmpd 71);

35) N-{3-[4-Amino-7-(1-methyl-piperidin-4-yl)-7H-pyrrolo[2,3-d]pyrimidin-5-yl]-2-fluoro-phenyl}-4-bromo-2-fluoro-benzenesulfonamide (cmpd 72);

36) N-{3-[4-Amino-7-(1-methyl-piperidin-4-yl)-7H-pyrrolo[2,3-d]pyrimidin-5-yl]-2-fluoro-phenyl}-2-fluoro-4-methoxy-5-methyl-benzenesulfonamide (cmpd 73);

37) 6-Methoxy-pyridine-3-sulfonic acid [3-(4-amino-7-methyl-7H-pyrrolo[2,3-d]pyrimidin-5-yl)-2-fluoro-phenyl]-amide (cmpd 81);

38) N-[3-(4-Amino-7-methyl-7H-pyrrolo[2,3-d]pyrimidin-5-yl)-2-fluoro-phenyl]-4-chloro-2-fluoro-benzenesulfonamide (cmpd 85) and 39) N-[3-(4-Amino-7-methyl-7H-pyrrolo[2,3-d]pyrimidin-5-yl)-2-fluoro-phenyl]-3-bromo-4-methoxy-benzenesulfonamide (cmpd 87).

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis on non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

In one general synthetic process, compounds of formula (I) as defined above can be prepared according to the following Scheme 1:
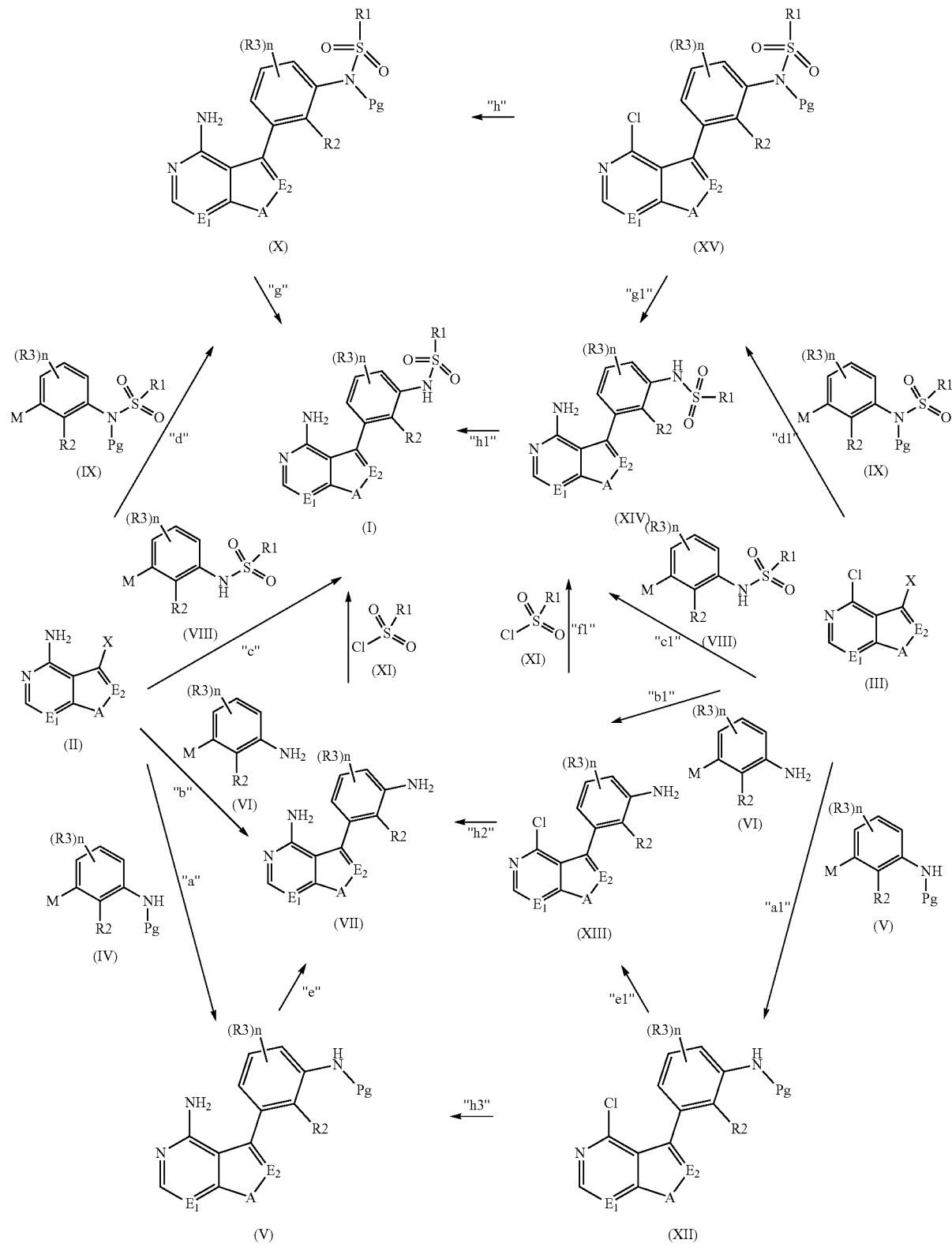
Scheme 1

In the above scheme 1 A, $E_1$, $E_2$, R1, R2, R3 and n are as defined above; X is a halogen atom, such as iodine or bromine, or a suitable leaving group, such as triflate; M is a suitable organometal group, such as $B(OH)_2$, $B(OAlk)_2$, $Sn(Alk)_3$, $Al(Alk)_2$, ZnX, MgX or $ZrCp_2X$, wherein X is halogen and Alk is a ($C_1$-$C_8$) alkyl, and Pg is a suitable nitrogen protecting group, such as tertbutoxy carbonyl, benzyl, benzyloxycarbonyl, methoxymethyl or the like.

In a synthetic process for the preparation of a compound of formula (I), which is described in scheme 1, in step "a" a compound of formula (II) is reacted with a compound of formula (IV) exploiting any of the cross-coupling reactions suitable for the formation of carbon-carbon bonds. Said reactions, which are well known in the art, imply coupling with a suitable organometal reagent, such as, for instance, an organoboron, organotin, organozinc, organoaluminum or organozirconium compound and the like. In step "b" the same kind of reaction may be performed to couple a compound of formula (II) with a compound of formula (VI) to yield a compound of formula (VII). In step "c" the same kind of reaction may be performed to couple a compound of formula (II) with a compound of formula (VIII) to yield a compound of formula (I). In step "d" the same kind of reaction may be performed to couple a compound of formula (II) with a compound of formula (IX) to yield a compound of formula (X). In step "e" a compound of formula (V) undergoes selective removal of the group Pg to give a compound of formula (VII), which, in step "f", is reacted with a sulfonyl chloride derivative of formula (XI) to yield a compound of formula (I). In step "g" selective removal of the protecting group from a compound of formula (X) yields a compound of formula (I).

In step "a1" a compound of formula (III) is reacted with a compound of formula (IV) exploiting any of the cross-coupling reactions suitable for the formation of carbon-carbon bonds as reported above for step "a" to form a compound of formula (XII). In step "b1" the same kind of reaction may be performed to couple a compound of formula (III) with a compound of formula (VI) to yield a compound of formula (XIII). In step "c1" the same kind of reaction may be performed to couple a compound of formula (III) with a compound of formula (VIII) to yield a compound of formula (XIV). In step "d1" the same kind of reaction may be performed to couple a compound of formula (III) with a compound of formula (IX) to yield a compound of formula (XV). In step "e1" a compound of formula (XII) undergoes selective removal of the group Pg to give a compound of formula (XIII), which, in step "f1", is reacted with a sulfonyl chloride derivative of formula (XI) to yield a compound of formula (XIV). In step "g1" selective removal of the protecting group from a compound of formula (XV) yields a compound of formula (XIV).

In step "h" the reaction of a compound of formula (XV) with ammonia or an ammonia equivalent, such as ammonium acetate, affords a compound of general formula (X). In step "h1" the same kind of reaction performed on a compound of formula (XIV) yields a compound of formula (I). In step "h2" the same kind of reaction performed on a compound of formula (XIII) yields a compound of formula (VII). In step "h3" the same kind of reaction performed on a compound of formula (XII) yields a compound of formula (V).

According to step "a" of scheme 1, a compound of formula (II) is reacted with a suitable organometal derivative of formula (IV), such as, for instance, an organoboron compound (Suzuki reaction), an organotin compound (Stille reaction), an organozinc, organoalluminium or organozirconium compound (Negishi reaction), and the like. Said reactions are well known among those with ordinary skills in the art. Preferred reaction is the Suzuki reaction where an appropriate aryl or heteroaryl boronate ester or acid is used in the presence of a palladium or nickel-based catalyst, such as, for instance, palladium(tetrakistriphenyl)phosphine, and a suitable base, such as $Cs_2CO_3$, $K_2CO_3$, $Rb_2CO_3$, NaOH, CsF, and the like. Said reactions can be carried out in a solvent such as N,N-dimethylformamide, dimethylsulfoxide, water, dimethoxyethane, 1,4-dioxane, tetrahydrofuran or the like, and mixtures thereof, in a microwaves apparatus or in the classical thermal conditions, at a temperature ranging from 90 to 120° C. and for a time ranging from 30 minutes to about 24 hours.

According to steps "b", "c" and "d" of scheme 1, a compound of formula (II) is transformed into a compound respectively of formula (VII), (I) and (X) as defined above, by means of a cross-coupling reaction with a derivative respectively of formula (VI), (VIII) and (IX) as defined above according to step "a" of scheme 1.

According to step "e" or "g" of scheme 1, the selective removal of the Pg group, respectively from a compound of formula (V) to afford a compound of formula (VII) or from a compound of formula (X) to afford a compound of formula (I), can be accomplished using acidic or reductive conditions. For instance, the reaction is carried out using strong acids, such as trifluoroacetic acid, optionally in the presence of suitable co-solvent, such as dichloromethane, at temperatures ranging from 20° C. to reflux and for a time ranging from 30 minutes to about 48 hours. Alternatively, when Pg is a benzyl or a benzyloxy group, said reaction is carried out using reductive conditions, such $H_2$ in the presence of a suitable hydrogenation catalyst. The hydrogenation catalyst is usually a metal, most often palladium, which can be used as such or supported on carbon, in a suitable solvent such as, for instance, tetrahydrofuran, 1,4-dioxane, N,N-dimethylformamide, methanol, ethyl acetate, or a mixture thereof.

According to step "f" of scheme 1, a compound of formula (VII) is reacted with a sulfonyl chloride of formula (XI) to afford a compound of formula (I). Such a reaction is carried out in the presence of a suitable base, such as for instance pyridine, N-methyl morpholine or diisopropyl ethylamine, in the appropriate solvent such as pyridine, dichloromethane or tetrahydrofuran, at a temperature ranging from 0° C. to reflux and for a time varying from about 1 hour to about 7 days.

According to steps "a1", "b1", "c1" and "d1" of scheme 1, the conversion of a compound of formula (III) into a compound respectively of formula (XII), (XIII), (XIV) and (XV) is accomplished as described under step "a" of scheme 1.

According to steps "e1" and "g1" of scheme 1, the conversion of a compound of formula (XII) and (XV) respectively into a compound formula (XIII) and (XIV) is accomplished as described under step "e" of scheme 1.

According to step "f1" of scheme 1, the conversion of a compound of formula (XIII) into a compound of formula (XIV) is accomplished as described under step "f" of scheme 1.

According to step "h" of scheme 1, a compound of formula (XV) is transformed into a compound of formula (X) using a solution of ammonia in a suitable solvent, such as tetrahydrofuran, 1,4-dioxane, pyridine, methanol, ethanol and the like, or ammonium salts, such as for instance ammonium acetate or ammonium hydrochloride in solvents such as water, N,N-dimethylformamide, N,N-dimethylacetamide, N-methyl pyrrolidone, dimethylsulfoxide and the like and mixture thereof, at temperatures ranging from 20° C. to reflux in the classical thermal conditions or using a microwaves apparatus for a time ranging from 30 minutes to about 24 hours.

According to steps "h1", "h2" and "h3" of scheme 1, a compound of formula (XIV), (XIII) and (XII) is converted respectively into a compound of formula (I), (VII) and (V) as described under step "h" of scheme 1.

Preferably, compounds of formula (I) or pharmaceutically acceptable salts thereof, as defined above, can be prepared according to the process defined above, comprising the step of cross-coupling of an intermediate of formula (II)

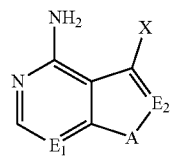
(II)

wherein $E_1$, $E_2$, A are as defined in claim 1 and X is halogen or a leaving group, alternatively with the following compounds:

Step a) a derivative of formula (IV)

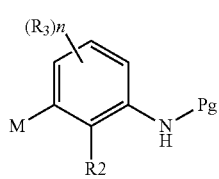
(IV)

wherein R2, R3 and n are as defined above, M is an organometal group and Pg is a nitrogen protecting group; followed by Step e) selective removing of the Pg group from the resultant intermediate of formula (V)

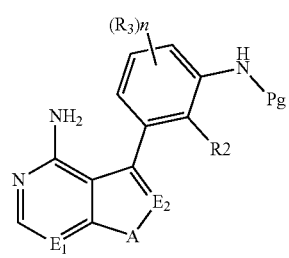
(V)

wherein $E_1$, $E_2$, A, R2, R3, n and Pg are as defined above; and

Step f) reacting the resultant intermediate of formula (VII)

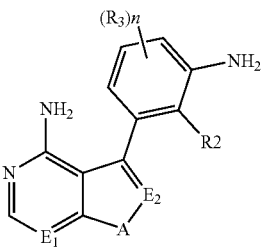
(VII)

wherein $E_1$, $E_2$, A, R2, R3 and n are as defined above, with a derivative of formula (XI)

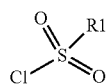
(XI)

wherein R1 is as defined above, to obtain a compound of formula (I) as defined above;

OR:

Step b) a derivative of formula (VI)

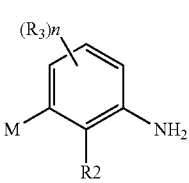
(VI)

wherein R2, R3, n and M are as defined above; followed by

Step f) reacting the resultant intermediate of formula (VII), as defined above, with a derivative of formula (XI), as defined above, to obtain a compound of formula (I) as defined above;
OR:
Step c) a derivative of formula (VIII)

(VIII)

wherein R1, R2, R3, n and M are as defined above;
OR:
Step d) a derivative of formula (IX)

(IX)

wherein R1, R2, R3, n, Pg and M are as defined above;
followed by:
Step g) selective removing of the Pg group from the resultant intermediate of formula (X)

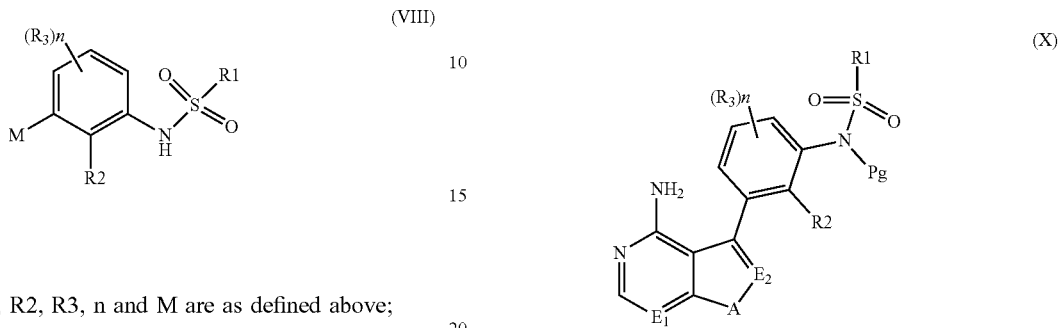

wherein $E_1$, $E_2$, A, R1, R2, R3, n and Pg are as defined above, to obtain a compound of formula (I) as defined above;

optionally converting a compound of formula (I) into another compound of formula (I), and, if desired, converting a compound of formula (I) into a pharmaceutically acceptable salt thereof or converting a salt into the free compound (I).

Alternatively, a compound of formula (I) as defined above can be prepared according to the following Scheme 2:

Scheme 2

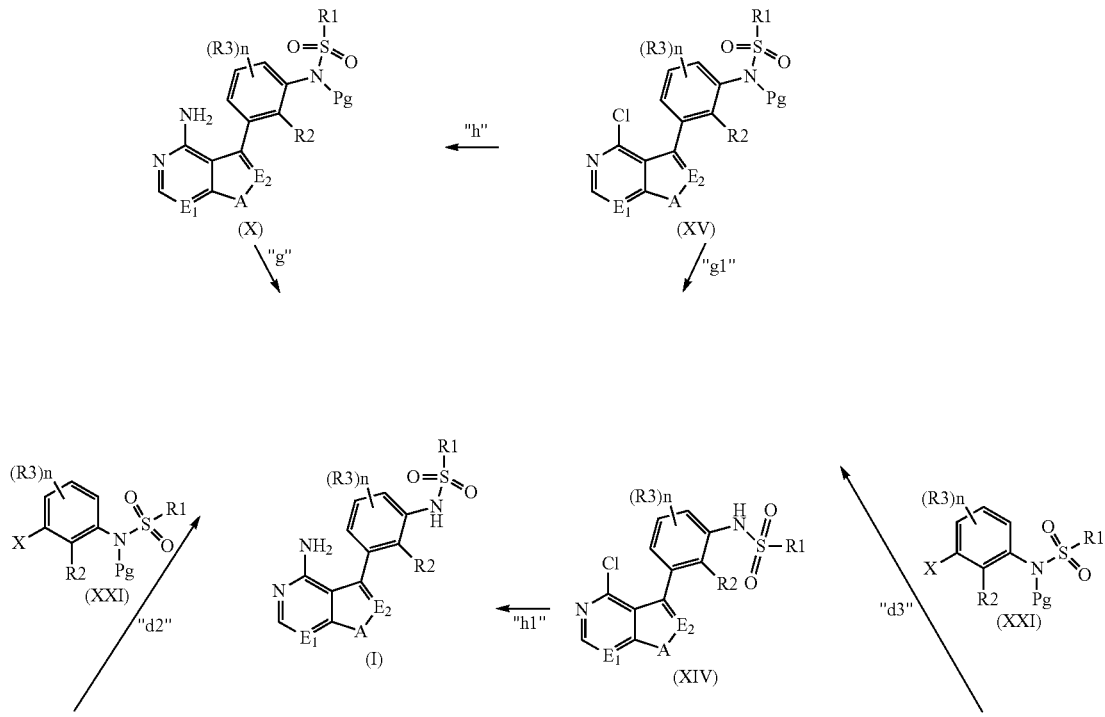

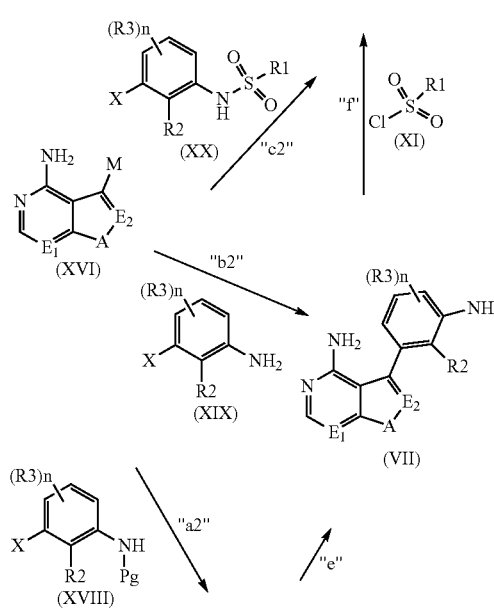
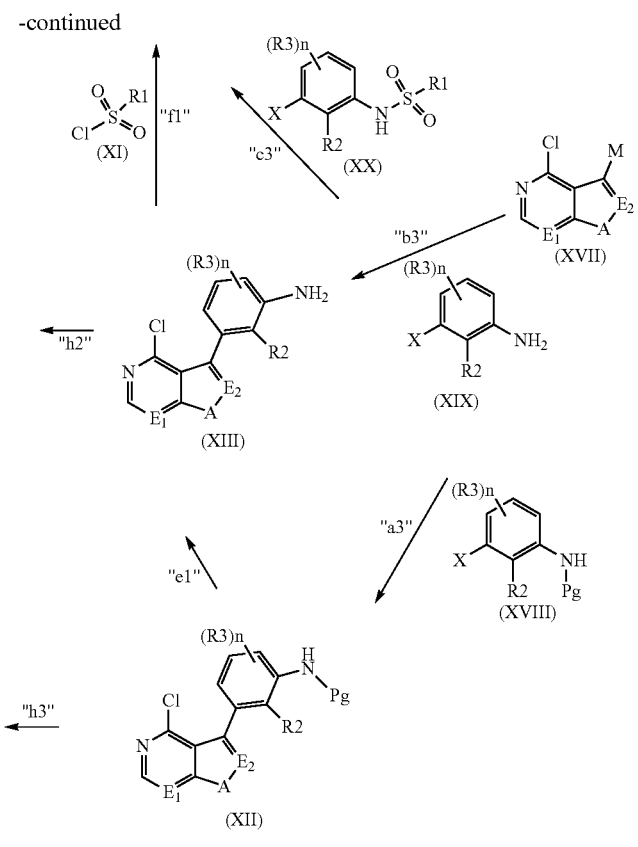

In the above scheme 2 A, $E_1$, $E_2$, R1, R2, R3, n, X, M and Pg are as defined above.

In a synthetic process for the preparation of a compound of formula (I), which is described in scheme 2, in steps "a2", "b2", "c2", or "d2" a compound of formula (XVI) is respectively reacted with a compound of formula (XVIII), (XIX), (XX), or (XXI) exploiting any of the cross-coupling reactions suitable for the formation of carbon-carbon bonds to yield respectively compounds of formula (V), (VII), (I), or (X). In step "e" a compound of formula (V) undergoes selective removal of the group Pg to give a compound of formula (VII), which, in step "f", is reacted with a sulfonyl chloride derivative of formula (XI) to yield a compound of formula (I). In step "g" selective removal of the protecting group from a compound of formula (X) yields a compound of formula (I).

In steps "a3", "b3", "c3", or "d3" a compound of formula (XVII) is respectively reacted with a compound of formula (XVIII), (XIX), (XX), or (XXI) exploiting any of the cross-coupling reactions suitable for the formation of carbon-carbon bonds to yield respectively compounds of formula (XII), (XIII), (XIV), or (XV). In step "e1" a compound of formula (XII) undergoes selective removal of the group Pg to give a compound of formula (XIII), which, in step "f1", is reacted with a sulfonyl chloride derivative of formula (XI) to yield a compound of formula (XIV). In step "g1" selective removal of the protecting group from a compound of formula (XV) yields a compound of formula (XIV).

In step "h" the reaction of a compound of formula (XV) with ammonia or an ammonia equivalent such as ammonium acetate, affords a compound of general formula (X). In step "h1" the same kind of reaction performed on a compound of formula (XIV) yields a compound of formula (I). In step "h2" the same kind of reaction performed on a compound of formula (XIII) yields a compound of formula (VII). In step "h3" the same kind of reaction performed on a compound of formula (XII) yields a compound of formula (V), According to steps "a2", "b2", "c2" and "d2" of scheme 2, the conversion of a compound of formula (XVI) into a compound respectively of formula (V), (VII), (I) and (X) is accomplished as described under step "a" of scheme 1.

According to steps "e" and "g" of scheme 2, the conversion of a compound of formula (V) and (X) respectively into a compound formula (VII) and (I) is accomplished as described under step "e" of scheme 1.

According to step "f" of scheme 2, the conversion of a compound of formula (VII) into a compound formula (I) is accomplished as described under step "f" of scheme 1.

According to steps "a3", "b3", "c3" and "d3" of scheme 2, the conversion of a compound of formula (XVII) into a compound respectively of formula (XII), (XIII), (XIV) and (XV) is accomplished as described under step "a" of scheme 1.

According to steps "e1" and "g1" of scheme 2, the conversion of a compound of formula (XII) and (XV) into a compound respectively of formula (XIII) and (XIV) is accomplished as described under step "e" of scheme 1.

According to step "f1" of scheme 2, the conversion of a compound of formula (XIII) into a compound of formula (XIV) is accomplished as described under step "f" of scheme 1.

According to steps "h", "h1", "h2" and "h3" of scheme 2, the conversion of a compound of formula (XV), (XIV), (XIII) and (XII) into a compound respectively of formula (X), (I), (VII) and (V) is accomplished as described under step "h" of scheme 1.

Alternatively, a compound of formula (II)A wherein X, $E_1$ and $E_2$ are as defined above and A is N—R5, wherein R5 is as defined above, can be prepared according to the following scheme 3:

alkylating agent of formula L-R5, to afford a compound of formula (XVI)A. Alternatively, in step "i1A", a compound of formula (III)A is converted into an organometal derivative of formula (XVII)A. In step "h4" the reaction of a compound of formula (XVII) with ammonia or an ammonia equivalent, affords a compound of general formula (XVI), while in step "h4A" the reaction of a compound of formula

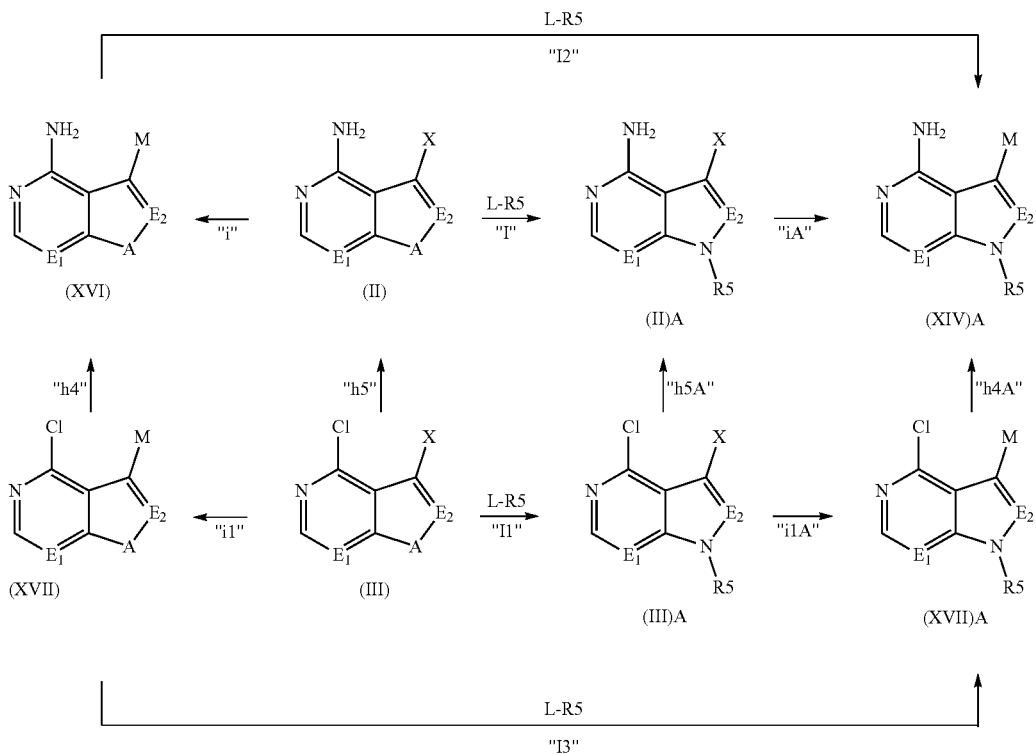

Scheme 3

In the above scheme 3 A, $E_1$, $E_2$, R1, R2, R3, n, X, M are as defined above and L is OH or a group that may work as a leaving group, such as a halogen atom, a tosylate, mesylate or triflate, or L is a group —B(OH)$_2$.

In a synthetic process for the preparation of a compound of formula (II)A which is described in scheme 3, in step "h5" the reaction of a compound of formula (III) with ammonia or an ammonia equivalent, affords a compound of general formula (II). When A is a group NH, in step "I" N-alkylation with a suitable alkylating agent of formula L-R5, affords a compound of formula (II)A. Alternatively, when A is a group NH, in step "I1" N-alkylation of a compound of formula (III) with a suitable alkylating agent of formula L-R5, affords a compound of formula (III)A. In step "h5A" such a compound of formula (III)A is treated with ammonia or an ammonia equivalent to afford a compound of general formula (II)A. In step "i" a compound of formula (II) is converted into an organometal derivative of formula (XVI), such as, for instance, an organo-boron or an organo-tin derivative, which in step "I2" is N-alkylated with a suitable alkylating agent of formula L-R5, to afford a compound of formula (XVI)A. Alternatively, in step "iA", a compound of formula (II)A is converted into an organometal derivative of formula (XVI)A. In step "i1" a compound of formula (III) is converted into an organometal derivative of formula (XVII), which in step "I3" is N-alkylated with a suitable (XVII)A with ammonia or an ammonia equivalent, affords a compound of general formula (XI)A.

According to steps "h5", "h5A", "h4" and "h4A" of scheme 3, the conversion of a compound of formula (III), (III)A, (XVII) and (XVIIA) into a compound respectively of formula (II), (IIA), (XVI) and (XVIA) is accomplished as described under step "h" of scheme 1.

According to step "l" of scheme 3, the conversion of a compound of formula (II) in another compound of formula (IIA) can be accomplished using a compound of formula L-R5 wherein L is OH, in which case the Mitsunobu reaction conditions can be employed, or L is a group that optionally upon activation, may work as a leaving group, such as a halogen atom, a tosylate, mesylate or triflate. In the former instance, that is, when a Mitsunobu protocol is employed, the reaction can be accomplished using a dialkyl azodicarboxylate, such as diethyl azodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, acetonitrile. When L is a halogen atom or a group such as tosylate, mesylate or triflate or the like the conversion can be accomplished using a suitable base such as, for instance, NaH, $K_2CO_3$, $CS_2CO_3$, NaOH, DBU, LiHMDS and the like, in a suitable solvent such as dichloromethane, tetrahydrofuran, 1,4-dioxane, 1,2-dimethoxyethane, methanol, ethanol, isopropanol, acetonitrile, acetic acid, N,N-dimethylformamide, N,N-dimethylacetamide, dimethylsulfoxide and the like. Said reactions can be carried out at temperatures ranging from 0° C. to reflux and for a time ranging from 30 minutes to about 48 hours. If required compounds of formula (IIA) can be separated and purified by silica gel chromatography or preparative HPLC.

According to steps "I1", "I2" and "I3" of scheme 3, the alkylation of a compound respectively of formula (III), (XVI) and (XVII) is accomplished as described under step "I" of scheme 3.

According to step "i" of scheme 3, a compound of formula (II) can be converted into a suitable organometallic derivative of formula (XVI), such as an organoboron, an organotin derivative or the like. Organoboron derivatives can be obtained for instance reacting a compound of formula (II) with a suitable boron compound, such as bis(pinacolato) diboron, pinacolborane, or the like in the presence of a suitable palladium catalyst such as palladium acetate (Pd (OAc)$_2$), 1,1'-bis(diphenylphosphino)ferrocene-palladium (II)dichloride dichloromethane complex (Pd(dppf) Cl$_2$.CH$_2$Cl$_2$) or Pd(CH$_3$CN)$_2$Cl$_2$ and of a suitable base, such as KOAc, triethylamine and the like, in solvents such as N,N-dimethylformamide, dimethylsulfoxide, dimethoxyethane, 1,4-dioxane, tetrahydrofuran, toluene or the like, at a temperature ranging from 20° C. to reflux and for a time ranging from 30 minutes to about 24 hours. Organotin derivatives can be obtained for instance by rection with a suitable organotin reagent such as hexamethylditin or the like, in the presence of a suitable palladium catalyst such as palladium tetrakis(triphenylphosphine) (Pd(PPh$_3$)$_4$) or palladium acetate (Pd(OAc)$_2$) optionally a suitable phosphine such as triphenylphosphine, and optionally in the presence of a suitable base, such as KOAc, triethylamine and the like, in solvents such as N,N-dimethylformamide, dimethylsulfoxide, dimethoxyethane, 1,4-dioxane, tetrahydrofuran, toluene or the like, at a temperature ranging from 20° C. to reflux and for a time ranging from 30 minutes to about 24 hours.

According to steps "iA", "i1" and "i1A" of scheme 3, the conversion of a compound of formula (II)A, (III) and (III)A into a compound respectively of formula (XVI)A, (XVII) and (XVII)A are accomplished as described under step "i" of scheme 3.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The starting materials of the process object of the present invention, comprehensive of any possible variant, as well as any reactant thereof, are known compounds and if not commercially available per se may be prepared according to well-known methods.

PHARMACOLOGY

The biochemical activity of compounds was determined by incubation with PERK recombinant enzyme (cytoplasmic domain corresponding to residues 540-1115) and eIF2alpha peptide substrate (Aminoacid sequence: LLSELSRRRIRSINK—SEQ ID Nr: 1; purchased from American Peptide Company, product #341923). This was followed by:

Method 1: Quantification of the ADP Tormed from the Kinase Reaction by ADP-Glo™ Kinase Assay (Promega Cat. 9102). Utra Pure ATP was Included into ADP-Glo™ Kinase Assay kit.

Compounds were 3-fold serially diluted in order to obtain from 3.333 to 0.000169 microM final concentration, then incubated for 60 minutes at room temperature in the presence of ATP, substrate and enzyme in a final volume of 15 microL of kinase buffer in 384-well plates (Perkin Elmer cat. #6007290).

The final concentration of the different reagents is 52 microM ATP, 8 nM PERK, 300 microM substrate, 50 mM Hepes pH 7.5, 3 mM MgCl$_2$, 1 mM DTT, 3 microM Na$_3$VO$_4$, 0.2 mg/ml BSA, 1% DMSO.

After 60 minutes, an equal volume (15 microL) of ADP-Glo™ Reagent was added to each well to terminate the kinase reaction and deplete the remaining ATP. After 40 minutes, 30 microL of Kinase Detection Reagent is added, which simultaneously converts ADP to ATP and allows the newly synthesized ATP to be measured using a coupled luciferase/luciferin reaction. After further 40 minutes luminescence was read by ViewLux Instrument (Perkin Elmer). The data are analyzed by GraphPad Prism software which provides sigmoidal fittings of the curves for IC$_{50}$ determination using a 4 parameter logistic equation:

$$y=\text{bottom}+(\text{top}-\text{bottom})/(1+10\hat{}((\log \text{IC}_{50}-x)*\text{slope}))$$

where x is the logarithm of the inhibitor concentration, y is the response; y starts at bottom and goes to top with a sigmoid shape.

Method 2: Quantification of the Phosphorylated Product Formed from the Kinase Reaction in Presence of ATP (Aldrich, Cat #A2620-9).

Serially diluted compounds were incubated for 60 minutes at room temperature in the presence of ATP/P$^{33}$ gammaATP mix, substrate and enzyme in a volume of 15 microL of kinase buffer in 384-well plates (Thermo Scientific, cat #4312).

The reaction volume contains, in final concentration, 52 microM ATP, 8 nM PERK and 300 microM substrate in 50 mM Hepes pH 7.5, 3 mM MgCl$_2$, 1 mM DTT, 3 microM Na$_3$VO$_4$, 0.2 mg/ml BSA. The final concentration of DMSO was 1%.

At the end of the incubation, an amount of 60 microL of Dowex resin (Sigma, customized resin 1×8 200-400 mesh cat #13858-U) in 150 mM sodium formate buffer pH=3.0 was added to stop the reaction and capture unreacted ATP/P$^{33}$ gammaATP, separating it from the phosphorylated substrate in solution. After 60 minutes of rest, a volume of 22 microL of supernatant was transferred into 384-Optiplates (Perkin-Elmer, cat #6007290). After the addition of 50 microL of Microscint 40 (Perkin-Elmer, cat #6013641), the radioactivity was counted in the TopCount (Perkin Elmer).

The data per each molecule are analyzed by an internally customized version of the SW package "Assay Explorer", or by GraphPad Prizm software alternatively, which provides sigmoidal fittings of the curves for IC$_{50}$ determination using a 4 parameter logistic equation:

$$y=\text{bottom}+(\text{top}-\text{bottom})/(1+10\hat{}((\log \text{IC}_{50}-x)*\text{slope}))$$

where x is the logarithm of the inhibitor concentration, y is the response; y starts at bottom and goes to top with a sigmoid shape.

The compounds were tested according to either of the above PERK enzyme assays and in at least one of the experimental run exhibited the $pIC_{50}$ activities against PERK as shown in the following Table A:

TABLE A

| Cmpd # | $pIC_{50}$ | Method |
|---|---|---|
| 1 | A | 1 |
| 2 | AA | 1 |
| 3 | AA | 1 |
| 4 | AA | 1 |
| 5 | A | 1 |
| 6 | AA | 1 |
| 9 | AA | 1 |
| 10 | C | 2 |
| 11 | C | 2 |
| 12 | A | 1 |
| 13 | AA | 1 |
| 14 | B | 1 |
| 15 | B | 1 |
| 17 | B | 1 |
| 18 | B | 1 |
| 19 | A | 1 |
| 20 | C | 1 |
| 21 | C | 1 |
| 22 | A | 1 |
| 23 | B | 1 |
| 24 | AA | 1 |
| 25 | A | 1 |
| 26 | A | 1 |
| 27 | AA | 1 |
| 28 | A | 1 |
| 29 | A | 1 |
| 30 | C | 1 |
| 32 | A | 1 |
| 33 | A | 1 |
| 34 | A | 1 |
| 35 | AA | 1 |
| 36 | A | 1 |
| 37 | A | 1 |
| 38 | AA | 1 |
| 39 | A | 1 |
| 40 | A | 1 |
| 41 | A | 1 |
| 44 | AA | 1 |
| 46 | AA | 1 |
| 47 | A | 1 |
| 48 | A | 1 |
| 49 | B | 1 |
| 50 | C | 1 |
| 51 | A | 1 |
| 52 | AA | 1 |
| 59 | B | 1 |
| 60 | C | 1 |
| 61 | A | 2 |
| 62 | A | 2 |
| 63 | A | 2 |
| 64 | A | 1 |
| 65 | B | 2 |
| 66 | B | 2 |
| 67 | C | 1 |
| 71 | AA | 2 |
| 72 | A | 2 |
| 73 | AA | 2 |
| 74 | B | 1 |
| 75 | A | 1 |
| 76 | B | 1 |
| 77 | A | 2 |
| 79 | A | 2 |
| 81 | B | 1 |
| 85 | A | 1 |
| 86 | A | 1 |

TABLE A-continued

| Cmpd # | $pIC_{50}$ | Method |
|---|---|---|
| 87 | AA | 1 |
| 89 | C | 2 |
| 90 | B | 2 |

The results for each compound were recorded as $pIC_{50}$, calculated as the negative logarithm of the $IC_{50}$ value (molar), and indicated by a code according to the following Table B:

TABLE B

| Code | $pIC_{50}$ value |
|---|---|
| AA | $7.8 \leq pIC_{50}$ |
| A | $7.3 \leq pIC_{50} < 7.8$ |
| B | $6.8 \leq pIC_{50} < 7.3$ |
| C | $pIC_{50} < 6.8$ |

From all of the above, the novel compounds of formula (I) of the invention appear to be particularly advantageous in the therapy of diseases caused by deregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 g to about 1 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

Experimental Section

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

g (grams) mg (milligrams)
mL (milliliters) mM (millimolar)
μM (micromolar) mmol (millimoles)
h (hours) MHz (Mega-Hertz)
mm (millimetres) Hz (Hertz)
M (molar) min (minutes)
mol (moles) TLC (thin layer chromatography)
r.t. (room temperature) TEA (triethylamine)
TFA (trifluoroacetic acid) DMF (N,N-dimethyl formamide)
DIPEA (N,N-diisopropyl-N-ethylamine) DCM (dichloromethane)
THF (tetrahydrofuran) AcOEt (ethyl acetate)
Hex (hexane) MeOH (Methanol)
DMSO (dimethylsulfoxide) TIPS (triisopropylsilyl)
Ac (acetyl) bs (broad singlet)
TBDMS (dimethyl-tert-butylsilyl) ESI (electrospray ionization)
BOC (tert-butyloxycarbonyl) Ac$_2$O (acetic anhydride)
NaH (sodium hydride, 60% in mineral oil)
TBTU (2-(1H-benzotriazol-1-yl)-1,1,3,3-tetramethyluronium tetrafluoroborate)
RP-HPLC (reverse phase high performance liquid chromatography)

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society or the Journal of Biological Chemistry.*

Unless otherwise noted, all materials were obtained from commercial suppliers, of the best grade and used without further purification. Anhydrous solvent such as DMF, THF, CH$_2$Cl$_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A).

Electrospray (ESI) mass spectra were obtained on a Thermo Finnigan LCQ Deca XP ion trap. HPLC-UV-MS analyses, used to assess compound purity, were carried out combining the ion trap MS instrument with HPLC system Surveyor (Thermo Finnigan) equipped with an autosampler and a diode array detector (UV detection 215-400 nm). Instrument control, data acquisition and processing were performed by using Xcalibur 1.4 SR1 software (Thermo Finnigan). HPLC chromatography was run at room temperature, and 1 ml/min flow rate, using a Phenomenex Gemini NX C18 column (4.6×50 mm; 3 μm). Mobile phase A was ammonium acetate 5 mM buffer (pH 5.5 with acetic acid): acetonitrile 95:5, and mobile phase B was ammonium acetate 5 mM buffer (pH 5.5 with acetic acid): acetonitrile 5:95; the gradient was from 0 to 100% B in 7 minutes then hold 100% B for 2 minutes before requilibration.

Exact mass data ESI(+) were obtained on a Waters Q-Tof Ultima directly connected with micro HPLC 1100 Agilent as previously described [M. Colombo, F. Riccardi-Sirtori, V. Rizzo, *Rapid Commun. Mass Sectrom.* 2004, 18, 511-517].

Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% NH$_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

Preparation 1

5-Iodo-7-methyl-7H-pyrrolo[2,3-d]pyrimidin-4-ylamine, compound of formula (II)A Scheme 3

4-Chloro-5-iodo-7-methyl-7H-pyrrolo[2,3-d]pyrimidine, compound of formula (III)A Scheme 3, Step 11

To 4-chloro-5-iodo-7H-pyrrolo[2,3-d]pyrimidine (2.38 g, 8.5 mmol) in N,N-dimethylformamide (DMF) (80 mL) at 0° C. was added 60% NaH (0.59 g, 14.7 mmol) portionwise. After $H_2$ bubbling stopped, iodomethane (0.66 mL, 10.6 mmol) was added and the reaction mixture was allowed to warm at room temperature. After 3 hours, the reaction mixture was poured slowly onto water and crushed ice (about 400 mL; Caution: $H_2$ evolution due to quenching excess NaH). The resulting white solid was filtered and washed with water and dried under vacuum to afford 4-chloro-5-iodo-7-methyl-7H-pyrrolo[2,3-d]pyrimidine (2.38 g).

HPLC (254 nm): Rt: 8.62 min.
HRMS (ESI) calcd for $C_7H_5ClIN_3$ $[M+H]^+$ 293.929, found 293.9296.
$^1$H NMR (401 MHz, DMSO-d6) delta ppm: 3.83 (s, 3H) 7.98 (s, 1H) 8.65 (s, 1H).

Analogously the following compounds were obtained:

4-Chloro-5-iodo-7-isopropyl-7H-pyrrolo[2,3-d]pyrimidine, compound of formula (III)A HPLC (254 nm): Rt: 11.17 min.
HRMS (ESI) calcd for $C_9H_9ClIN_3$ $[M+H]^+$ 321.9603, found 321.9605.
$^1$H NMR (401 MHz, DMSO-d6) delta ppm: 1.47 (d, J=6.71 Hz, 6H) 4.92-5.15 (m, 1H) 8.16 (s, 1H) 8.63 (s, 1H).

4-Chloro-7-ethyl-5-iodo-7H-pyrrolo[2,3-d]pyrimidine, compound of formula (III)A HPLC (254 nm): Rt: 6.16 min.
HRMS (ESI) calcd for $C_8H_7ClIN_3$ $[M+H]^+$ 307.9446, found 307.9455.
$^1$H NMR (500 MHz, DMSO-d6) delta ppm: 1.37 (t, J=7.24 Hz, 3H) 4.29 (q, J=7.22 Hz, 2H) 8.07 (s, 1H) 8.64 (s, 1H).

5-Iodo-7-methyl-7H-pyrrolo[2,3-d]pyrimidin-4-ylamine, compound of formula (II)A Scheme 3, Step h5A A suspension of 4-chloro-5-iodo-7-methyl-7H-pyrrolo[2,3-d]pyrimidine (1.16 g, 3.96 mmol) in ammonium hydroxide (10 mL, 75.43 mmol) and dioxane (5 mL) was stirred for 1 day at 125° C. in a sealed vessel. The reaction was allowed to cool to room temperature and poured in water and ice and filtered. The collected solid was washed with water to afford 5-iodo-7-methyl-7H-pyrrolo[2,3-d]pyrimidin-4-ylamine (0.93 g) as white solid.

HPLC (254 nm): Rt: 4.06 min.
HRMS (ESI) calcd for $C_7H_7IN_4$ $[M+H]^+$ 274.9788, found 274.9796.
$^1$H NMR (500 MHz, DMSO-d6) delta ppm: 3.67 (s, 3H) 6.59 (br. s., 2H) 7.42 (s, 1H) 8.10 (s, 1H).

Analogously the following compound was obtained:

5-Iodo-7-isopropyl-7H-pyrrolo[2,3-d]pyrimidin-4-ylamine, compound of formula (II)A HPLC (254 nm): Rt: 4.99 min.
HRMS (ESI) calcd for $C_9H_{11}IN_4$ $[M+H]^+$ 303.0101, found 303.0105.
$^1$H NMR (401 MHz, DMSO-d6) delta ppm: 1.40 (d, J=6.71 Hz, 6H) 4.89 (quin, J=6.74 Hz, 1H) 6.55 (br. s., 2H) 7.57 (s, 1H) 8.08 (s, 1H).

7-Ethyl-5-iodo-7H-pyrrolo[2,3-d]pyrimidin-4-ylamine, compound of formula (II)A HPLC (254 nm): Rt: 3.27 min.
HRMS (ESI) calcd for $C_9H_9IN_4$ $[M+H]^+$ 288.9945, found 288.9957.
$^1$H NMR (401 MHz, DMSO-d6) delta ppm: 1.31 (t, J=7.26 Hz, 3H) 4.13 (d, J=7.20 Hz, 2H) 6.38-6.72 (m, 2H) 7.47-7.50 (m, 1H) 8.09 (s, 1H).

Preparation 2

3-Iodo-1-methyl-1H-pyrazolo[3,4-d]pyrimidin-4-ylamine, compound of formula (II)A Scheme 3, Step I To a solution of 3-iodo-1H-pyrazolo[3,4-d]pyrimidin-4-ylamine (550 mg, 2.044 mmol) in DMF (20 mL) at 0° C. were added $Cs_2CO_3$ (770 mg, 2.362 mmol) and iodomethane (0.16 mL, 2.57 mmol). The reaction was allowed to warm at room temperature and stirred overnight. The reaction mixture was poured onto water and extracted with DCM. The organic phase was washed with brine, dried over $Na_2SO_4$ and evaporated. The crude was purified by silica gel chromatography which was eluted with DCM:MeOH=95:5 and the resulting solid triturated with $Et_2O$ to give 3-Iodo-1-methyl-1H-pyrazolo[3,4-d]pyrimidin-4-ylamine (170 mg) as white solid.

HPLC (254 nm): Rt: 3.55 min.
HRMS (ESI) calcd for C6H6IN5 $[M+H]^+$ 275.9741, found 275.9743.
$^1$H NMR (401 MHz, DMSO-d6) delta ppm: 3.88 (s, 3H) 7.49 (s, 2H) 8.21 (s, 1H).

Preparation 3

5-Iodo-7-(1-methyl-piperidin-4-yl)-7H-pyrrolo[2,3-d]pyrimidin-4-ylamine, compound of formula (II)A Scheme 3

4-(4-Chloro-5-iodo-pyrrolo[2,3-d]pyrimidin-7-yl)-piperidine-1-carboxylic acid tert-butyl ester, compound of formula (III)A Scheme 3, Step 11

To a solution of 4-chloro-5-iodo-7H-pyrrolo[2,3-d]pyrimidine (518 mg, 1.857 mmol), 4-hydroxy-piperidine-1-carboxylic acid tert-butyl ester (1.14 g, 5.671 mmol) and triphenylphosphine (984 mg, 3.775 mmol) in THF (10 mL) were added dropwise via syringe DEAD (0.6 mL, 3.669 mmol) and stirred for 3 h at room temperature. The reaction was concentrated, diluted with AcOEt and washed with NaOH 1.0N. The organic layer was then washed with brine, dried over $Na_2SO_4$ and evaporated. The crude was purified by silica gel chromatography which was eluted with Hexane:AcOEt=7:3 to afford 4-(4-chloro-5-iodo-pyrrolo[2,3-d]pyrimidin-7-yl)-piperidine-1-carboxylic acid tert-butyl ester (730 mg) as white solid.

HPLC (254 nm): Rt: 7.38 min.

HRMS (ESI) calcd for $C_{16}H_{20}O_2ICl$ [M+H]$^+$ 463.0393, found 463.04.

$^1$H NMR (401 MHz, DMSO-d6) delta ppm: 1.43 (s, 9H) 1.82-1.92 (m, 2H) 1.92-2.04 (m, 2H) 2.94 (br. s., 2H) 4.11 (m, J=11.60 Hz, 2H) 4.72-4.95 (m, 1H) 8.19 (s, 1H) 8.64 (s, 1H).

Analogously the following compound was obtained:

4-Chloro-5-iodo-7-(tetrahydro-pyran-4-yl)-7H-pyrrolo[2,3-d]pyrimidine, compound of formula (III)A HPLC (254 nm): Rt: 5.97 min.

HRMS (ESI) calcd for $C_{11}H_{11}N_3IOCl$ [M+H]$^+$ 363.9708, found 363.9724.

$^1$H NMR (401 MHz, DMSO-d6) delta ppm: 1.87 (dd, J=12.39, 2.26 Hz, 2H) 2.06-2.24 (m, 2H) 3.52 (td, J=11.84, 1.59 Hz, 2H) 3.99 (dd, J=11.47, 4.39 Hz, 2H) 4.82-5.00 (m, 1H) 8.18 (s, 1H) 8.64 (s, 1H).

4-Chloro-5-iodo-7-piperidin-4-yl-7H-pyrrolo[2,3-d]pyrimidine, compound of formula (III)A Scheme 3

To 4-(4-chloro-5-iodo-pyrrolo[2,3-d]pyrimidin-7-yl)-piperidine-1-carboxylic acid tert-butyl ester (240 mg, 0.519 mmol) in dioxane (8 mL) was added HCl in dioxane 4M (4 ml, 16 mmol) and the reaction stirred at 45° C. overnight. The reaction solvent was evaporated and the resulting white solid was diluted with DCM and NaOH 1.0N. The water layer was extracted with DCM and the combined organic phase was washed with brine, dried over Na$_2$SO$_4$ and evaporated to furnished 4-chloro-5-iodo-7-piperidin-4-yl-7H-pyrrolo[2,3-d]pyrimidine (157 mg) as white solid.

HPLC (254 nm): Rt: 4.29 min.

HRMS (ESI) calcd for $C_{11}H_{12}N_4ICl$ [M+H]$^+$ 362.9868, found 362.9874.

$^1$H NMR (500 MHz, DMSO-d6) delta ppm: 1.90-2.00 (m, 2H) 2.00-2.16 (m, 2H) 2.79-2.94 (m, 2H) 3.12-3.28 (m, 2H) 4.74-4.87 (m, 1H) 8.08 (s, 1H) 8.65 (s, 1H).

Analogously the following compound was obtained:

5-Iodo-7-piperidin-4-yl-7H-pyrrolo[2,3-d]pyrimidin-4-ylamine, compound of formula (II)A HPLC (254 nm): Rt: 3.17 min. HRMS (ESI) calcd for $C_{11}H_{14}IN_5$ [M+H]$^+$ 344.0367, found 344.0369.

$^1$H NMR (500 MHz, DMSO-d6) delta ppm: 1.60-1.90 (m, 4H) 2.55-2.62 (m, 2H) 3.03 (d, J=12.51 Hz, 2H) 4.47-4.62 (m, 1H) 5.71-7.16 (m, 2H) 7.52 (s, 1H) 8.07 (s, 1H).

4-Chloro-5-iodo-7-(1-methyl-piperidin-4-yl)-7H-pyrrolo[2,3-d]pyrimidine, compound of formula (III)A Scheme 3

To 4-chloro-5-iodo-7-piperidin-4-yl-7H-pyrrolo[2,3-d]pyrimidine (518 mg, 1.430 mmol) in DCM (15 mL) was added AcOH (90 microL, 1.575 mmol), formaldehyde solution 37 wt. % in water (550 microL, 7.346 mmol) and stirred at room temperature. After 15 min was added NaBH(OAc)$_3$ (1.62 g, 7.412 mmol) portionwise and the reaction was let to stir at room temperature overnight. The mixture was diluted with DCM and washed with NaOH 2.0N. The organic layer was washed with brine, dried over Na$_2$SO$_4$ and evaporated to afford 4-chloro-5-iodo-7-(1-methyl-piperidin-4-yl)-7H-pyrrolo[2,3-d]pyrimidine (491 mg) as white solid.

HPLC (254 nm): Rt: 4.37 min.

HRMS (ESI) calcd for $C_{12}H_{14}N_4ICl$ [M+H]$^+$ 377.0025, found 377.0042.

$^1$H NMR (401 MHz, DMSO-d6) delta ppm: 1.88 (m, J=8.91 Hz, 2H) 2.03-2.18 (m, 4H) 2.23 (s, 3H) 2.91 (m, J=8.67 Hz, 2H) 4.62 (m, J=11.63, 11.63, 4.33 Hz, 1H) 8.15 (s, 1H) 8.63 (s, 1H).

Analogously the following compounds were obtained:

4-Chloro-5-iodo-7-(1-isopropyl-piperidin-4-yl)-7H-pyrrolo[2,3-d]pyrimidine, compound of formula (III)A HPLC (254 nm): Rt: 4.63 min.

HRMS (ESI) calcd for $C_{14}H_{18}N_4ICl$ [M+H]$^+$ 405.0338, found 405.0346.

$^1$H NMR (500 MHz, DMSO-d6) delta ppm: 1.00 (d, J=6.56 Hz, 6H) 1.84-1.94 (m, 2H) 1.98-2.13 (m, 2H) 2.24-2.35 (m, 2H) 2.76 (br. s., 1H) 2.92 (d, J=10.68 Hz, 2H) 4.61 (t, J=12.35 Hz, 1H) 8.16 (s, 1H) 8.63 (s, 1H).

4-Chloro-7-(1-cyclopropyl-piperidin-4-yl)-5-iodo-7H-pyrrolo[2,3-d]pyrimidine, compound of formula (III)A HPLC (254 nm): Rt: 6.35 min.

HRMS (ESI) calcd for $C_{14}H_{16}N_4ICl$ [M+H]$^+$ 403.0181, found 403.0183.

$^1$H NMR (500 MHz, DMSO-d6) delta ppm: 0.28-0.37 (m, 2H) 0.40-0.48 (m, 2H) 1.63-1.73 (m, 1H) 1.81-1.93 (m, 2H) 2.05 (s, 3H) 2.31-2.42 (m, 2H) 3.02-3.12 (m, 1H) 4.61-4.74 (m, 1H) 8.14 (s, 1H) 8.63 (s, 1H).

5-Iodo-7-(1-methyl-piperidin-4-yl)-7H-pyrrolo[2,3-d]pyrimidin-4-ylamine, compound of formula (II)A Scheme 3, Step h5A To a 5 mL microwave vial charged with dioxane (4 mL) was added 4-chloro-5-iodo-7-(1-methyl-piperidin-4-yl)-7H-pyrrolo[2,3-d]pyrimidine (469 mg, 1.247 mmol), ammonium hydroxide (10 mL, 76.46 mmol) and sealed. The reaction vessel was heated under microwave irradiation for 180 min at 130° C. The mixture was diluted with water and extracted with DCM. The combined organic phase was washed with brine, dried over Na$_2$SO$_4$ and evaporated. The solid obtained was triturated with Et$_2$O to afford 5-Iodo-7-(1-methyl-piperidin-4-yl)-7H-pyrrolo[2,3-d]pyrimidin-4-ylamine (374 mg) as white solid.

HPLC (254 nm): Rt: 3.22 min.

HRMS (ESI) calcd for $C_{12}H_{16}N_5I$ [M+H]$^+$ 358.0523, found 358.0535.

$^1$H NMR (401 MHz, DMSO-d6) delta ppm: 1.74-1.87 (m, 2H) 1.94-2.12 (m, 4H) 2.23 (s, 3H) 2.89 (m, J=8.06 Hz, 2H) 4.31-4.60 (m, 1H) 6.57 (br. s., 2H) 7.56 (s, 1H) 8.08 (s, 1H).

Analogously the following compounds were obtained:

5-Iodo-7-(1-isopropyl-piperidin-4-yl)-7H-pyrrolo[2,3-d]pyrimidin-4-ylamine, compound of formula (II)A HPLC (254 nm): Rt: 3.50 min.

HRMS (ESI) calcd for $C_{14}H_{20}N_5I$ [M+H]$^+$ 386.0836, found 386.0845.

¹H NMR (500 MHz, DMSO-d6) delta ppm: 0.99 (d, J=6.56 Hz, 6H) 1.82 (dt, J=11.78, 1.81 Hz, 2H) 1.96 (qd, J=12.20, 3.97 Hz, 2H) 2.26 (t, J=11.21 Hz, 2H) 2.74 (spt, J=6.60 Hz, 1H) 2.89 (d, J=11.44 Hz, 2H) 4.45 (tt, J=11.93, 3.85 Hz, 1H) 6.58 (br. s., 2H) 7.57 (s, 1H) 8.08 (s, 1H).

7-(1-Cyclopropyl-piperidin-4-yl)-5-iodo-7H-pyrrolo[2,3-d]pyrimidin-4-ylamine, compound of formula (II)A HPLC (254 nm): Rt: 4.04 min.
HRMS (ESI) calcd for $C_{14}H_{18}N_5I$ $[M+H]^+$ 384.068, found 384.0689.
¹H NMR (500 MHz, DMSO-d6) delta ppm: 0.27-0.34 (m, 2H) 0.41-0.48 (m, 2H) 1.67 (tt, J=6.58, 3.49 Hz, 1H) 1.79 (d, J=11.59 Hz, 2H) 1.95 (qd, J=12.23, 3.43 Hz, 2H) 2.32 (t, J=11.29 Hz, 2H) 3.04 (d, J=11.90 Hz, 2H) 4.51 (tt, J=11.95, 3.98 Hz, 1H) 6.59 (br. s., 2H) 7.55 (s, 1H) 8.08 (s, 1H).

5-Iodo-7-(tetrahydro-pyran-4-yl)-7H-pyrrolo[2,3-d]pyrimidin-4-ylamine, compound of formula (II)A HPLC (254 nm): Rt: 4.42 min.
HRMS (ESI) calcd for $C_{11}H_{13}IN_4O$ $[M+H]^+$ 345.0207, found 345.0213.
¹H NMR (401 MHz, DMSO-d6) delta ppm: 1.80 (m, J=12.27, 2.38 Hz, 2H) 1.98-2.12 (m, 2H) 3.48 (td, J=11.93, 1.77 Hz, 2H) 3.97 (dd, J=11.35, 4.27 Hz, 2H) 4.63-4.86 (m, 1H) 6.59 (br. s., 2H) 7.60 (s, 1H) 8.09 (s, 1H).

4-(4-Amino-5-iodo-pyrrolo[2,3-d]pyrimidin-7-yl)-piperidine-1-carboxylic acid tert-butyl ester, compound of formula (II)A To a 5 mL microwave vial charged with dioxane (1 mL) was added 4-(4-chloro-5-iodo-pyrrolo[2,3-d]pyrimidin-7-yl)-piperidine-1-carboxylic acid tert-butyl ester (115 mg, 0.249 mmol), ammonium hydroxide (2 mL, 16.6 mmol) and sealed. The reaction vessel was heated under microwave irradiation for 120 min at 100° C. The mixture was diluted with water and extracted with DCM. The combined organic phase was washed with brine, dried over $Na_2SO_4$ and evaporated. The crude was purified by silica gel chromatography which was eluted with DCM:MeOH=90:10 to afford 4-(4-amino-5-iodo-pyrrolo[2,3-d]pyrimidin-7-yl)-piperidine-1-carboxylic acid tert-butyl ester (80 mg) as white solid.
HPLC (254 nm): Rt: 5.98 min.
HRMS (ESI) calcd for $C_{16}H_{22}N_5O_2I$ $[M+H]^+$ 444.0891, found 444.088.
¹H NMR (500 MHz, DMSO-d6) delta ppm: 1.42 (s, 9H) 1.69-1.94 (m, 4H) 2.75-3.02 (m, 2H) 4.04-4.23 (m, 2H) 4.59-4.79 (m, 1H) 6.59 (br. s., 2H) 7.61 (s, 1H) 8.08 (s, 1H).

Preparation 4

4-(4-Amino-3-iodo-pyrazolo[3,4-d]pyrimidin-1-yl)-piperidine-1-carboxylic acid tert-butyl ester, compound of formula (II)A Scheme 3, Step I
To a solution of 3-iodo-1H-pyrazolo[3,4-d]pyrimidin-4-ylamine (300 mg, 1.115 mmol), 4-hydroxy-piperidine-1-carboxylic acid tert-butyl ester (680 mg, 3.383 mmol) and triphenylphosphine (593 mg, 2.263 mmol) in THF (10 mL) was added dropwise via syringe DEAD (0.37 mL, 2.262 mmol) and stirred for 3 h at room temperature. The reaction was concentrated, diluted with AcOEt and washed with NaOH 1.0N. The organic layer was washed with brine, dried over $Na_2SO_4$ and evaporated. The crude was purified by silica gel chromatography which was eluted with Hexane:AcOEt=1:1 to afford 4-(4-amino-3-iodo-pyrazolo[3,4-d]pyrimidin-1-yl)-piperidine-1-carboxylic acid tert-butyl ester (300 mg) as white solid.
HPLC (254 nm): Rt: 5.72 min.
HRMS (ESI) calcd for $C_{15}H_{21}N_6O_2I$ $[M+H]^+$ 445.0844, found 445.0839.
¹H NMR (401 MHz, DMSO-d6) delta ppm: 1.43 (s, 9H) 1.79-1.93 (m, 4H) 2.95 (br. s., 2H) 3.91-4.20 (m, 2H) 4.81 (tt, J=10.51, 5.23 Hz, 1H) 5.91-7.38 (m, 2H) 8.19 (s, 1H).

Preparation 5

3-Bromo-thieno[3,2-c]pyridin-4-ylamine, compound of formula (II)

Scheme 3, Step h5
3-Bromo-4-chloro-thieno[3,2-c]pyridine (300 mg, 1.21 mmol) was dissolved in NMP (3 mL) and placed in a 20-mL microwave vial. A saturated solution of $NH_4Cl$ (5 mL) was added to the vial and the mixture was microwave heated at 150° C. for a total time of 3 h. The mixture was then diluted with water and extracted with ethyl acetate. The aqueous solution was then basified with NaOH and extracted with AcOEt. The latter solution was dried with $Na_2SO_4$ and evaporated to dryness. The residue was purified by flash column chromatography over silica gel eluting with DCM to yield 3-bromo-thieno[3,2-c]pyridin-4-ylamine (84 mg).
HPLC (254 nm): Rt: 4.38 min.
HRMS (ESI) calcd for $C_7H_5BrN_2S$ $[M+H]^+$ 228.9430, found 228.9441.
1H NMR (500 MHz, DMSO-d6) delta ppm: 6.49 (s, 2H) 7.27 (d, J=5.64 Hz, 1H) 7.78 (s, 1H) 7.83 (d, J=5.64 Hz, 1H).
Analogously the following compound was obtained:

3-Bromo-furo[3,2-c]pyridin-4-ylamine, compound of formula (II)

HPLC (254 nm): Rt: 3.91 min.
HRMS (ESI) calcd for $C_7H_5BrN_2S$ $[M+H]^+$ 212.9658, found 212.9659.
1H NMR (500 MHz, DMSO-d6) delta ppm: 1H NMR (500 MHz, DMSO-d6) 6.19 (br. s., 2H) 6.92 (d, J=5.95 Hz, 1H) 7.85 (d, J=5.95 Hz, 1H) 8.12 (s, 1H).

Preparation 6

2-Fluoro-3-(4,4,5,5-tetramethyl-[1,3,2]dioxaborolan-2-yl)-phenylamine, compound of formula (VI)

Scheme 1
A mixture of 3-bromo-2-fluoro-phenylamine (6.52 g, 33.63 mmol), bis(pinacolato)diboron (10.45 g, 41.14 mmol), [1,1'-bis(diphenylphosphino)ferrocene]dichloropalladium (II), complex with dichloromethane (1:1) (1.12 g, 1.37 mmol) and potassium acetate (10.1 g, 103.06 mmol) in dry DMF (65 mL) was heated at 100° C. under an atmosphere of nitrogen for 7 hours. The reaction was allowed to cool to room temperature, diluted with AcOEt and filtered through celite. The organic was washed with water, brine, dried over $Na_2SO_4$ and evaporated. The crude was purified by silica gel chromatography which was eluted with hexane:AcOEt=8:2 to afford 2-fluoro-3-(4,4,5,5-tetramethyl-[1,3,2]dioxaborolan-2-yl)-phenylamine (6.90 g) as white solid.

HPLC (254 nm): Rt: 5.94 min.

HRMS (ESI) calcd for $C_{12}H_{17}BNO_2F$ [M+H]$^+$ 237.1446, found 237.1453.

$^1$H NMR (401 MHz, DMSO-d6) delta ppm: 1.28 (s, 12H) 4.99 (s, 2H) 6.67-6.78 (m, 1H) 6.80-6.92 (m, 2H).

Analogously the following compounds were obtained:

2-Chloro-3-(4,4,5,5-tetramethyl-[1,3,2]dioxaborolan-2-yl)-phenylamine, compound of formula (VI)

HRMS (ESI) calcd for $C_{12}H_{17}BNO_2Cl$ [M+H]$^+$ 253.115, found 253.114.

$^1$H NMR (500 MHz, DMSO-d6) delta ppm: 1.28 (s, 12H) 5.27 (s, 2H) 6.77 (dd, J=7.09, 1.60 Hz, 1H) 6.86 (dd, J=7.93, 1.68 Hz, 1H) 6.95-7.03 (m, 1H).

2-Methyl-3-(4,4,5,5-tetramethyl-[1,3,2]dioxaborolan-2-yl)-phenylamine, compound of formula (VI)

HPLC (254 nm): Rt: 6.34 min.

HRMS (ESI) calcd for $C_{13}H_{20}BNO_2$ [M+H]$^+$ 233.1696, found 233.1698.

$^1$H NMR (401 MHz, DMSO-d6) delta ppm: 1.28 (s, 12H) 2.20 (s, 3H) 4.70 (s, 2H) 6.67-6.73 (m, 1H) 6.83-6.90 (m, 2H).

2-Amino-6-(4,4,5,5-tetramethyl-[1,3,2]dioxaborolan-2-yl)-benzonitrile, compound of formula (VI)

HRMS (ESI) calcd for $C_{13}H_{17}BN_2O_2$ [M+Na]$^+$ 266.1311, found 266.1307.

$^1$H NMR (500 MHz, DMSO-d6) delta ppm: 1.29 (s, 12H) 5.93 (s, 2H) 6.90 (ddd, J=9.72, 7.82, 1.07 Hz, 2H) 7.24-7.33 (m, 1H).

Preparation 7

[2-Fluoro-3-(4,4,5,5-tetramethyl-[1,3,2]dioxaborolan-2-yl)-phenyl]-carbamic acid tert-butyl ester, compound of formula (IV)

Scheme 1

(3-Bromo-2-fluoro-phenyl)-carbamic acid tert-butyl ester

To a suspension of 3-bromo-2-fluoro-phenylamine (5.48 g, 28.84 mmol) in NaOH 2N (100 mL, 200 mmol) was added di-tert-butyl dicarbonate (10.07 g, 46.19 mmol) and the mixture was kept under mechanic stirring and heated at reflux. After 24 hours the reaction was cool down at room temperature, diluted with DCM (100 mL) and the organic was separated. The aqueous layer was extracted with DCM and the combined organic phase was washed with brine, dried over $Na_2SO_4$ and evaporated. The crude was purified by silica gel chromatography (gradient: hexane:AcOEt=100:0 to 70:30) to recover unreacted starting material (1.10 g) and afford the title compound (6.43 g) as white solid.

HPLC (254 nm): Rt: 7.37 min.

HRMS (ESI) calcd for $C_{13}H_2OBNO_2$ [M+Na]$^+$ 312.0006, found 312.0004.

$^1$H NMR (600 MHz, DMSO-d6) delta ppm: 1.46 (s, 9H) 7.09 (t, J=7.69 Hz, 1H) 7.29-7.44 (m, 1H) 7.60 (t, J=7.51 Hz, 1H) 9.16 (s, 1H).

[2-Fluoro-3-(4,4,5,5-tetramethyl-[1,3,2]dioxaborolan-2-yl)-phenyl]-carbamic acid tert-butyl ester, compound of formula (IV)

Scheme 1

In a sealed tube, to (3-bromo-2-fluoro-phenyl)-carbamic acid tert-butyl ester (4.08 g, 14.07 mmol), bis(pinacolato)diboron (5.55 g, 21.85 mmol) and potassium acetate (4.35 g, 44.38 mmol) was added dioxane (100 mL) and the mixture was degassed with $N_2$. [1,1'-Bis(diphenylphosphino) ferrocene]dichloropalladium(II), complex with dichloromethane (1:1) (559 mg, 0.684 mmol) was added and the reaction was stirred at 100° C. overnight. The mixture was cooled down at room temperature, diluted with AcOEt and passed through celite. The combined organic layer was evaporated and the crude was purified by silica gel chromatography (gradient hexane:AcOEt=100:0 to 70:30) to furnish the title compound (4.6 g) as a solid.

HRMS (ESI) calcd for $C_{17}H_{25}BFNO_4$ [M+Na]$^+$ 359.1789, found 359.1791.

$^1$H NMR (600 MHz, DMSO-d6) delta ppm: 1.29 (s, 12H) 1.46 (s, 9H) 7.12 (t, J=7.60 Hz, 1H) 7.33 (ddd, J=7.19, 5.27, 1.65 Hz, 1H) 7.70 (t, J=7.51 Hz, 1H) 8.86 (s, 1H).

Preparation 8

3-Chloro-N-[2-fluoro-3-(4,4,5,5-tetramethyl-[1,3,2]dioxaborolan-2-yl)-phenyl]-4-methoxy-N-methoxymethyl-benzenesulfonamide, compound of formula (IX)

Scheme 1

N-(3-Bromo-2-fluoro-phenyl)-3-chloro-4-methoxy-benzenesulfonamide, compound of formula (XX)

Scheme 3

To a solution of 3-bromo-2-fluoro-phenylamine (1.10 g, 5.67 mmol) in DCM (50 mL) was added pyridine (0.68 mL, 8.51 mmol), 3-chloro-4-methoxy-benzenesulfonyl chloride (1.37 g, 5.70 mmol) and stirred at room temperature overnight. The reaction mixture was diluted with DCM, washed with saturated aqueous $NaHCO_3$, saturated aqueous $NH_4Cl$, brine and dried over $Na_2SO_4$. The organic solvent was removed under reduce pressure and the crude triturated with $Et_2O$ to give the title compound (1.63 g) as a white solid.

HPLC (254 nm): Rt: 5.74 min.

HRMS (ESI) calcd for $C_{13}H_{10}BrClFNO_3S$ [M+Na]$^+$ 415.9129, found 415.9135.

$^1$H NMR (600 MHz, DMSO-d6) delta ppm: 3.93 (s, 3H) 7.10 (td, J=8.10, 1.19 Hz, 1H) 7.22-7.25 (m, 1H) 7.31 (d, J=8.79 Hz, 1H) 7.47-7.52 (m, 1H) 7.66 (dd, J=8.70, 2.29 Hz, 1H) 7.74 (d, J=2.38 Hz, 1H) 10.37 (s, 1H).

N-(3-Bromo-2-fluoro-phenyl)-3-chloro-4-methoxy-N-methoxymethyl-benzenesulfonamide, compound of formula (XXI)

Scheme 3

To a solution of N-(3-bromo-2-fluoro-phenyl)-3-chloro-4-methoxy-benzenesulfonamide (505 mg, 1.282 mmol) in DCM (15 mL) was added DIPEA (0.35 mL, 2.048 mmol) and chloro-methoxy-methane (0.16 mL, 2.055 mmol) and stirred overnight at room temperature. The reaction was diluted with DCM, washed with saturated $NH_4Cl$, brine and dried over Na$_2$SO$_4$. The organic solvent was removed under reduce pressure to give the title compound (480 mg) as a solid.

HPLC (254 nm): Rt: 6.99 min.

HRMS (ESI) calcd for C$_{15}$H$_{14}$BrClFNO$_4$S [M+Na]$^+$ 459.9391, found 459.9391.

$^1$H NMR (600 MHz, DMSO-d6) delta ppm: 3.30 (s, 3H) 3.97 (s, 3H) 4.99 (s, 2H) 7.07-7.23 (m, 2H) 7.34 (d, J=8.79 Hz, 1H) 7.64 (dd, J=8.79, 2.38 Hz, 1H) 7.72 (d, J=2.38 Hz, 1H) 7.74-7.79 (m, 1H).

Analogously the following compound was obtained:

N-(3-Bromo-2-cyano-phenyl)-5-chloro-2-fluoro-4-methoxy-N-methoxymethyl-benzenesulfonamide, compound of formula (XXI)

HPLC (254 nm): Rt: 6.74 min.

HRMS (ESI) calcd for C$_{16}$H$_{13}$BrClFN$_2$O$_4$S [M+Na]$^+$ 484.9344, found 484.9331.

1H NMR (500 MHz, DMSO-d6) delta ppm: 3.40 (s, 3H) 3.98 (s, 3H) 5.09 (s, 2H) 7.37 (d, J=8.08 Hz, 1H) 7.43 (d, J=12.35 Hz, 1H) 7.64 (d, J=7.47 Hz, 1H) 7.67 (t, J=8.16 Hz, 1H) 7.96 (dd, J=8.24, 0.92 Hz, 1H).

3-Chloro-N-[2-fluoro-3-(4,4,5,5-tetramethyl-[1,3,2]dioxaborolan-2-yl)-phenyl]-4-methoxy-N-methoxymethyl-benzenesulfonamide, compound of formula (IX)

Scheme 1

In a Schlenk tube, to N-(3-bromo-2-fluoro-phenyl)-3-chloro-4-methoxy-N-methoxymethyl-benzenesulfonamide (479 mg, 1.093 mmol), bis(pinacolato)diboron (345 mg, 1.358 mmol) and potassium acetate (295 mg, 3.010 mmol) was added dioxane (12 mL) and the mixture was degassed with N2. [1,1'-Bis(diphenylphosphino)ferrocene]dichloropalladium(II), complex with dichloromethane (1:1) (47 mg, 0.057 mmol) was added and the reaction stirred at 100° C. overnight. The mixture was cool down at room temperature, diluted with AcOEt and passed through celite. The combined organic layer was evaporated and the crude was purified by silica gel chromatography (gradient hexane: AcOEt=80:20 to 60:40) to furnish the title compound (400 mg) as a solid.

MS (ESI) for C$_{21}$H$_{26}$BClFNO$_6$S (MW:485.77): [M+H]$^+$ found 486

Preparation 9

3-Chloro-N-[2-fluoro-3-(4,4,5,5-tetramethyl-[1,3,2]dioxaborolan-2-yl)-phenyl]-4-methoxy-benzenesulfonamide, compound of formula (VIII)

Scheme 1

To a solution of 2-fluoro-3-(4,4,5,5-tetramethyl-[1,3,2]dioxaborolan-2-yl)-phenylamine (163 mg, 0.685 mmol) in DCM (10 mL) were added pyridine (0.28 mL, 3.484 mmol), 3-chloro-4-methoxy-benzenesulfonyl chloride (197 mg, 0.820 mmol) and stirred at room temperature for 2h. The reaction was diluted with DCM and washed with saturated NaHCO$_3$, brine and dried over Na$_2$SO$_4$. The organic solvent was evaporated under vacuum and the residue was triturated with hexane to give the title compound (250 mg) as a solid.

HRMS (ESI) calcd for C$_{19}$H$_{22}$BClFNO$_5$S [M+Na]$^+$ 463.0913, found 463.0897.

$^1$H NMR (500 MHz, DMSO-d6) delta ppm: 1.20-1.31 (m, 12H) 3.91 (s, 3H) 7.13 (t, J=7.63 Hz, 1H) 7.29 (d, J=8.85 Hz, 1H) 7.35-7.42 (m, 1H) 7.65 (dd, J=8.85, 2.29 Hz, 1H) 7.69 (d, J=2.14 Hz, 1H) 7.93 (t, J=7.63 Hz, 1H) 10.09-10.21 (m, 1H).

Analogously the following compounds were obtained:

5-Chloro-2-fluoro-N-[2-fluoro-3-(4,4,5,5-tetramethyl-[1,3,2]dioxaborolan-2-yl)-phenyl]-4-methoxy-benzenesulfonamide, compound of formula (VIII)

$^1$H NMR (401 MHz, DMSO-d6) delta ppm: 1.27 (s, 12H) 3.94 (s, 3H) 7.14 (t, J=7.60 Hz, 1H) 7.33-7.46 (m, 3H) 7.63 (d, J=7.32 Hz, 1H) 10.38 (s, 1H).

3-Chloro-N-[2-chloro-3-(4,4,5,5-tetramethyl-[1,3,2]dioxaborolan-2-yl)-phenyl]-4-methoxy-benzenesulfonamide, compound of formula (VIII)

HRMS (ESI) calcd for C$_{19}$H$_{22}$BCl$_2$NO$_5$S [M+Na]$^+$ 479.0617, found 479.0607.

$^1$H NMR (500 MHz, DMSO-d6) delta ppm: 1.28 (s, 12H) 3.93 (s, 3H) 7.24-7.34 (m, 3H) 7.42 (dd, J=6.94, 2.06 Hz, 1H) 7.65 (dd, J=8.69, 2.29 Hz, 1H) 7.74 (d, J=2.44 Hz, 1H) 9.97 (s, 1H).

5-Chloro-N-[2-chloro-3-(4,4,5,5-tetramethyl-[1,3,2]dioxaborolan-2-yl)-phenyl]-2-fluoro-4-methoxy-benzenesulfonamide, compound of formula (VIII)

$^1$H NMR (500 MHz, DMSO-d6) delta ppm: 1.28 (s, 12H) 3.95 (s, 3H) 7.27-7.33 (m, 1H) 7.34-7.39 (m, 2H) 7.46 (dd, J=7.32, 1.68 Hz, 1H) 7.61 (d, J=7.32 Hz, 1H) 10.29 (s, 1H).

3,4-Dichloro-N-[2-fluoro-3-(4,4,5,5-tetramethyl-[1,3,2]dioxaborolan-2-yl)-phenyl]-benzenesulfonamide, compound of formula (VIII)

$^1$H NMR (500 MHz, DMSO-d6) delta ppm: 1.26 (s, 12H) 7.16 (t, J=7.70 Hz, 1H) 7.38 (td, J=7.85, 1.68 Hz, 1H) 7.44 (ddd, J=7.09, 5.49, 1.60 Hz, 1H) 7.65 (dd, J=8.54, 2.14 Hz, 1H) 7.82 (d, J=2.14 Hz, 1H) 7.87 (d, J=8.54 Hz, 1H) 10.36 (s, 1H).

4-Bromo-2-fluoro-N-[2-fluoro-3-(4,4,5,5-tetramethyl-[1,3,2]dioxaborolan-2-yl)-phenyl]-benzenesulfonamide, compound of formula (VIII)

HRMS (ESI) calcd for C$_{18}$H$_{19}$BBrF$_2$NO$_4$S [M+Na]$^+$ 495.0208, found 495.0204.

$^1$H NMR (500 MHz, DMSO-d6) delta ppm: 1.27 (s, 12H) 7.14 (t, J=7.70 Hz, 1H) 7.38 (td, J=7.82, 1.60 Hz, 1H) 7.44 (ddd, J=7.21, 5.30, 1.68 Hz, 1H) 7.57 (dd, J=8.50, 1.80 Hz, 1H) 7.61 (dd, J=8.20, 7.60 Hz, 1H) 7.88 (dd, J=9.76, 1.68 Hz, 1H) 10.54 (s, 1H).

2-Fluoro-N-[2-fluoro-3-(4,4,5,5-tetramethyl-[1,3,2]dioxaborolan-2-yl)-phenyl]-4-methoxy-5-methyl-benzenesulfonamide, compound of formula (VIII)

HRMS (ESI) calcd for C$_{20}$H$_{24}$BF$_2$NO$_5$S [M+Na]$^+$ 461.1365, found 461.1362.

$^1$H NMR (500 MHz, DMSO-d6) delta ppm: 1.27 (s, 12H) 2.08 (s, 3H) 3.85 (s, 3H) 7.07 (d, J=12.35 Hz, 1H) 7.11 (t, J=7.70 Hz, 1H) 7.39 (t, J=6.94 Hz, 2H) 7.44 (d, J=8.39 Hz, 1H) 10.19 (s, 1H).

For the following compound, the corresponding boronic acid was isolated:

(2-fluoro-3-{[(4-fluoro-2-iodophenyl)sulfonyl]amino}phenyl)boronic acid, compound of formula (VIII)

HRMS (ESI) calcd for $C_{12}H_9BF_2INO_4S$ [M+Na]$^+$ 460.9286, found 460.9297.

$^1$H NMR (500 MHz, DMSO-d6) delta ppm: 7.10 (t, J=7.70 Hz, 1H) 7.31 (td, J=7.85, 1.68 Hz, 1H) 7.35-7.45 (m, 2H) 7.83 (ddd, J=7.63, 4.96, 1.14 Hz, 1H) 7.96 (dd, J=8.92, 5.72 Hz, 1H) 8.06 (dd, J=8.24, 2.59 Hz, 1H) 8.80 (d, J=5.03 Hz, 1H) 10.29 (s, 1H).

The following compound was isolated in mixture with related boronic acid:

5-Bromo-thiophene-2-sulfonic acid [2-fluoro-3-(4,4,5,5-tetramethyl-[1,3,2]dioxaborolan-2-yl)-phenyl]-amide, compound of formula (VIII)

MS (ESI) for $C_{16}H_{18}BBrFNO_4S_2$ (MW: 462.17): [M+NH$_4$]$^+$ found 480.

Preparation 10

5-Chloro-2-fluoro-4-methoxy-benzenesulfonyl chloride, compound of formula (XI)

Scheme 1

1-Chloro-4-fluoro-2-methoxy-benzene

To 2-chloro-5-fluoro-phenol (959 mg, 6.54 mmol) in DMF (15 mL) at 0° C. was added 60% NaH (496 mg, 12.4 mmol) portionwise. After H$_2$ bubbling stopped, iodomethane (0.43 mL, 6.91 mmol) was added and the reaction mixture was allowed to warm at room temperature overnight. The reaction mixture was slowly poured onto water and crushed ice, basified with saturated aqueous NaHCO$_3$ and extracted with DCM. The combined organic phase was washed with brine, dried over Na$_2$SO$_4$ and evaporated under vacuum. The crude was purified by silica gel chromatography which was eluted with hexane:AcOEt=9:1 to give 1-chloro-4-fluoro-2-methoxy-benzene (600 mg) as transparent oil.

HPLC (254 nm): Rt: 6.15 min.

$^1$H NMR (600 MHz, DMSO-d6) delta ppm: 3.86 (s, 3H) 6.76-6.85 (m, 1H) 7.10 (dd, J=10.90, 2.84 Hz, 1H) 7.45 (dd, J=8.70, 6.14 Hz, 1H).

5-Chloro-2-fluoro-4-methoxy-benzenesulfonyl chloride, compound of formula (XI)

Scheme 1

To 1-chloro-4-fluoro-2-methoxy-benzene (355 mg, 2.21 mmol) in DCM (20 mL) at 0° C. was added chlorosulfonic acid (0.59 mL, 8.84 mmol) and stirred at room temperature overnight. The reaction was diluted with DCM, washed with water, brine, dried over Na$_2$SO$_4$ and evaporated under vacuum. The crude was purifed by silica gel chromatography which was eluted with hexane:AcOEt=8:2 to furnish the title compound (400 mg) as white solid.

$^1$H NMR (600 MHz, DMSO-d6) delta ppm: 3.86 (s, 3H) 7.02 (d, J=11.17 Hz, 1H) 7.59 (d, J=7.33 Hz, 1H).

Analogously the following compounds were obtained:

4,5-Dichloro-2-fluoro-benzenesulfonyl chloride, compound of formula (XI)

$^1$H NMR (500 MHz, DMSO-d6) delta ppm: 7.63 (d, J=9.00 Hz, 1H) 7.76 (d, J=6.71 Hz, 1H).

2-Fluoro-4-methoxy-5-methyl-benzenesulfonyl chloride, compound of formula (XI)

$^1$H NMR (500 MHz, DMSO-d6) delta ppm: 2.07 (s, 3H) 3.77 (s, 3H) 6.72 (d, J=11.90 Hz, 1H) 7.39 (d, J=8.54 Hz, 1H).

4-Chloro-2-fluoro-5-methoxy-benzenesulfonyl chloride, compound of formula (XI)

$^1$H NMR (500 MHz, DMSO-d6) delta ppm: 3.82 (s, 3H) 7.33 (d, J=6.10 Hz, 1H) 7.34 (d, J=8.85 Hz, 1H).

3-Cyano-4-methoxy-benzenesulfonyl chloride, compound of formula (XI)

$^1$H NMR (500 MHz, DMSO-d6) delta ppm: 3.92 (s, 3H) 7.21 (d, J=8.85 Hz, 1H) 7.76 (d, J=1.98 Hz, 1H) 7.84 (dd, J=8.69, 2.14 Hz, 1H).

3-Bromo-4-methoxy-benzenesulfonyl chloride, compound of formula (XI)

$^1$H NMR (500 MHz, DMSO-d6) delta ppm: 3.85 (s, 3H) 7.05 (d, J=8.54 Hz, 1H) 7.54 (dd, J=8.46, 2.06 Hz, 1H) 7.69 (d, J=1.98 Hz, 1H).

Preparation 11

N-(3-Bromo-2-cyano-phenyl)-5-chloro-2-fluoro-4-methoxy-benzenesulfonamide, compound of formula (XX)

To a solution of 2-amino-6-bromo-benzonitrile (501 mg, 2.47 mmol) in anhydrous DMF (20 mL) at 0° C. was added 60% NaH (176 mg, 4.4 mmol) portionwise. After 30 min, 2-Fluoro-4-methoxy-5-methyl-benzenesulfonyl chloride (703 mg, 2.72 mmol) was added and the reaction mixture was allowed to warm at room temperature. After 3 hours, the reaction was diluted with AcOEt, washed with saturated aqueous NH$_4$Cl, brine, dried over Na$_2$SO$_4$ and evaporated. The crude was purified by silica gel chromatography which was eluted with hexane:AcOEt=7:3. The resulting solid was triturated with hexane:Et$_2$O=1:1 to furnish the title compound (479 mg) as white solid.

HPLC (254 nm): Rt: 5.40 min.

HRMS (ESI) calcd for $C_{14}H_9BrClFN_2O_3S$ [M+Na]$^+$ 440.9082, found 440.9075.

1H NMR (500 MHz, DMSO-d6) delta ppm: 3.87 (s, 3H) 6.81 (br. s., 1H) 6.97-7.18 (m, 3H) 7.65-7.71 (m, 1H).

Preparation 12

4-Chloro-7-methyl-5-(4,4,5,5-tetramethyl-[1,3,2]dioxaborolan-2-yl)-7H-pyrrolo[2,3-d]pyrimidine, compound of formula(XVII)A Scheme 3, Step i1A To a solution of 4-chloro-5-iodo-7-methyl-7H-pyrrolo[2,3-d]pyrimidine (1.16 g, 3.96 mmol) in dry THF (50 mL) at −10° C. was slowly added i-prMgCl in THF (2.0N, 2.4 mL, 4.80 mmol). After 5 min 1-isopropoxy-3,3,4,4-tetramethyl-borolane (1.2 mL, 5.94 mmol) was added and stirred for 2 hours. The reaction was diluted with saturated aqueous $NH_4Cl$ and extracted with AcOEt. The combined organic phase was washed with brine, dried over $Na_2SO_4$ and evaporated. The crude was purified by silica gel chromatography which was eluted with hexane:AcOEt=7:3 to afford 4-Chloro-7-methyl-5-(4,4,5,5-tetramethyl-[1,3,2]dioxaborolan-2-yl)-7H-pyrrolo[2,3-d]pyrimidine (850 mg) as white solid.

HPLC (254 nm): Rt: 5.99 min.

HRMS (ESI) calcd for $C_{13}H_{17}BClN_3O_2$ [M+H]$^+$ 293.1212, found 293.1221.

1H NMR (500 MHz, DMSO-d6) delta ppm: 1.30 (s, 12H) 3.84 (s, 3H) 8.04 (s, 1H) 8.65 (s, 1H).

EXAMPLE 1

N-[3-(4-Amino-7-methyl-7H-pyrrolo[2,3-d]pyrimidin-5-yl)-2-fluoro-phenyl]-3-chloro-4-methoxy-benzenesulfonamide, compound of formula (I), (cmpd 1)

Scheme 1

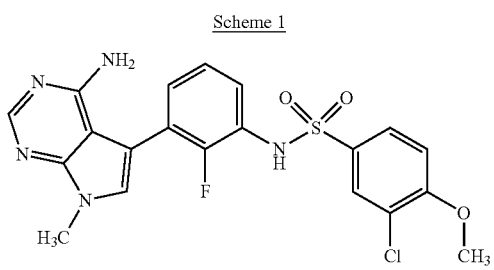 [SMILES: COc1ccc(S(=O)(=O)Nc2cccc(-c3cn(C)c4ncnc(N)c34)c2F)cc1Cl]

N-[3-(4-Amino-7-methyl-7H-pyrrolo[2,3-d]pyrimidin-5-yl)-2-fluoro-phenyl]-3-chloro-4-methoxy-N-methoxymethyl-benzenesulfonamide, compound of formula (X)

Scheme 1, Step d

In a Schlenk tube, to 5-iodo-7-methyl-7H-pyrrolo[2,3-d]pyrimidin-4-ylamine (88 mg, 0.321 mmol), 3-chloro-N-[2-fluoro-3-(4,4,5,5-tetramethyl-[1,3,2]dioxaborolan-2-yl)-phenyl]-4-methoxy-N-methoxymethyl-benzenesulfonamide (244 mg, 0.503 mmol), $Cs_2CO_3$ (308 mg, 0.945 mmol) and 1,1'-bis(diphenylphosphino)ferrocene] dichloropalladium (II), complex with dichloromethane (1:1) (21 mg, 0.026 mmol) were added 1,2-dimethoxyethane (DME) (5 mL) and water (0.55 mL). The reaction mixture was degassed with nitrogen, heated to 85° C. for 5 hours and then filtered through a celite pad. The filtrate was evaporated under reduced pressure; the crude was taken up with DCM, washed with saturated aqueous $NaHCO_3$, brine and dried over $Na_2SO_4$. The organic was evaporated and the crude purified by crystallization with AcOEt to furnish the title compound (72 mg) as white solid. MS (ESI) for $C_{22}H_{21}ClFN_5O_4S$ (MW:505.96): [M+H]$^+$ found 506

Analogously the following compound was obtained:

N-[3-(4-Amino-7-isopropyl-7H-pyrrolo[2,3-d]pyrimidin-5-yl)-2-fluoro-phenyl]-3-chloro-4-methoxy-N-methoxymethyl-benzenesulfonamide, compound of formula (X)

MS (ESI) for $C_{24}H_{25}ClFN_5O_4S$ (MW:534.01): [M+H]$^+$ found 535.

N-[3-(4-Amino-7-methyl-7H-pyrrolo[2,3-d]pyrimidin-5-yl)-2-fluoro-phenyl]-3-chloro-4-methoxy-benzenesulfonamide, compound of formula (I) (cmpd 1)

Scheme 1, Step g

To a solution of N-[3-(4-amino-7-methyl-7H-pyrrolo[2,3-d]pyrimidin-5-yl)-2-fluoro-phenyl]-3-chloro-4-methoxy-N-methoxymethyl-benzenesulfonamide (50.5 mg, 0.100 mmol) in trifluoroacetic acid (TFA) (1 mL) was added water (0.15 mL) and heated to 50° C. for 5 hours. The reaction mixture was poured into a saturated aqueous $NaHCO_3$ and extracted with DCM. The combined organic phase was washed with brine, dried over $Na_2SO_4$ and evaporated under reduce pressure. The crude was purified by preparative HPLC to give the title compound (20 mg) as a white solid.

HPLC (254 nm): Rt: 7.59 min.

HRMS (ESI) calcd for $C_{20}H_{17}ClFN_5O_3S$ [M+H]$^+$ 462.0798, found 462.0789.

$^1$H NMR (401 MHz, DMSO-d6) delta ppm: 3.73 (s, 3H) 3.91 (s, 3H) 5.96 (br. s., 2H) 6.98-7.10 (m, 1H) 7.10-7.20 (m, 2H) 7.22 (s, 1H) 7.28 (d, J=8.79 Hz, 1H) 7.68 (dd, J=8.67, 2.32 Hz, 1H) 7.75 (d, J=2.32 Hz, 1H) 8.14 (s, 1H).

Analogously the following compound was obtained:

N-[3-(4-Amino-7-isopropyl-7H-pyrrolo[2,3-d]pyrimidin-5-yl)-2-fluoro-phenyl]-3-chloro-4-methoxy-benzenesulfonamide, compound of formula (I), (cmpd 2)

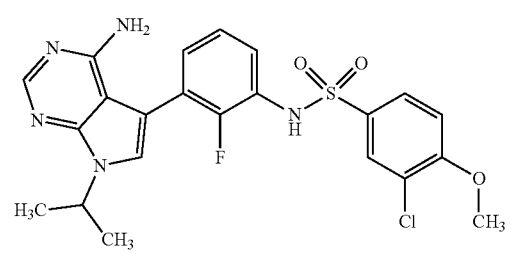 [SMILES: COc1ccc(S(=O)(=O)Nc2cccc(-c3cn(C(C)C)c4ncnc(N)c34)c2F)cc1Cl]

HPLC (254 nm): Rt: 5.89 min.

HRMS (ESI) calcd for $C_{22}H_{21}ClFN_5O_3S$ [M+H]$^+$ 490.1111, found 490.1114.

$^1$H NMR (401 MHz, DMSO-d6) delta ppm 1.44 (d, J=6.71 Hz, 6H) 3.92 (s, 3H) 4.95 (spt, J=6.71 Hz, 1H) 5.95 (br. s., 2H) 7.20 (d, J=3.66 Hz, 3H) 7.28-7.36 (m, 2H) 7.69 (dd, J=8.67, 2.32 Hz, 1H) 7.75 (d, J=2.32 Hz, 1H) 8.13 (s, 1H) 10.18 (br. s., 1H).

N-[3-(4-Amino-7-methyl-7H-pyrrolo[2,3-d]pyrimidin-5-yl)-2-fluoro-phenyl]-3-chloro-4-hydroxy-benzenesulfonamide, compound of formula (I), (cmpd 67)

Scheme 1, Step g

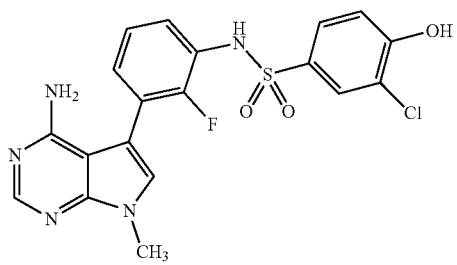 [SMILES: Cn1cc(-c2cccc(NS(=O)(=O)c3ccc(O)c(Cl)c3)c2F)c2c(N)ncnc21]

N-[3-(4-Amino-7-methyl-7H-pyrrolo[2,3-d]pyrimidin-5-yl)-2-fluoro-phenyl]-3-chloro-4-methoxy-N-ethoxymethyl-benzenesulfonamide (9.3 mg, 0.018 mmol) in DCM (3 mL) was treated with a solution of BBr$_3$ in DCM 1M (144 microL, 0.144 mmol) at room temperature overnight. The reaction was quenched with MeOH and evaporated under vacuum. The crude was purified by silica gel chromatography which was eluted with DCM:MeOH=95:5 to furnish the title compound (6.4 mg) as white solid.

HPLC (254 nm): Rt: 4.94 min.

HRMS (ESI) calcd for $C_{19}H_{15}ClFN_5O_3S$ [M+H]$^+$ 448.0641, found 448.0636.

1H NMR (401 MHz, DMSO-d6) delta ppm: 3.73 (s, 3H) 5.96 (br. s., 2H) 7.07 (d, J=8.67 Hz, 1H) 7.12-7.28 (m, 4H) 7.53 (dd, J=8.67, 2.32 Hz, 1H) 7.69 (d, J=2.20 Hz, 1H) 8.15 (s, 1H) 10.09 (br. s., 1H) 11.32 (br. s., 1H).

EXAMPLE 2

N-{3-[4-Amino-7-(1-methyl-piperidin-4-yl)-7H-pyrrolo[2,3-d]pyrimidin-5-yl]-2-fluoro-phenyl}-5-chloro-2-fluoro-4-methoxy-benzenesulfonamide, compound of formula (I), (cmpd 3)

Scheme 1, Step c

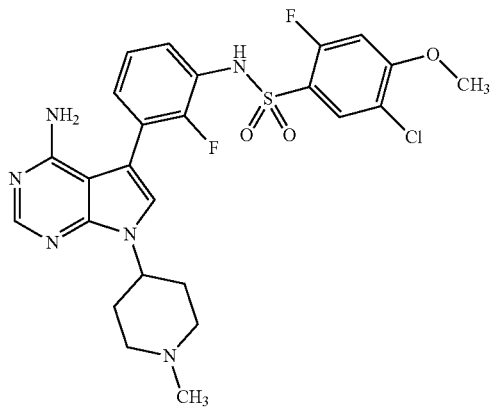 [SMILES: COc1cc(F)c(S(=O)(=O)Nc2cccc(-c3cn(C4CCN(C)CC4)c4ncnc(N)c34)c2F)cc1Cl]

In a Schlenk tube, to 5-iodo-7-(1-methyl-piperidin-4-yl)-7H-pyrrolo[2,3-d]pyrimidin-4-ylamine (36 mg, 0.102 mmol), 5-chloro-N-[2-chloro-3-(4,4,5,5-tetramethyl-[1,3,2]dioxaborolan-2-yl)-phenyl]-2-fluoro-4-methoxy-benzenesulfonamide (90 mg, 0.196 mmol), Cs$_2$CO$_3$ (119 mg, 0.365 mmol) and 1,1'-bis(diphenylphosphino)ferrocene]dichloropalladium(II), complex with dichloromethane (1:1) (6.7 mg, 0.008 mmol) were added 1,2-dimethoxyethane (DME) (1.8 mL) and water (0.2 mL). The reaction mixture was degassed with nitrogen, heated to 85° C. for 5 hours and then filtered through a celite pad. The filtrate was evaporated under reduced pressure; the crude was taken up with DCM, washed with saturated aqueous NaHCO$_3$, brine and dried over Na$_2$SO$_4$. The organic was evaporated and the crude purified by silica gel chromatography which was eluted with DCM:MeOH:NH$_3$=90:10:0.5% to furnish the title compound (33 mg) as white solid.

HPLC (254 nm): Rt: 4.85 min.

HRMS (ESI) calcd for $C_{25}H_{25}ClF_2N_6O_3S$ [M+H]$^+$ 563.1438, found 563.1445.

$^1$H NMR (401 MHz, DMSO-d6) delta ppm: 1.93 (m, J=12.69, 2.56 Hz, 2H) 2.02-2.16 (m, 2H) 2.27 (m, J=11.41, 11.41 Hz, 2H) 2.33 (s, 3H) 3.00 (m, J=11.35 Hz, 2H) 3.93 (s, 3H) 4.58 (tt, J=11.89, 4.10 Hz, 1H) 5.98 (br. s., 2H) 7.01-7.25 (m, 3H) 7.32 (t, J=5.92 Hz, 2H) 7.70 (d, J=7.32 Hz, 1H) 8.13 (s, 1H) 10.37 (s, 1H).

Analogously the following compounds were obtained:

N-{3-[4-Amino-7-(1-methyl-piperidin-4-yl)-7H-pyrrolo[2,3-d]pyrimidin-5-yl]-2-fluoro-phenyl}-3-chloro-4-methoxy-benzenesulfonamide, compound of formula (I), (cmpd 4)

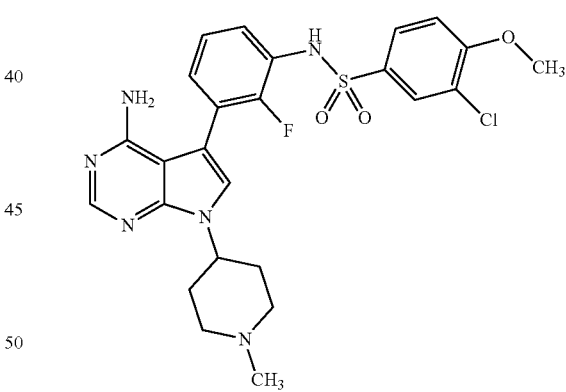

HPLC (254 nm): Rt: 4.74 min.

HRMS (ESI) calcd for $C_{25}H_{26}ClFN_6O_3S$ [M+H]$^+$ 545.1533, found 545.1547.

$^1$H NMR (401 MHz, DMSO-d6) delta ppm: 1.89 (m, J=9.52 Hz, 2H) 1.98-2.11 (m, 2H) 2.11-2.21 (m, 2H) 2.27 (s, 3H) 2.94 (m, J=11.11 Hz, 2H) 3.92 (s, 3H) 4.42-4.67 (m, 1H) 5.97 (br. s., 2H) 7.10-7.24 (m, 3H) 7.27-7.34 (m, 2H) 7.69 (dd, J=8.67, 2.32 Hz, 1H) 7.74 (d, J=2.32 Hz, 1H) 8.12 (s, 1H) 9.52-10.46 (m, 1H).

N-{3-[4-Amino-7-(1-cyclopropyl-piperidin-4-yl)-7H-pyrrolo[2,3-d]pyrimidin-5-yl]-2-fluoro-phenyl}-3-chloro-4-methoxy-benzenesulfonamide, compound of formula (I), (cmpd 5)

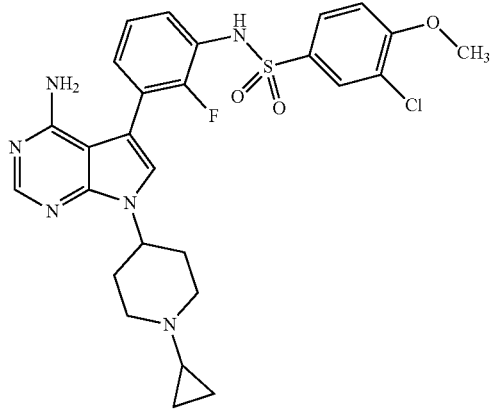 [SMILES: COc1ccc(S(=O)(=O)Nc2cccc(-c3cn(C4CCN(C5CC5)CC4)c4ncnc(N)c34)c2F)cc1Cl]

HPLC (254 nm): Rt: 5.69 min.
HRMS (ESI) calcd for $C_{27}H_{28}ClFN_6O_3S$ $[M+H]^+$ 571.1689, found 571.1685.
$^1$H NMR (500 MHz, DMSO-d6) delta ppm: 0.42-1.04 (m, 4H) 2.07 (s, 3H) 2.54 (br. s., 4H) 3.92 (s, 3H) 4.65-4.82 (m, 1H) 6.09 (br. s., 2H) 7.13-7.23 (m, 3H) 7.28 (br. s., 1H) 7.31 (d, J=8.85 Hz, 1H) 7.71 (dd, J=8.77, 2.21 Hz, 1H) 7.76 (d, J=2.29 Hz, 1H) 8.15 (s, 2H) 10.23 (br. s., 1H).

N-{3-[4-Amino-7-(1-isopropyl-piperidin-4-yl)-7H-pyrrolo[2,3-d]pyrimidin-5-yl]-2-fluoro-phenyl}-3-chloro-4-methoxy-benzenesulfonamide, compound of formula (I), (cmpd 6)

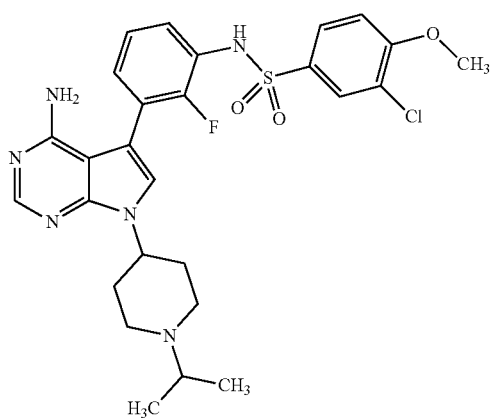 [SMILES: COc1ccc(S(=O)(=O)Nc2cccc(-c3cn(C4CCN(C(C)C)CC4)c4ncnc(N)c34)c2F)cc1Cl]

HPLC (254 nm): Rt: 4.93 min.
HRMS (ESI) calcd for $C_{27}H_{30}ClFN_6O_3S$ $[M+H]^+$ 573.1846, found 573.1859.
$^1$H NMR (500 MHz, DMSO-d6) delta ppm: 1.03 (d, J=6.56 Hz, 6H) 1.82-2.10 (m, 4H) 2.38 (d, J=14.18 Hz, 2H) 2.84 (br. s., 1H) 2.97 (m, J=9.61 Hz, 2H) 3.92 (s, 3H) 4.48-4.61 (m, 1H) 5.63-6.34 (m, 2H) 7.05-7.23 (m, 3H) 7.27-7.35 (m, 2H) 7.69 (dd, J=8.92, 2.06 Hz, 1H) 7.74 (d, J=2.14 Hz, 1H) 8.10-8.17 (m, 1H) 9.69-10.45 (m, 1H).

N-[3-(4-Amino-7-methyl-7H-pyrrolo[2,3-d]pyrimidin-5-yl)-2-chloro-phenyl]-5-chloro-2-fluoro-4-methoxy-benzenesulfonamide, compound of formula (I), (cmpd 7)

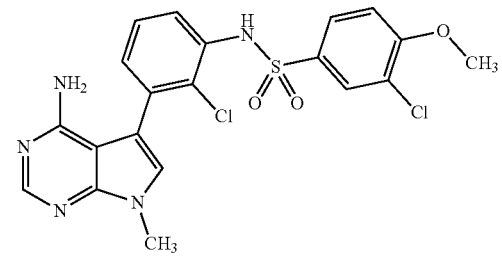 [SMILES: COc1ccc(S(=O)(=O)Nc2cccc(-c3cn(C)c4ncnc(N)c34)c2Cl)cc1Cl]

HPLC (254 nm): Rt: 5.70 min.
HRMS (ESI) calcd for $C_{20}H_{16}Cl_2FN_5O_3S$ $[M+H]^+$ 496.0408, found 496.0417.
$^1$H NMR (500 MHz, DMSO-d6) delta ppm: 3.72 (s, 3H) 3.94 (s, 3H) 5.79 (br. s., 2H) 7.23 (s, 1H) 7.25-7.45 (m, 4H) 7.70 (d, J=7.32 Hz, 1H) 8.14 (s, 1H) 10.37 (br. s., 1H).

N-[3-(4-Amino-7-methyl-7H-pyrrolo[2,3-d]pyrimidin-5-yl)-2-chloro-phenyl]-3-chloro-4-methoxy-benzenesulfonamide, compound of formula (I), (cmpd 8)

HPLC (254 nm): Rt: 5.55 min.
HRMS (ESI) calcd for $C_{20}H_{17}Cl_2N_5O_3S$ $[M+H]^+$ 478.0502, found 478.05.
$^1$H NMR (500 MHz, DMSO-d6) delta ppm: 3.72 (s, 3H) 3.93 (s, 3H) 5.28-6.34 (m, 2H) 7.21 (s, 1H) 7.24 (d, J=7.47 Hz, 2H) 7.31 (d, J=8.85 Hz, 1H) 7.33-7.39 (m, 1H) 7.67 (dd, J=8.85, 2.29 Hz, 1H) 7.79 (d, J=2.29 Hz, 1H) 8.13 (s, 1H) 10.04 (s, 1H).

47

N-[3-(4-Amino-1-methyl-1H-pyrazolo[3,4-d]pyrimidin-3-yl)-2-fluoro-phenyl]-5-chloro-2-fluoro-4-methoxy-benzenesulfonamide, compound of formula (I), (cmpd 9)

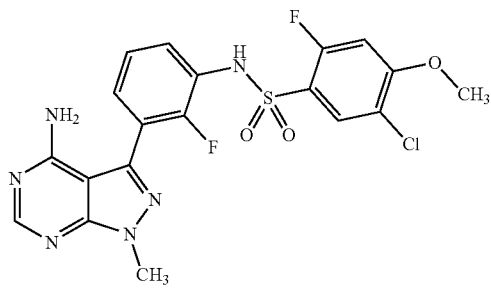

HPLC (254 nm): Rt: 5.34 min.

HRMS (ESI) calcd for $C_{19}H_{15}ClF_2N_6O_3S$ [M+H]$^+$ 481.0656, found 481.064.

$^1$H NMR (500 MHz, DMSO-d6) delta ppm: 3.93 (s, 3H) 3.94 (s, 3H) 7.23-7.32 (m, 1H) 7.33-7.41 (m, 3H) 7.73 (d, J=7.32 Hz, 1H) 8.25 (s, 1H) 10.59 (s, 1H).

4-{4-Amino-3-[3-(5-chloro-2-fluoro-4-methoxy-benzenesulfonylamino)-2-fluoro-phenyl]-pyrazolo[3,4-d]pyrimidin-1-yl}-piperidine-1-carboxylic acid tert-butyl ester, compound of formula (I), (cmpd 10)

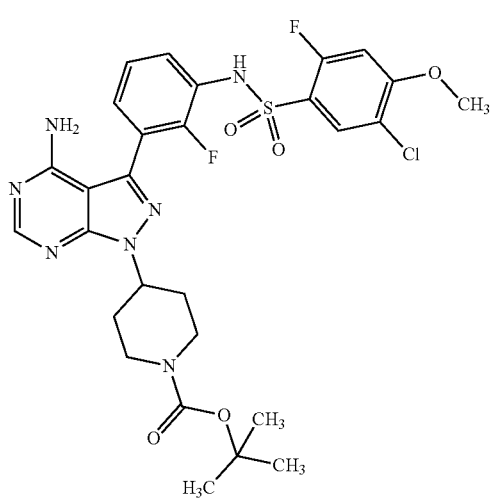 [SMILES: COc1cc(F)c(S(=O)(=O)Nc2cccc(-c3nn(C4CCN(C(=O)OC(C)(C)C)CC4)c4ncnc(N)c34)c2F)cc1Cl]

HPLC (254 nm): Rt: 6.64 min.

HRMS (ESI) calcd for $C_{28}H_{30}ClF_2N_7O_5S$ [M+H]$^+$ 650.1759, found 650.179.

$^1$H NMR (401 MHz, DMSO-d6) delta ppm: 1.42 (s, 9H) 1.83-2.05 (m, 4H) 3.00 (br. s., 2H) 3.93 (s, 3H) 4.08 (m, J=13.55 Hz, 2H) 4.89 (tt, J=10.42, 5.14 Hz, 1H) 7.23-7.42 (m, 4H) 7.73 (d, J=7.45 Hz, 1H) 8.24 (s, 1H) 10.56 (s, 1H).

48

4-{4-Amino-3-[3-(3-chloro-4-methoxy-benzenesulfonylamino)-2-fluoro-phenyl]-pyrazolo[3,4-d]pyrimidin-1-yl}-piperidine-1-carboxylic acid tert-butyl ester, compound of formula (I), (cmpd 11)

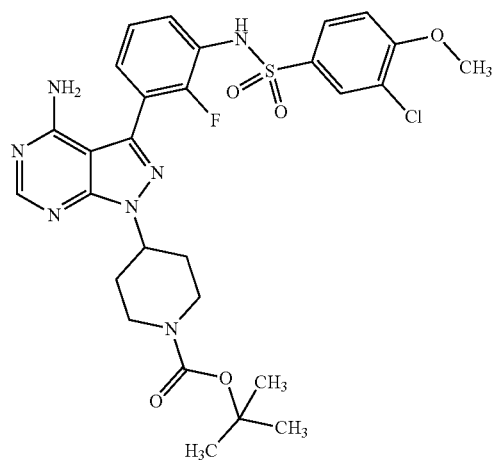 [SMILES: COc1ccc(S(=O)(=O)Nc2cccc(-c3nn(C4CCN(C(=O)OC(C)(C)C)CC4)c4ncnc(N)c34)c2F)cc1Cl]

HPLC (254 nm): Rt: 6.53 min.

HRMS (ESI) calcd for $C_{28}H_{31}ClFN_7O_5S$ [M+H]$^+$ 632.1853, found 632.184.

$^1$H NMR (401 MHz, DMSO-d6) delta ppm: 1.42 (s, 9H) 1.77-2.04 (m, 4H) 2.98 (br. s., 2H) 3.92 (s, 3H) 4.07 (m, J=12.45 Hz, 2H) 4.89 (m, J=10.44, 5.40, 5.40 Hz, 1H) 7.21-7.37 (m, 4H) 7.71 (dd, J=8.79, 2.32 Hz, 1H) 7.80 (d, J=2.20 Hz, 1H) 8.23 (s, 1H) 10.24 (s, 1H).

N-[3-(4-Amino-furo[3,2-c]pyridin-3-yl)-2-fluoro-phenyl]-5-chloro-2-fluoro-4-methoxy-benzenesulfonamide, compound of formula (I) (cmpd 69)

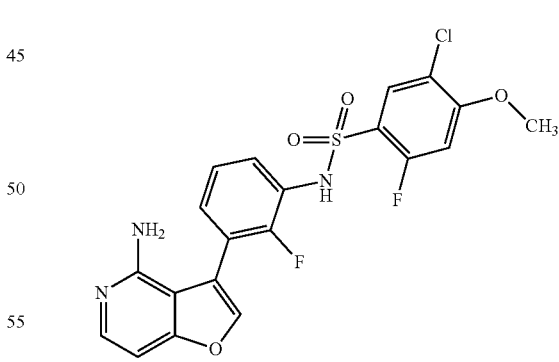

HPLC (254 nm): Rt: 6.01 min.

HRMS (ESI) calcd for $C_{20}H_{14}ClF_2N_3O_4S$ [M+H]$^+$ 466.0435, found 466.0424.

$^1$H NMR (500 MHz, DMSO-d6) delta ppm: 3.94 (s, 3H) 5.42 (s, 2H) 6.95 (d, J=5.95 Hz, 1H) 7.22-7.41 (m, 4H) 7.73 (d, J=7.47 Hz, 1H) 7.87 (d, J=5.95 Hz, 1H) 7.94 (s, 1H) 10.62 (br. s., 1H).

N-[3-(4-Amino-furo[3,2-c]pyridin-3-yl)-2-fluoro-phenyl]-3-chloro-4-methoxy-benzenesulfonamide, compound of formula (I) (cmpd 70)

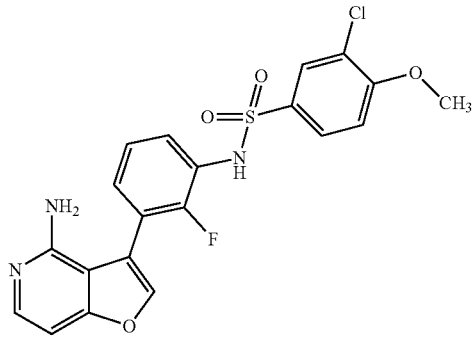 [SMILES: COc1ccc(S(=O)(=O)Nc2cccc(-c3coc4ccnc(N)c34)c2F)cc1Cl]

HPLC (254 nm): Rt: 5.83 min.

HRMS (ESI) calcd for $C_{20}H_{15}ClFN_3O_4S$ $[M+H]^+$ 448.0529, found 448.0519.

$^1$H NMR (500 MHz, DMSO-d6) delta ppm: 3.92 (s, 3H) 5.40 (s, 2H) 6.95 (d, J=5.95 Hz, 1H) 7.20-7.35 (m, 4H) 7.68 (dd, J=8.69, 2.29 Hz, 1H) 7.78 (d, J=2.29 Hz, 1H) 7.87 (d, J=5.95 Hz, 1H) 7.92 (s, 1H) 10.31 (br. s., 1H).

N-{3-[4-Amino-7-(1-methyl-piperidin-4-yl)-7H-pyrrolo[2,3-d]pyrimidin-5-yl]-2-fluoro-phenyl}-3,4-dichloro-benzenesulfonamide, compound of formula (I) (cmpd 71)

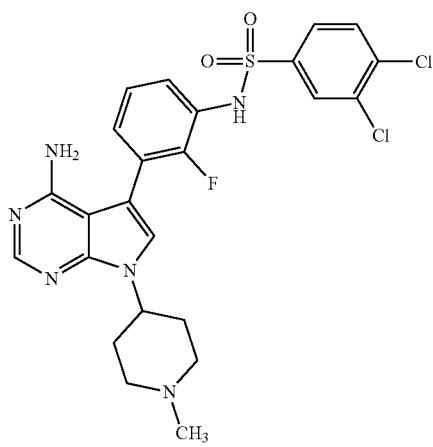 [SMILES: CN1CCC(n2cc(-c3cccc(NS(=O)(=O)c4ccc(Cl)c(Cl)c4)c3F)c3c(N)ncnc32)CC1]

HPLC (254 nm): Rt: 5.18 min.

HRMS (ESI) calcd for $C_{24}H_{23}Cl_2FN_6O_2S$ $[M+H]^+$ 549.1037, found 549.1042.

$^1$H NMR (500 MHz, DMSO-d6) delta ppm: 1.95 (d, J=11.29 Hz, 2H) 2.11 (qd, J=12.70, 3.00 Hz, 2H) 2.37 (br. s, 5H) 3.06 (d, J=10.68 Hz, 2H) 4.60 (tt, J=11.84, 4.02 Hz, 1H) 6.03 (br. s., 1H) 7.08 (t, J=6.70 Hz, 1H) 7.13 (t, J=7.78 Hz, 1H) 7.17 (td, J=7.50, 1.70 Hz, 1H) 7.31 (s, 1H) 7.69 (dd, J=8.39, 2.14 Hz, 1H) 7.83 (d, J=8.39 Hz, 1H) 7.91 (d, J=2.13 Hz, 1H) 8.13 (s, 1H).

N-{3-[4-Amino-7-(1-methyl-piperidin-4-yl)-7H-pyrrolo[2,3-d]pyrimidin-5-yl]-2-fluoro-phenyl}-4-bromo-2-fluoro-benzenesulfonamide, compound of formula (I) (cmpd 72)

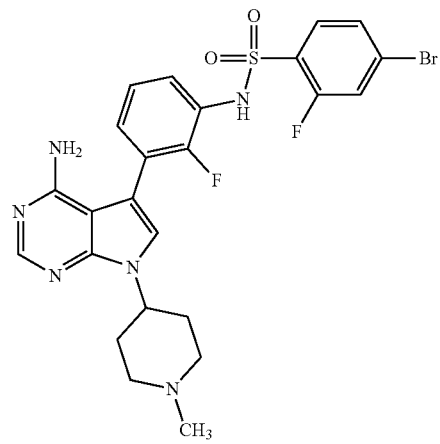 [SMILES: CN1CCC(n2cc(-c3cccc(NS(=O)(=O)c4ccc(Br)cc4F)c3F)c3c(N)ncnc32)CC1]

HPLC (254 nm): Rt: 4.88 min.

HRMS (ESI) calcd for $C_{24}H_{23}BrF_2N_6O_2S$ $[M+H]^+$ 577.0828, found 577.0836.

$^1$H NMR (500 MHz, DMSO-d6) delta ppm: 1.95 (d, J=10.83 Hz, 2H) 2.12 (qd, J=12.20, 3.05 Hz, 2H) 2.37 (br. s, 5H) 3.06 (d, J=10.83 Hz, 2H) 4.60 (t, J=11.90 Hz, 1H) 5.98 (br. s, 2H) 7.06 (br. s., 1H) 7.11 (t, J=7.85 Hz, 1H) 7.19 (td, J=7.66, 1.60 Hz, 1H) 7.32 (s, 1H) 7.55 (dd, J=8.39, 1.68 Hz, 1H) 7.69 (t, J=8.08 Hz, 1H) 7.80 (d, J=9.15 Hz, 1H) 8.13 (s, 1H).

N-{3-[4-Amino-7-(1-methyl-piperidin-4-yl)-7H-pyrrolo[2,3-d]pyrimidin-5-yl]-2-fluoro-phenyl}-2-fluoro-4-methoxy-5-methyl-benzenesulfonamide, compound of formula (I) (cmpd 73)

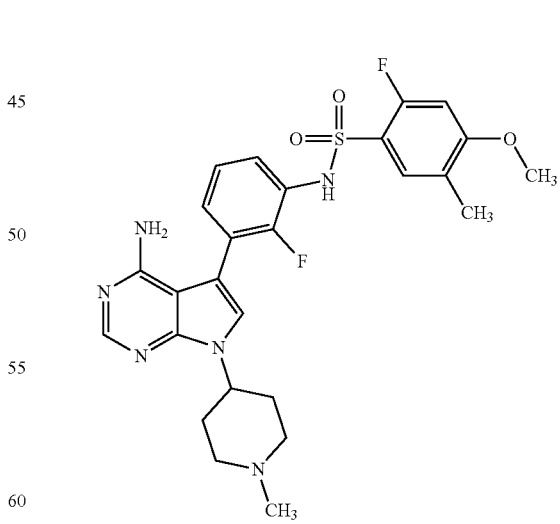

HPLC (254 nm): Rt: 4.97 min.

HRMS (ESI) calcd for $C_{26}H_{28}F_2N_6O_3S$ $[M+H]^+$ 543.1985, found 543.1978.

$^1$H NMR (500 MHz, DMSO-d6) delta ppm: 1.88 (d, J=11.74 Hz, 2H) 2.05 (qd, J=12.10, 3.20 Hz, 2H) 2.10 (s, 3H) 2.13 (t, J=11.50 Hz, 2H) 2.25 (s, 3H) 2.93 (d, J=11.13 Hz, 2H) 3.85 (s, 3H) 4.54 (tt, J=11.61, 4.18 Hz, 1H) 5.98 (br. s., 2H) 7.07 (d, J=12.51 Hz, 1H) 7.13-7.19 (m, 2H) 7.19-7.26 (m, 1H) 7.33 (s, 1H) 7.51 (d, J=8.24 Hz, 1H) 8.13 (s, 1H) 10.30 (br. s., 1H).

N-[3-(4-Amino-7-isopropyl-7H-pyrrolo[2,3-d]pyrimidin-5-yl)-2-fluoro-phenyl]-5-chloro-2-fluoro-4-methoxy-benzenesulfonamide, compound of formula (I) (cmpd 74)

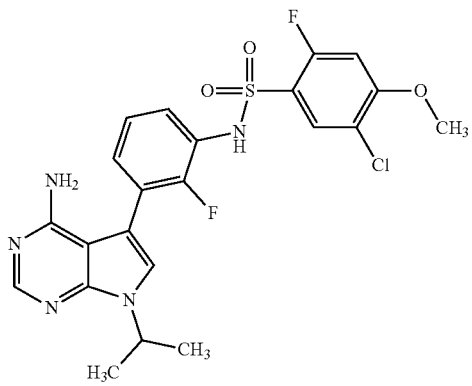 [SMILES: COc1cc(F)c(S(=O)(=O)Nc2cccc(-c3cn(C(C)C)c4ncnc(N)c34)c2F)cc1Cl]

HPLC (254 nm): Rt: 5.98 min.

HRMS (ESI) calcd for $C_{22}H_{20}ClF_2N_5O_3S$ [M+H]$^+$ 508.1016, found 508.1014.

$^1$H NMR (500 MHz, DMSO-d6) delta ppm: 1.44 (d, J=6.86 Hz, 6H) 3.94 (s, 3H) 4.95 (spt, J=6.81 Hz, 1H) 5.99 (br. s., 2H) 7.16-7.31 (m, 3H) 7.35 (s, 1H) 7.38 (d, J=12.05 Hz, 1H) 7.71 (d, J=7.32 Hz, 1H) 8.13 (s, 1H) 10.52 (s, 1H).

N-[3-(4-Amino-7-ethyl-7H-pyrrolo[2,3-d]pyrimidin-5-yl)-2-fluoro-phenyl]-5-chloro-2-fluoro-4-methoxy-benzenesulfonamide, compound of formula (I) (cmpd 75)

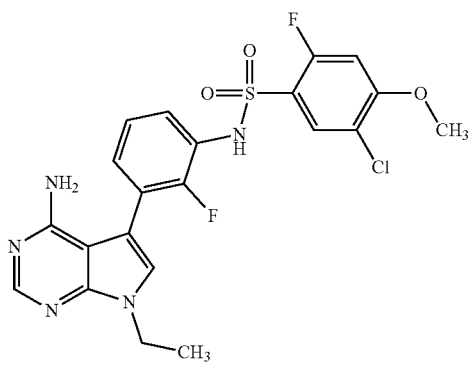 [SMILES: CCn1cc(-c2cccc(NS(=O)(=O)c3cc(Cl)c(OC)cc3F)c2F)c2c(N)ncnc21]

HPLC (254 nm): Rt: 8.66 min.

HRMS (ESI) calcd for $C_{21}H_{18}ClF_2N_5O_3S$ [M+H]$^+$ 494.086, found 494.0859.

$^1$H NMR (500 MHz, DMSO-d6) delta ppm: 1.36 (t, J=7.24 Hz, 3H) 3.94 (s, 3H) 4.19 (q, J=7.17 Hz, 2H) 6.00 (br. s., 2H) 7.17-7.28 (m, 3H) 7.31 (s, 1H) 7.38 (d, J=11.90 Hz, 1H) 7.71 (d, J=7.47 Hz, 1H) 8.14 (s, 1H) 10.53 (br. s., 1H).

N-{3-[4-Amino-7-(tetrahydro-pyran-4-yl)-7H-pyrrolo[2,3-d]pyrimidin-5-yl]-2-fluoro-phenyl}-5-chloro-2-fluoro-4-methoxy-benzenesulfonamide, compound of formula (I) (cmpd 76)

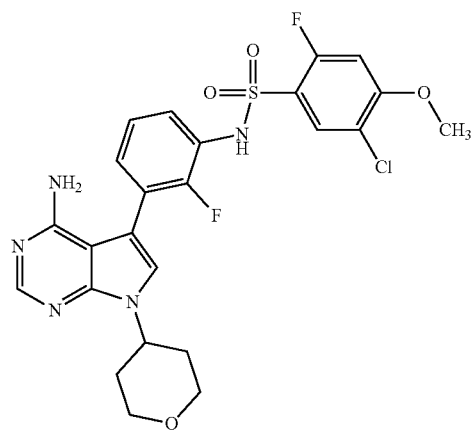 [SMILES: COc1cc(F)c(S(=O)(=O)Nc2cccc(-c3cn(C4CCOCC4)c4ncnc(N)c34)c2F)cc1Cl]

HPLC (254 nm): Rt: 5.68 min.

HRMS (ESI) calcd for $C_{24}H_{22}ClF_2N_5O_4S$ [M+H]$^+$ 550.1122, found 550.1123. $^1$H NMR (500 MHz, DMSO-d6) delta ppm: 1.87 (dd, J=12.20, 2.59 Hz, 2H) 1.99-2.14 (m, 2H) 3.47-3.59 (m, 2H) 3.94 (s, 3H) 3.99 (dd, J=11.21, 4.19 Hz, 2H) 4.82 (tt, J=11.93, 4.08 Hz, 1H) 6.02 (br. s., 1H) 7.17-7.30 (m, 3H) 7.38 (s, 1H) 7.38 (d, J=11.90 Hz, 1H) 7.71 (d, J=7.32 Hz, 1H) 8.14 (s, 1H) 10.53 (s, 1H).

The following compound was isolated as TFA salt by preparative HPLC:

5-Bromo-thiophene-2-sulfonic acid {3-[4-amino-7-(1-methyl-piperidin-4-yl)-7H-pyrrolo[2,3-d]pyrimidin-5-yl]-2-fluoro-phenyl}-amide, compound of formula (I) (cmpd 77)

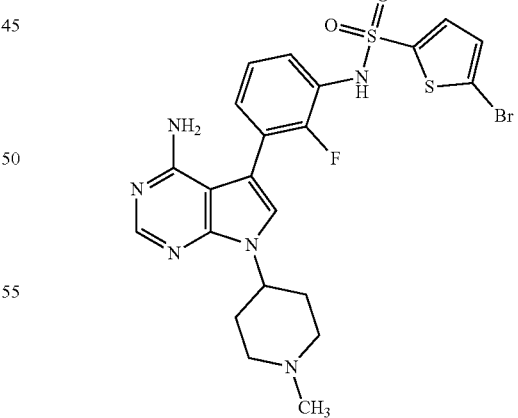

HPLC (254 nm): Rt: 4.8 min.

HRMS (ESI) calcd for $C_{22}H_{22}BrFN_6O_2S_2$ [M+H]$^+$ 565.0486, found 565.0497.

$^1$H NMR (500 MHz, DMSO-d6) delta ppm: 2.17-2.26 (m, 2H) 2.26-2.37 (m, 2H) 2.83 (br. s., 3H) 4.86 (tt, J=11.82, 4.19 Hz, 1H) 6.88 (br. s, 2H) 7.24-7.33 (m, 3H) 7.35 (d, J=4.12 Hz, 1H) 7.42 (d, J=4.12 Hz, 1H) 7.44 (s, 1H) 8.29 (s, 1H) 9.57 (br. s., 1H) 10.60 (br. s., 1H).

EXAMPLE 3

N-[3-(4-Amino-7-methyl-7H-pyrrolo[2,3-d]pyrimidin-5-yl)-2-fluoro-phenyl]-4-methoxy-3-methyl-benzenesulfonamide, compound of formula (I), (cmpd 12)

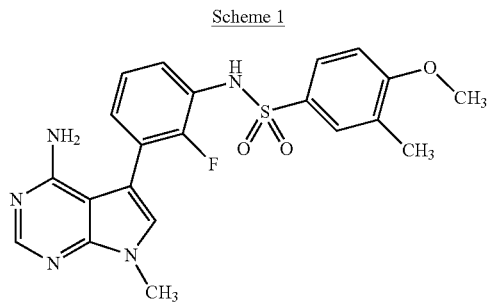 [SMILES: COc1ccc(S(=O)(=O)Nc2cccc(-c3cn(C)c4ncnc(N)c34)c2F)cc1C]

Scheme 1

[3-(4-Amino-7-methyl-7H-pyrrolo[2,3-d]pyrimidin-5-yl)-2-fluoro-phenyl]-carbamic acid tert-butyl ester, compound of formula (V)

Scheme 1, Step a

In a Schlenk tube, to 5-iodo-7-methyl-7H-pyrrolo[2,3-d]pyrimidin-4-ylamine (395 mg, 1.442 mmol), [2-fluoro-3-(4,4,5,5-tetramethyl-[1,3,2]dioxaborolan-2-yl)-phenyl]-carbamic acid tert-butyl ester (790 mg, 2.344 mmol), $Cs_2CO_3$ (1.42 g, 4.356 mmol) and 1,1'-bis(diphenylphosphino)ferrocene]dichloropalladium(II), complex with dichloromethane (1:1) (86.3 mg, 0.106 mmol) were added 1,2-dimethoxyethane (DME) (22.5 mL) and water (2.5 mL). The reaction mixture was degassed with nitrogen, heated to 85° C. for 5 hours and then filtered through a celite pad. The filtrate was evaporated under reduced pressure; the crude was taken up with DCM, washed with saturated aqueous $NaHCO_3$, brine and dried over $Na_2SO_4$. The solvent was evaporated and the crude was purified by silica gel chromatography which was eluted AcOEt to furnish the title compound (247 mg) as white solid.

HPLC (254 nm): Rt: 7.63 min.

HRMS (ESI) calcd for $C_{18}H_{20}FN_5O_2$ [M+H]$^+$ 358.1674, found 358.1667.

$^1$H NMR (500 MHz, DMSO-d6) delta ppm: 1.47 (s, 9H) 3.75 (s, 3H) 5.51-6.34 (m, 2H) 7.06-7.15 (m, 1H) 7.20 (t, J=7.85 Hz, 1H) 7.32 (s, 1H) 7.58 (t, J=7.17 Hz, 1H) 8.15 (s, 1H) 9.05 (s, 1H).

Analogously the following compound was obtained:

[3-(4-Amino-1-methyl-1H-pyrazolo[3,4-d]pyrimidin-3-yl)-2-fluoro-phenyl]-carbamic acid tert-butyl ester, compound of formula (V)

HPLC (254 nm): Rt: 5.29 min.

HRMS (ESI) calcd for $C_{17}H_{19}FN_6O_2$ [M+H]$^+$ 359.1627, found 359.1631.

$^1$H NMR (401 MHz, DMSO-d6) delta ppm: 1.48 (s, 9H) 3.96 (s, 3H) 6.98-7.36 (m, 2H) 7.61-7.82 (m, 1H) 8.25 (s, 1H) 9.09 (s, 1H).

5-(3-Amino-2-fluoro-phenyl)-7-methyl-7H-pyrrolo[2,3-d]pyrimidin-4-ylamine hydrochloride salt, compound of formula (VII)

Scheme 1, Step e

[3-(4-Amino-7-methyl-7H-pyrrolo[2,3-d]pyrimidin-5-yl)-2-fluoro-phenyl]-carbamic acid tert-butyl ester (247 mg, 0.692 mmol) was taken up in dioxane (8 mL) and treated with 4M HCl in dioxane (4 mL, 16 mmol) at 40° C. overnight. The solvent was evaporated and the residue triturated with $Et_2O$ to afford the title compound (215 mg) as hydrochloride salt.

HPLC (254 nm): Rt: 3.33 min.

HRMS (ESI) calcd for $C_{13}H_{12}FN_5$ [M+H]$^+$ 258.115, found 258.1149.

$^1$H NMR (500 MHz, DMSO-d6) delta ppm: 3.85 (s, 3H) 6.58 (t, J=6.94 Hz, 1H) 6.86 (t, J=8.08 Hz, 1H) 6.94-7.05 (m, 1H) 7.63 (s, 1H) 8.47 (s, 1H).

Analogously the following compound was obtained:

3-(3-Amino-2-fluoro-phenyl)-1-methyl-1H-pyrazolo[3,4-d]pyrimidin-4-ylamine, compound of formula (VII)

MS (ESI) for $C_{12}H_{11}FN_6$ (MW: 258.26): [M+H]$^+$ found 259.

N-[3-(4-Amino-7-methyl-7H-pyrrolo[2,3-d]pyrimidin-5-yl)-2-fluoro-phenyl]-4-methoxy-3-methyl-benzenesulfonamide, compound of formula (I) (cmpd 12)

Scheme 1, Step f

In a screw cap vial, 5-(3-amino-2-fluoro-phenyl)-7-methyl-7H-pyrrolo[2,3-d]pyrimidin-4-ylamine hydrochloride salt (48 mg, 0.145 mmol) was suspended in DCM (4 mL). Pyridine (232 microL, 2.887 mmol) and 4-methoxy-3-methyl-benzenesulfonyl chloride (64 mg, 0.290 mmol) were added and the reaction was stirred at room temperature overnight. The mixture was diluted with DCM, washed with saturated aqueous $NaHCO_3$, brine, dried over $Na_2SO_4$ and evaporated under vacuum. The crude was purified by silica gel chromatography which was eluted with DCM:MeOH=95:5. The solid obtained was triturated with $Et_2O$ to afford the title compound (33 mg) as white solid.

HPLC (254 nm): Rt: 7.43 min.

HRMS (ESI) calcd for $C_{21}H_{20}FN_5O_3S$ [M+H]$^+$ 442.1344, found 442.1352.

$^1$H NMR (401 MHz, DMSO-d6) delta ppm: 2.15 (s, 3H) 3.73 (s, 3H) 3.84 (s, 3H) 5.96 (br. s., 2H) 7.08 (d, J=8.67 Hz, 1H) 7.10-7.21 (m, 3H) 7.22 (s, 1H) 7.53-7.62 (m, 2H) 8.14 (s, 1H) 10.04 (br. s., 1H).

Analogously the following compounds were obtained:

N-[3-(4-Amino-7-methyl-7H-pyrrolo[2,3-d]pyrimidin-5-yl)-2-fluoro-phenyl]-3-chloro-benzenesulfonamide, compound of formula (I), (cmpd 13)

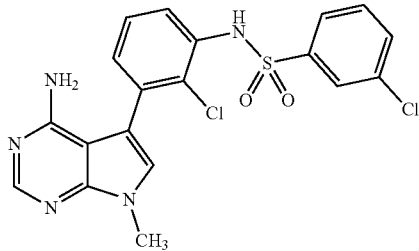 [SMILES: Cn1cc(-c2cccc(NS(=O)(=O)c3cccc(Cl)c3)c2Cl)c2c(N)ncnc21]

HPLC (254 nm): Rt: 7.46 min.

HRMS (ESI) calcd for $C_{19}H_{15}ClFN_5O_2S$ [M+H]$^+$ 432.0692, found 432.0695.

$^1$H NMR (401 MHz, DMSO-d6) delta ppm: 3.76 (s, 3H) 6.45 (br. s., 2H) 7.12-7.26 (m, 3H) 7.32 (s, 1H) 7.59-7.64 (m, 1H) 7.69-7.77 (m, 2H) 7.78-7.81 (m, 1H) 8.23 (s, 1H) 10.40 (br. s., 1H).

N-[3-(4-Amino-7-methyl-7H-pyrrolo[2,3-d]pyrimidin-5-yl)-2-fluoro-phenyl]-4-methoxy-benzenesulfonamide, compound of formula (I), (cmpd 14)

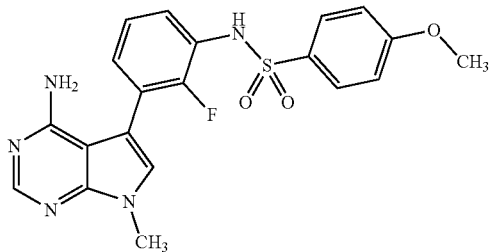 [SMILES: COc1ccc(S(=O)(=O)Nc2cccc(-c3cn(C)c4ncnc(N)c34)c2F)cc1]

HPLC (254 nm): Rt: 6.44 min.

HRMS (ESI) calcd for $C_{20}H_{18}FN_5O_3S$ [M+H]$^+$ 428.1187, found 428.1196.

$^1$H NMR (401 MHz, DMSO-d6) delta ppm: 3.73 (s, 3H) 3.81 (s, 3H) 5.95 (br. s., 2H) 7.08 (d, J=8.91 Hz, 2H) 7.13-7.28 (m, 4H) 7.70 (d, J=8.91 Hz, 2H) 8.15 (s, 1H) 10.07 (s, 1H).

N-[3-(4-Amino-7-methyl-7H-pyrrolo[2,3-d]pyrimidin-5-yl)-2-fluoro-phenyl]-4-trifluoromethyl-benzenesulfonamide, compound of formula (I), (cmpd 15)

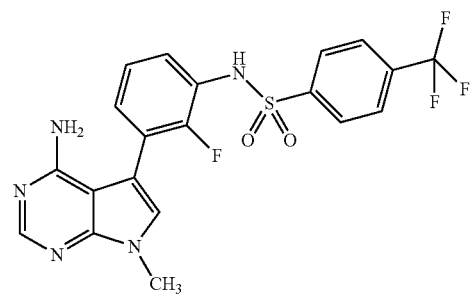 [SMILES: Cn1cc(-c2cccc(NS(=O)(=O)c3ccc(C(F)(F)F)cc3)c2F)c2c(N)ncnc21]

HPLC (254 nm): Rt: 8.35 min.

HRMS (ESI) calcd for $C_{20}H_{15}F_4N_5O_2S$ [M+H]$^+$ 466.0956, found 466.0955. $^1$H NMR (401 MHz, DMSO-d6) delta ppm: 3.70-3.79 (m, 3H) 6.61 (br. s., 2H) 7.14-7.26 (m, 3H) 7.31 (s, 1H) 7.90-8.04 (m, 4H) 8.25 (s, 1H) 10.52 (br. s., 1H).

Pyridine-3-sulfonic acid [3-(4-amino-7-methyl-7H-pyrrolo[2,3-d]pyrimidin-5-yl)-2-fluoro-phenyl]-amide, compound of formula (I), (cmpd 16)

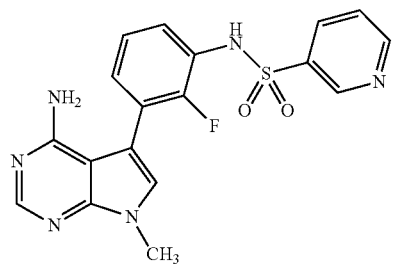 [SMILES: Cn1cc(-c2cccc(NS(=O)(=O)c3cccnc3)c2F)c2c(N)ncnc21]

HPLC (254 nm): Rt: 4.34 min.

HRMS (ESI) calcd for $C_{18}H_{15}FN_6O_2S$ [M+H]$^+$ 399.1034, found 399.1029.

$^1$H NMR (401 MHz, DMSO-d6) delta ppm: 3.72 (s, 3H) 5.96 (br. s., 2H) 6.99-7.34 (m, 4H) 7.63 (ddd, J=8.06, 4.88, 0.73 Hz, 1H) 8.13 (m, J=2.32, 1.59 Hz, 1H) 8.14 (s, 1H) 8.82 (dd, J=4.76, 1.59 Hz, 1H) 8.86-9.00 (m, 1H) 10.49 (br. s., 1H).

N-[3-(4-Amino-7-methyl-7H-pyrrolo[2,3-d]pyrimidin-5-yl)-2-fluoro-phenyl]-3,4-dimethm-benzenesulfonamide, compound of formula (I), (cmpd 17)

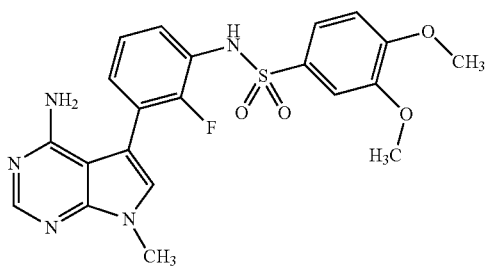 [SMILES: COc1ccc(S(=O)(=O)Nc2cccc(-c3cn(C)c4ncnc(N)c34)c2F)cc1OC]

HPLC (254 nm): Rt: 4.89 min.

HRMS (ESI) calcd for $C_{21}H_{20}FN_5O_4S$ $[M+H]^+$ 458.1293, found 458.1304.

$^1$H NMR (401 MHz, DMSO-d6) delta ppm: 3.73 (s, 3H) 3.73 (s, 3H) 3.81 (s, 3H) 5.95 (br. s., 2H) 7.09 (d, J=8.54 Hz, 1H) 7.13-7.21 (m, 3H) 7.22 (s, 1H) 7.27 (d, J=2.20 Hz, 1H) 7.33 (dd, J=8.48, 2.14 Hz, 1H) 8.15 (s, 1H) 10.03 (s, 1H).

4-Methyl-3,4-dihydro-2H-benzo[1,4]oxazine-7-sulfonic acid [3-(4-amino-7-methyl-7H-pyrrolo[2,3-d]pyrimidin-5-yl)-2-fluoro-phenyl]-amide, compound of formula (I), (cmpd 18)

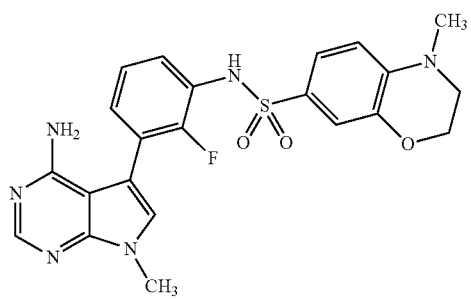 [SMILES: CN1CCOc2cc(S(=O)(=O)Nc3cccc(-c4cn(C)c5ncnc(N)c45)c3F)ccc21]

HPLC (254 nm): Rt: 5.24 min.

HRMS (ESI) calcd for $C_{22}H_{21}FN_6O_3S$ $[M+H]^+$ 469.1453, found 469.1463.

$^1$H NMR (401 MHz, DMSO-d6) delta ppm: 2.78 (s, 3H) 3.24-3.28 (m, 2H) 3.73 (s, 3H) 4.19-4.34 (m, 2H) 5.95 (br. s., 2H) 6.78 (d, J=8.91 Hz, 1H) 6.96-7.01 (m, 1H) 6.98 (s, 1H) 7.12-7.25 (m, 3H) 7.23 (s, 1H) 8.15 (s, 1H) 9.96 (s, 1H).

N-[3-(4-Amino-7-methyl-7H-pyrrolo[2,3-d]pyrimidin-5-yl)-2-fluoro-phenyl]-4-nitro-benzenesulfonamide, compound of formula (I), (cmpd 19)

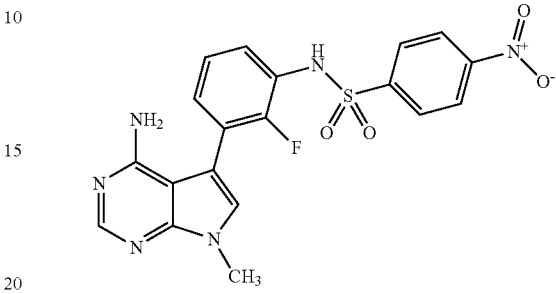

HPLC (254 nm): Rt: 5.21 min.

HRMS (ESI) calcd for $C_{19}H_{15}FN_6O_4S$ $[M+H]^+$ 443.0933, found 443.0944.

$^1$H NMR (401 MHz, DMSO-d6) delta ppm: 3.72 (s, 3H) 5.97 (br. s., 2H) 7.15-7.29 (m, 4H) 7.98-8.06 (m, 2H) 8.14 (s, 1H) 8.35-8.44 (m, 2H) 10.63 (br. s., 1H).

Naphthalene-2-sulfonic acid [3-(4-amino-7-methyl-7H-pyrrolo[2,3-d]pyrimidin-5-yl)-2-fluoro-phenyl]-amide, compound of formula (I), (cmpd 20)

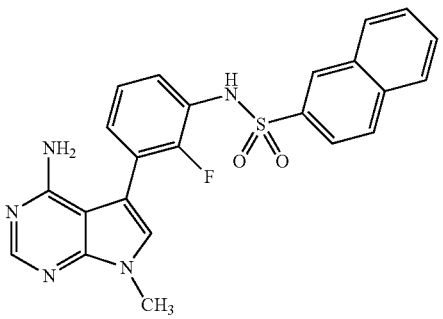 [SMILES: Cn1cc(-c2cccc(NS(=O)(=O)c3ccc4ccccc4c3)c2F)c2c(N)ncnc21]

HPLC (254 nm): Rt: 5.62 min.

HRMS (ESI) calcd for $C_{23}H_{18}FN_5O_2S$ $[M+H]^+$ 448.1238, found 448.1242.

$^1$H NMR (401 MHz, DMSO-d6) delta ppm: 3.68 (s, 3H) 5.92 (br. s., 2H) 7.08 (s, 1H) 7.10-7.27 (m, 3H) 7.62-7.68 (m, 1H) 7.68-7.75 (m, 1H) 7.82 (dd, J=8.73, 1.89 Hz, 1H) 8.03 (d, J=8.18 Hz, 1H) 8.13 (t, J=4.27 Hz, 3H) 8.40 (d, J=1.46 Hz, 1H) 10.33 (s, 1H).

N-[3-(4-Amino-7-methyl-7H-pyrrolo[2,3-d]pyrimidin-5-yl)-2-fluoro-phenyl]-2,5-difluoro-benzenesulfonamide, compound of formula (I), (cmpd 21)

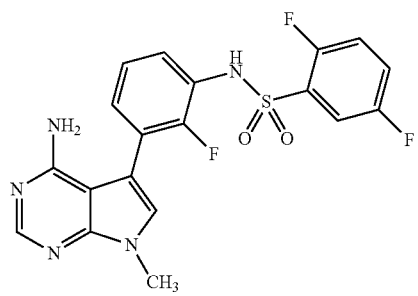 [SMILES: Cn1cc(-c2cccc(NS(=O)(=O)c3cc(F)ccc3F)c2F)c2c(N)ncnc21]

HPLC (254 nm): Rt: 5.21 min.

HRMS (ESI) calcd for $C_{19}H_{14}F_3N_5O_2S$ $[M+H]^+$ 434.0893, found 434.0901.

$^1$H NMR (401 MHz, DMSO-d6) delta ppm: 3.73 (s, 3H) 5.96 (br. s., 2H) 7.13-7.32 (m, 4H) 7.51-7.67 (m, 3H) 8.15 (s, 1H) 10.70 (br. s., 1H).

N-[3-(4-Amino-7-methyl-7H-pyrrolo[2,3-d]pyrimidin-5-yl)-2-fluoro-phenyl]-4-bromo-2-fluoro-benzenesulfonamide, compound of formula (I), (cmpd 22)

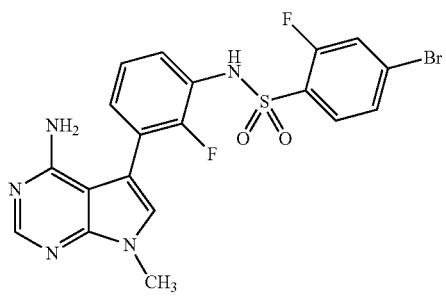 [SMILES: Cn1cc(-c2cccc(NS(=O)(=O)c3ccc(Br)cc3F)c2F)c2c(N)ncnc21]

HPLC (254 nm): Rt: 5.57 min.

HRMS (ESI) calcd for $C_{19}H_{14}BrF_2N_5O_2S$ $[M+H]^+$ 494.0093, found 494.0105.

$^1$H NMR (401 MHz, DMSO-d6) delta ppm: 3.73 (s, 3H) 5.96 (br. s., 2H) 7.09-7.32 (m, 4H) 7.59 (dd, J=8.42, 1.59 Hz, 1H) 7.65-7.73 (m, 1H) 7.88 (dd, J=10.01, 1.34 Hz, 1H) 8.15 (s, 1H) 10.64 (br. s., 1H).

N-[3-(4-Amino-7-methyl-7H-pyrrolo[2,3-d]pyrimidin-5-yl)-2-fluoro-phenyl]-2,6-difluoro-benzenesulfonamide, compound of formula (I), (cmpd 23)

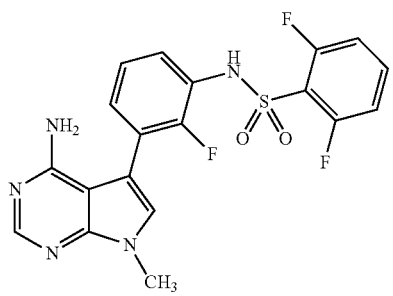 [SMILES: Cn1cc(-c2cccc(NS(=O)(=O)c3c(F)cccc3F)c2F)c2c(N)ncnc21]

HPLC (254 nm): Rt: 5.01 min.

HRMS (ESI) calcd for $C_{19}H_{14}F_3N_5O_2S$ $[M+H]^+$ 434.0893, found 434.0902.

$^1$H NMR (401 MHz, DMSO-d6) delta ppm: 3.74 (br. s., 3H) 5.92 (br. s., 2H) 7.05-7.37 (m, 6H) 7.65-7.78 (m, 1H) 8.15 (s, 1H) 10.82 (br. s., 1H).

N-[3-(4-Amino-7-methyl-7H-pyrrolo[2,3-d]pyrimidin-5-yl)-2-fluoro-phenyl]-5-chloro-2-fluoro-4-methoxy-benzenesulfonamide, compound of formula (I), (cmpd 24)

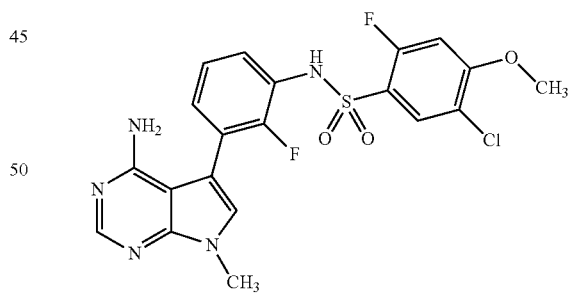

HPLC (254 nm): Rt: 5.56 min.

HRMS (ESI) calcd for $C_{20}H_{16}ClF_2N_5O_3S$ $[M+H]^+$ 480.0703, found 480.0711.

$^1$H NMR (401 MHz, DMSO-d6) delta ppm: 3.71-3.76 (m, 3H) 3.94 (s, 3H) 5.98 (br. s., 2H) 7.15-7.28 (m, 4H) 7.36 (d, J=12.08 Hz, 1H) 7.71 (d, J=7.45 Hz, 1H) 8.15 (s, 1H) 10.50 (s, 1H).

N-[3-(4-Amino-7-methyl-7H-pyrrolo[2,3-d]pyrimidin-5-yl)-2-fluoro-phenyl]-3,4-dichloro-benzenesulfonamide, compound of formula (I), (cmpd 25)

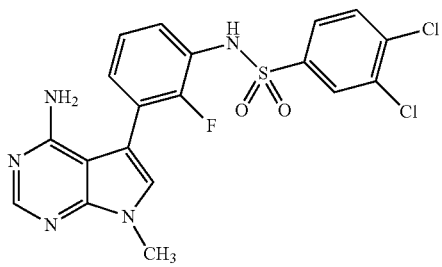 [SMILES: Cn1cc(-c2cccc(NS(=O)(=O)c3ccc(Cl)c(Cl)c3)c2F)c2c(N)ncnc21]

HPLC (254 nm): Rt: 5.85 min.

HRMS (ESI) calcd for $C_{19}H_{14}Cl_2FN_5O_2S$ [M+H]$^+$ 466.0302, found 466.0309.

$^1$H NMR (401 MHz, DMSO-d6) delta ppm: 3.73 (s, 3H) 6.00 (br. s., 2H) 7.10-7.27 (m, 4H) 7.71 (dd, J=8.48, 2.14 Hz, 1H) 7.88 (d, J=8.42 Hz, 1H) 7.95 (d, J=2.07 Hz, 1H) 8.15 (s, 1H) 10.45 (br. s., 1H).

N-[2-(4-Amino-7-methyl-7H-pyrrolo[2,3-d]pyrimidin-5-yl)-2-fluoro-phenyl]-3,5-dichloro-benzenesulfonamide, compound of formula (I), (cmpd 26)

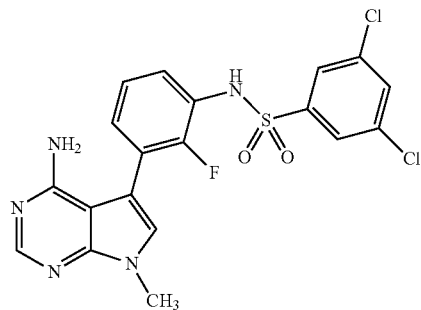 [SMILES: Cn1cc(-c2cccc(NS(=O)(=O)c3cc(Cl)cc(Cl)c3)c2F)c2c(N)ncnc21]

HPLC (254 nm): Rt: 5.91 min.

HRMS (ESI) calcd for $C_{19}H_{14}Cl_2FN_5O_2S$ [M+H]$^+$ 466.0302, found 466.0304.

$^1$H NMR (401 MHz, DMSO-d6) delta ppm: 3.73 (s, 3H) 6.00 (br. s., 2H) 7.13-7.30 (m, 4H) 7.73 (d, J=1.95 Hz, 2H) 7.96 (t, J=1.71 Hz, 1H) 8.15 (s, 1H) 10.52 (br. s., 1H).

2,3-Dihydro-benzofuran-5-sulfonic acid [3-(4-amino-7-methyl-7H-pyrrolo[2,3-d]pyrimidin-5-yl)-2-fluoro-phenyl]-amide, compound of formula (I), (cmpd 27)

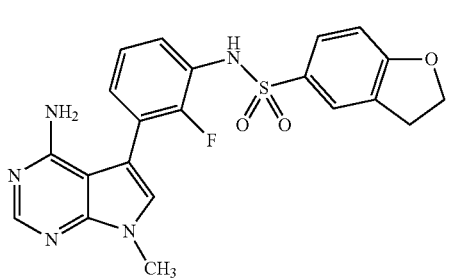 [SMILES: Cn1cc(-c2cccc(NS(=O)(=O)c3ccc4c(c3)CCO4)c2F)c2c(N)ncnc21]

HPLC (254 nm): Rt: 5.08 min.

HRMS (ESI) calcd for $C_{21}H_{18}FN_5O_3S$ [M+H]$^+$ 440.1187, found 440.1205.

$^1$H NMR (401 MHz, DMSO-d6) delta ppm: 3.21 (t, J=8.79 Hz, 2H) 3.73 (s, 3H) 4.62 (t, J=8.85 Hz, 2H) 5.96 (br. s., 2H) 6.89 (d, J=8.42 Hz, 1H) 7.10-7.23 (m, 3H) 7.24 (s, 1H) 7.53 (dd, J=8.54, 2.08 Hz, 1H) 7.63 (d, J=1.71 Hz, 1H) 8.15 (s, 1H) 10.01 (s, 1H).

N-[3-(4-Amino-7-methyl-7H-pyrrolo[2,3-d]pyrimidin-5-yl)-2-fluoro-phenyl]-4-ethoxy-3-methyl-benzenesulfonamide, compound of formula (I), (cmpd 28)

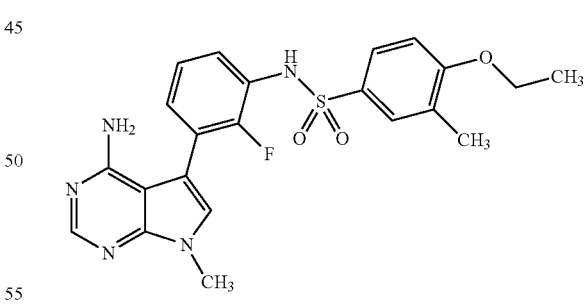

HPLC (254 nm): Rt: 10.44 min.

HRMS (ESI) calcd for $C_{22}H_{22}FN_5O_3S$ [M+H]$^+$ 456.15, found 456.1511.

$^1$H NMR (401 MHz, DMSO-d6) delta ppm: 1.34 (t, J=6.96 Hz, 3H) 2.15 (s, 3H) 3.73 (s, 3H) 4.09 (q, J=6.96 Hz, 2H) 5.95 (br. s., 2H) 7.02-7.09 (m, 1H) 7.12-7.20 (m, 3H) 7.22 (s, 1H) 7.52-7.60 (m, 2H) 8.15 (s, 1H) 10.00 (s, 1H).

N-[3-(4-Amino-7-methyl-7H-pyrrolo[2,3-d]pyrimidin-5-yl)-2-fluoro-phenyl]-4-methoxy-3,5-dimethyl-benzenesulfonamide, compound of formula (I), (cmpd 29)

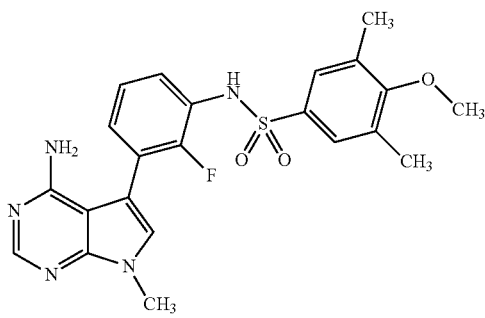 [SMILES: COc1c(C)cc(S(=O)(=O)Nc2cccc(-c3cn(C)c4ncnc(N)c34)c2F)cc1C]

HPLC (254 nm): Rt: 5.55 min.
HRMS (ESI) calcd for C$_{22}$H$_{22}$FN$_5$O$_3$S [M+H]$^+$ 456.15, found 456.1505.
$^1$H NMR (401 MHz, DMSO-d6) delta ppm: 2.24 (s, 6H) 3.68 (s, 3H) 3.73 (s, 3H) 5.97 (br. s., 2H) 7.09-7.21 (m, 3H) 7.23 (s, 1H) 7.47 (s, 2H) 8.15 (s, 1H) 10.08 (s, 1H).

N-[3-(4-Amino-7-methyl-7H-pyrrolo[2,3-d]pyrimidin-5-yl)-2-fluoro-phenyl]-4-isopropoxy-3-methyl-benzenesulfonamide, compound of formula (I), (cmpd 30)

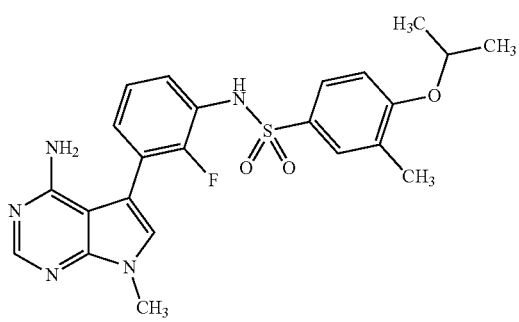 [SMILES: Cc1cc(S(=O)(=O)Nc2cccc(-c3cn(C)c4ncnc(N)c34)c2F)ccc1OC(C)C]

HPLC (254 nm): Rt: 7.93 min.
HRMS (ESI) calcd for C23H24FN5O3S [M+H]$^+$ 470.1657, found 470.1643.

N-[3-(4-Amino-7-methyl-7H-pyrrolo[2,3-d]pyrimidin-5-yl)-2-fluoro-phenyl]-3,4-dimethyl-benzenesulfonamide, compound of formula (I), (cmpd 31)

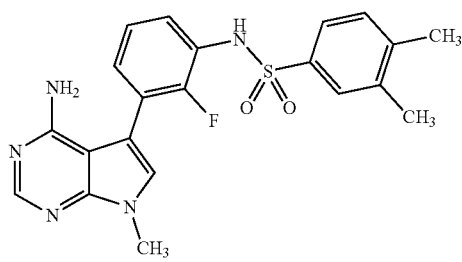 [SMILES: Cc1ccc(S(=O)(=O)Nc2cccc(-c3cn(C)c4ncnc(N)c34)c2F)cc1C]

HPLC (254 nm): Rt: 5.55 min.

HRMS (ESI) calcd for C$_{21}$H$_{20}$FN$_5$O$_2$S [M+H]$^+$ 426.1395, found 426.1385.
$^1$H NMR (500 MHz, DMSO-d6) delta ppm: 2.25 (s, 3H) 2.27 (s, 3H) 3.72 (s, 3H) 5.98 (br. s., 2H) 7.06-7.20 (m, 3H) 7.23 (s, 1H) 7.32 (d, J=7.93 Hz, 1H) 7.44-7.51 (m, 1H) 7.55 (s, 1H) 8.14 (s, 1H) 10.15 (s, 1H).

N-[3-(4-Amino-7-methyl-7H-pyrrolo[2,3-d]pyrimidin-5-yl)-2-fluoro-phenyl]-3,4,5-trifluoro-benzenesulfonamide, compound of formula (I), (cmpd 32)

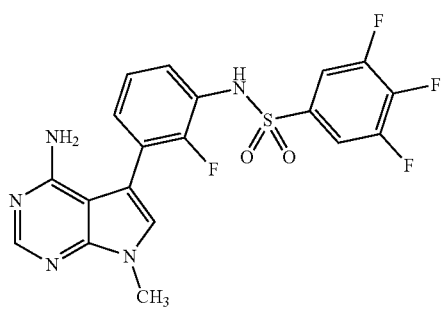 [SMILES: Cn1cc(-c2cccc(NS(=O)(=O)c3cc(F)c(F)c(F)c3)c2F)c2c(N)ncnc21]

HPLC (254 nm): Rt: 5.56 min.
HRMS (ESI) calcd for C$_{19}$H$_{13}$F$_4$N$_5$O$_2$S [M+H]$^+$ 452.0799, found 452.0786.
$^1$H NMR (500 MHz, DMSO-d6) delta ppm: 3.73 (s, 3H) 6.04 (br. s., 2H) 7.10-7.24 (m, 3H) 7.27 (s, 1H) 7.74 (t, J=6.56 Hz, 2H) 8.15 (s, 1H) 10.54 (br. s., 1H).

5-Bromo-6-chloro-pyridine-3-sulfonic acid [3-(4-amino-7-methyl-7H-pyrrolo[2,3-d]pyrimidin-5-yl)-2-fluoro-phenyl]-amide, compound of formula (I), (cmpd 33)

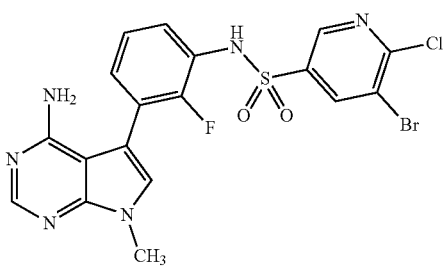 [SMILES: Cn1cc(-c2cccc(NS(=O)(=O)c3cnc(Cl)c(Br)c3)c2F)c2c(N)ncnc21]

HPLC (254 nm): Rt: 5.49 min.
HRMS (ESI) calcd for C$_{18}$H$_{13}$BrClFN$_6$O$_2$S [M+H]$^+$ 510.975, found 510.9738.
$^1$H NMR (500 MHz, DMSO-d6) delta ppm: 3.73 (s, 3H) 6.07 (br. s., 2H) 7.12-7.27 (m, 4H) 8.15 (s, 1H) 8.49 (d, J=2.14 Hz, 1H) 8.72 (d, J=2.29 Hz, 1H) 10.65 (br. s., 1H).

N-[3-(4-Amino-1-methyl-1H-pyrazolo[3,4-d]pyrimidin-3-yl)-2-fluoro-phenyl]-4-methoxy-3-methyl-benzenesulfonamide, compound of formula (I), (cmpd 34)

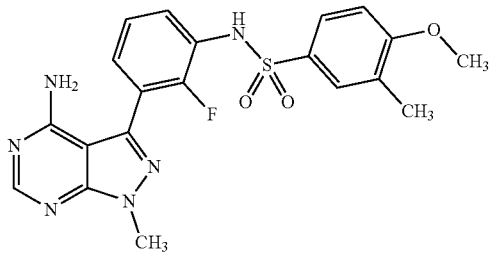 [SMILES: COc1ccc(S(=O)(=O)Nc2cccc(-c3nn(C)c4ncnc(N)c34)c2F)cc1C]

HPLC (254 nm): Rt: 5.23 min.

HRMS (ESI) calcd for $C_{20}H_{19}FN_6O_3S$ [M+H]$^+$ 443.1296, found 443.1299.

$^1$H NMR (401 MHz, DMSO-d6) delta ppm: 2.15 (s, 3H) 3.84 (s, 3H) 3.93 (s, 3H) 7.07 (d, J=8.67 Hz, 1H) 7.20-7.26 (m, 1H) 7.26-7.36 (m, 2H) 7.57 (d, J=1.59 Hz, 1H) 7.61 (dd, J=8.54, 2.32 Hz, 1H) 8.24 (s, 1H) 10.07 (s, 1H).

N-[3-(4-Amino-1-methyl-1H-pyrazolo[3,4-d]pyrimidin-3-yl)-2-fluoro-phenyl]-3-chloro-4-methoxy-benzenesulfonamide, compound of formula (I) (cmpd 35)

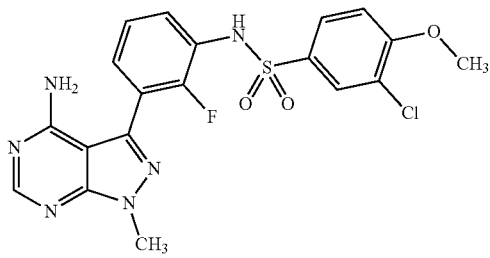 [SMILES: COc1ccc(S(=O)(=O)Nc2cccc(-c3nn(C)c4ncnc(N)c34)c2F)cc1Cl]

HPLC (254 nm): Rt: 5.22 min.

HRMS (ESI) calcd for $C_{19}H_{16}ClFN_6O_3S$ [M+H]$^+$ 463.075, found 463.0749.

$^1$H NMR (401 MHz, DMSO-d6) delta ppm: 3.92 (s, 3H) 3.93 (s, 3H) 7.23-7.28 (m, 1H) 7.28-7.36 (m, 3H) 7.71 (dd, J=8.67, 2.32 Hz, 1H) 7.81 (d, J=2.32 Hz, 1H) 8.24 (s, 1H) 10.24 (s, 1H).

EXAMPLE 4

N-{3-[4-Amino-7-(tetrahydro-pyran-4-yl)-7H-pyrrolo[2,3-d]pyrimidin-5-yl]-2-fluoro-phenyl}-4-methoxy-3-methyl-benzenesulfonamide, compound of formula (I) (cmpd 36)

Scheme 1

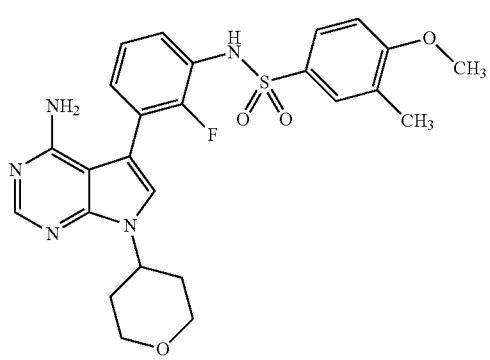

5-(3-Amino-2-fluoro-phenyl)-7-(tetrahydro-pyran-4-yl)-7H-pyrrolo[2,3-d]pyrimidin-4-ylamine, compound of formula (VII)

Scheme 1, Step b

In a Schlenk tube, to 5-iodo-7-(tetrahydro-pyran-4-yl)-7H-pyrrolo[2,3-d]pyrimidin-4-ylamine (70 mg, 0.203 mmol), 2-fluoro-3-(4,4,5,5-tetramethyl-[1,3,2]dioxaborolan-2-yl)-phenylamine (104 mg, 0.439 mmol), Cs$_2$CO$_3$ (250 mg, 0.767 mmol) and 1,1'-bis(diphenylphosphino)ferrocene]dichloropalladium(II), complex with dichloromethane (1:1) (14 mg, 0.017 mmol) were added 1,2-dimethoxyethane (DME) (3.6 mL) and water (0.4 mL). The reaction mixture was degassed with nitrogen, heated to 85° C. for 5 hours and then filtered through a celite pad. The filtrate was evaporated under reduced pressure; the crude was taken up with DCM, washed with saturated aqueous NaHCO$_3$, brine and dried over Na$_2$SO$_4$. The solvent was evaporated and the crude was purified by silica gel chromatography which was eluted with DCM:MeOH=95:5. The solid obtained was triturated with Et$_2$O to afford the title compound (39 mg) as white solid.

HPLC (254 nm): Rt: 4.30 min.

HRMS (ESI) calcd for $C_{17}H_{18}FN_5O$ [M+H]$^+$ 328.1568, found 328.1575.

$^1$H NMR (401 MHz, DMSO-d6) delta ppm: 1.87 (dd, J=12.33, 2.44 Hz, 2H) 2.02-2.18 (m, 2H) 3.53 (t, J=11.17 Hz, 2H) 4.00 (dd, J=11.23, 4.03 Hz, 2H) 4.83 (tt, J=11.93, 3.94 Hz, 1H) 5.23 (br. s., 2H) 5.99 (br. s., 2H) 6.41-6.61 (m, 1H) 6.77 (td, J=8.24, 1.59 Hz, 1H) 6.88-7.02 (m, 1H) 7.42 (s, 1H) 8.13 (s, 1H).

Analogously the following compounds were obtained:

5-(3-Amino-2-fluoro-phenyl)-7-(1-methyl-piperidin-4-yl)-7H-pyrrolo[2,3-d]pyrimidin-4-ylamine, compound of formula (VII)

HPLC (254 nm): Rt: 3.32 min.

HRMS (ESI) calcd for $C_{18}H_{21}FN_6$ [M+H]$^+$ 341.1885, found 341.1895.

$^1$H NMR (401 MHz, DMSO-d6) delta ppm: 1.77-1.96 (m, 2H) 2.00-2.15 (m, 4H) 2.22 (s, 3H) 2.79-3.00 (m, 2H)

4.42-4.63 (m, 1H) 5.22 (s, 2H) 5.97 (br. s., 2H) 6.52 (ddd, J=7.50, 6.70, 1.60 Hz, 1H) 6.77 (td, J=8.21, 1.65 Hz, 1H) 6.95 (ddd, J=7.90, 7.50, 0.60 Hz, 1H) 7.37 (s, 1H) 8.12 (s, 1H).

5-(3-Amino-2-fluoro-phenyl)-7-(1-isopropyl-piperidin-4-yl)-7H-pyrrolo[2,3-d]pyrimidin-4-ylamine, compound of formula (VII)

MS (ESI) for $C_{20}H_{25}FN6$ (MW: 368.46): [M+H]$^+$ found 369.

5-(3-Amino-2-fluoro-phenyl)-7-(1-cyclopropyl-piperidin-4-yl)-7H-pyrrolo[2,3-d]pyrimidin-4-ylamine, compound of formula (VII)

MS (ESI) for $C_{20}H_{26}FN6$ (MW: 366.24): [M+H]$^+$ found 367.

4-[4-Amino-5-(3-amino-2-fluoro-phenyl)-pyrrolo[2,3-d]pyrimidin-7-yl]-piperidine-1-carboxylic acid tert-butyl ester, compound of formula (VII)

HPLC (254 nm): Rt: 5.69 min.
HRMS (ESI) calcd for $C_{22}H_{27}FN_6O_2$ [M+H]$^+$ 427.2253, found 427.2245.
$^1$H NMR (500 MHz, DMSO-d6) delta ppm: 1.42 (s, 9H) 1.84-2.01 (m, 4H) 2.94 (br. s., 2H) 4.11 (br. s., 2H) 4.67-4.80 (m, 1H) 5.25 (s, 2H) 6.51 (t, J=6.48 Hz, 1H) 6.76 (t, J=7.55 Hz, 1H) 6.94 (t, J=7.85 Hz, 1H) 7.43 (s, 1H) 8.12 (s, 1H).

5-(3-Amino-2-fluoro-phenyl)-7-methyl-7H-pyrrolo[2,3-d]pyrimidin-4-ylamine, compound of formula (VII)

HPLC (254 nm): Rt: 4.03 min.
HRMS (ESI) calcd for $C_{13}H_{12}FN_5$ [M+H]$^+$ 258.115, found 258.1154.
$^1$H NMR (500 MHz, DMSO-d6) delta ppm: 3.74 (s, 3H) 5.26 (s, 2H) 5.76 (s, 2H) 6.45-6.57 (m, 1H) 6.76 (td, J=8.24, 1.53 Hz, 1H) 6.87-7.00 (m, 1H) 7.27 (s, 1H) 8.14 (s, 1H).

5-(3-Amino-2-methyl-phenyl)-7-methyl-7H-pyrrolo[2,3-d]pyrimidin-4-ylamine, compound of formula (VII)

HPLC (254 nm): Rt: 4.05 min.
HRMS (ESI) calcd for $C_{14}H_{15}N_5$ [M+H]$^+$ 254.14, found 254.1397.
$^1$H NMR (500 MHz, DMSO-d6) delta ppm: 1.92 (s, 3H) 3.73 (s, 3H) 4.95-5.06 (m, 2H) 5.11-6.29 (m, 2H) 6.46 (dd, J=7.32, 0.92 Hz, 1H) 6.61-6.71 (m, 1H) 6.87-6.98 (m, 1H) 7.07 (s, 1H) 8.11 (s, 1H).

5-(3-Amino-2-chloro-phenyl)-7-methyl-7H-pyrrolo[2,3-d]pyrimidin-4-ylamine, compound of formula (VII)

HPLC (254 nm): Rt: 4.25 min.
HRMS (ESI) calcd for $C_{13}H_{12}ClN_5$ [M+H]$^+$ 274.0854, found 274.0852.
$^1$H NMR (500 MHz, DMSO-d6) delta ppm: 3.74 (s, 3H) 5.50 (s, 2H) 5.55-6.38 (m, 2H) 6.56 (dd, J=7.47, 1.53 Hz, 1H) 6.83 (dd, J=8.16, 1.60 Hz, 1H) 7.08 (t, J=7.70 Hz, 1H) 7.21 (s, 1H) 8.13 (s, 1H).

N-{3-[4-Amino-7-(tetrahydro-pyran-4-yl)-7H-pyrrolo[2,3-d]pyrimidin-5-yl]-2-fluoro-phenyl}-4-methoxy-3-methyl-benzenesulfonamide, compound of formula (I) (cmpd 36)

Scheme 1, Step f

To 5-(3-amino-2-fluoro-phenyl)-7-(tetrahydro-pyran-4-yl)-7H-pyrrolo[2,3-d]pyrimidin-4-ylamine (15 mg, 0.046 mmol) in DCM (1.5 mL) were added pyridine (6 microL, 0.074 mmol) and 4-methoxy-3-methyl-benzenesulfonyl chloride (14 mg, 0.063 mmol). The reaction was stirred at room temperature overnight. Then the reaction was diluted with DCM, washed with saturated aqueous NaHCO$_3$, brine, dried over Na$_2$SO$_4$ and evaporated. The crude was purified by silica gel chromatography which was eluted with DCM:MeOH=95:5 to furnish the title compound (24 mg) as white solid.

HPLC (254 nm): Rt: 5.54 min.
HRMS (ESI) calcd for $C_{25}H_{26}FN_5O_4S$ [M+H]$^+$ 512.1763, found 512.1758.
$^1$H NMR (401 MHz, DMSO-d6) delta ppm: 1.87 (dd, J=12.14, 2.62 Hz, 2H) 1.97-2.13 (m, 2H) 2.15 (s, 3H) 3.52 (m, J=11.11, 11.11 Hz, 2H) 3.85 (s, 3H) 3.99 (dd, J=11.35, 4.15 Hz, 2H) 4.82 (tt, J=11.92, 3.89 Hz, 1H) 5.97 (br. s., 2H) 7.09 (d, J=8.79 Hz, 1H) 7.13-7.24 (m, 3H) 7.33 (s, 1H) 7.54 (d, J=1.71 Hz, 1H) 7.59 (dd, J=8.67, 2.20 Hz, 1H) 8.13 (s, 1H) 10.00 (s, 1H).

Analogously the following compounds were obtained:

N-{3-[4-Amino-7-(tetrahydro-pyran-4-yl)-7H-pyrrolo[2,3-d]pyrimidin-5-yl]-2-fluoro-phenyl}-3-chloro-4-methoxy-benzenesulfonamide, compound of formula (I) (cmpd 37)

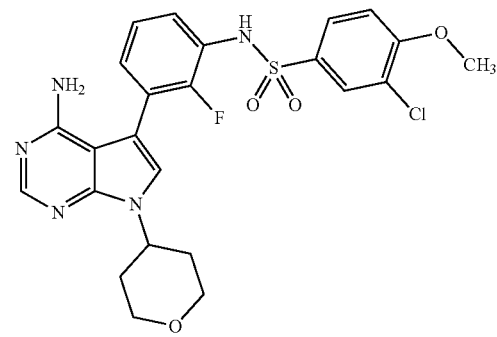 [SMILES: COc1ccc(S(=O)(=O)Nc2cccc(-c3cn(C4CCOCC4)c4ncnc(N)c34)c2F)cc1Cl]

HPLC (254 nm): Rt: 5.55 min.
HRMS (ESI) calcd for $C_{24}H_{23}ClFN_5O_4S$ [M+H]$^+$ 532.1216, found 532.1213.
$^1$H NMR (401 MHz, DMSO-d6) delta ppm: 1.87 (dd, J=12.08, 2.44 Hz, 2H) 1.96-2.13 (m, 2H) 3.45-3.61 (m, 2H) 3.93 (s, 3H) 3.99 (dd, J=11.29, 4.09 Hz, 2H) 4.82 (tt, J=11.90, 4.09 Hz, 1H) 5.99 (br. s., 2H) 7.11-7.25 (m, 3H) 7.28-7.36 (m, 2H) 7.70 (dd, J=8.67, 2.32 Hz, 1H) 7.75 (d, J=2.32 Hz, 1H) 8.13 (s, 1H) 10.18 (s, 1H).

N-{3-[4-Amino-7-(1-methyl-piperidin-4-yl)-7H-pyrrolo[2,3-d]pyrimidin-5-yl]-2-fluoro-phenyl}-4-methoxy-3-methyl-benzenesulfonamide, compound of formula (I) (cmpd 38)

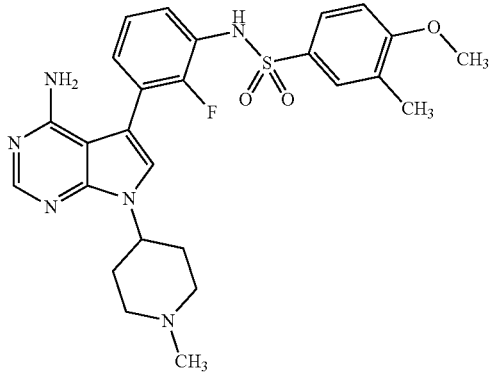 [SMILES: COc1ccc(S(=O)(=O)Nc2cccc(-c3cn(C4CCN(C)CC4)c4ncnc(N)c34)c2F)cc1C]

HPLC (254 nm): Rt: 4.85 min.
HRMS (ESI) calcd for $C_{26}H_{29}FN_6O_3S$ [M+H]$^+$ 525.2079, found 525.207.
$^1$H NMR (500 MHz, DMSO-d6) delta ppm: 1.89 (d, J=10.99 Hz, 2H) 2.05 (qd, J=12.08, 3.28 Hz, 2H) 2.15 (br. s, 2H) 2.15 (s, 3H) 2.27 (br. s., 3H) 2.94 (d, J=9.46 Hz, 2H) 3.84 (s, 3H) 4.55 (tt, J=11.88, 4.06 Hz, 1H) 5.99 (br. s., 2H) 7.09 (d, J=8.70 Hz, 1H) 7.13-7.23 (m, 3H) 7.30 (s, 1H) 7.54 (dd, J=2.37, 0.69 Hz, 1H) 7.59 (dd, J=8.62, 2.37 Hz, 1H) 8.12 (s, 1H) 10.01 (br. s., 1H).

N-{3-[4-Amino-7-(1-cyclopropyl-piperidin-4-yl)-7H-pyrrolo[2,3-d]pyrimidin-5-yl]-2-fluoro-phenyl}-4-methoxy-3-methyl-benzenesulfonamide, compound of formula (I) (cmpd 39)

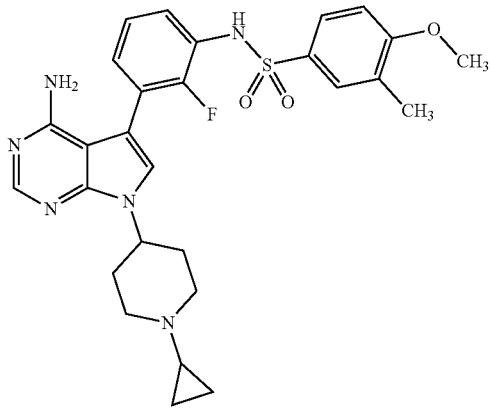 [SMILES: COc1ccc(S(=O)(=O)Nc2cccc(-c3cn(C4CCN(C5CC5)CC4)c4ncnc(N)c34)c2F)cc1C]

HPLC (254 nm): Rt: 5.69 min.
HRMS (ESI) calcd for $C_{28}H_{31}FN_6O_3S$ [M+H]$^+$ 551.2235, found 551.2244.
$^1$H NMR (500 MHz, DMSO-d6) delta ppm: 0.27-0.35 (m, 2H) 0.39-0.51 (m, 2H) 1.62-1.73 (m, 1H) 1.79-1.90 (m, 2H) 1.95 (qd, J=12.02, 3.58 Hz, 2H) 2.14 (s, 3H) 2.30-2.42 (m, 2H) 3.05 (d, J=11.44 Hz, 2H) 3.83 (s, 3H) 4.56 (tt, J=11.90, 3.97 Hz, 1H) 5.96 (br. s., 2H) 7.08 (d, J=8.85 Hz, 1H) 7.11-7.23 (m, 3H) 7.28 (s, 1H) 7.52 (dd, J=2.44, 0.76 Hz, 1H) 7.58 (dd, J=8.54, 2.29 Hz, 1H) 8.12 (s, 1H) 10.04 (br. s., 1H).

N-{3-[4-Amino-7-(1-isopropyl-piperidin-4-yl)-7H-pyrrolo[2,3-d]pyrimidin-5-yl]-2-fluoro-phenyl}-4-methoxy-3-methyl-benzenesulfonamide, compound of formula (I), (cmpd 40)

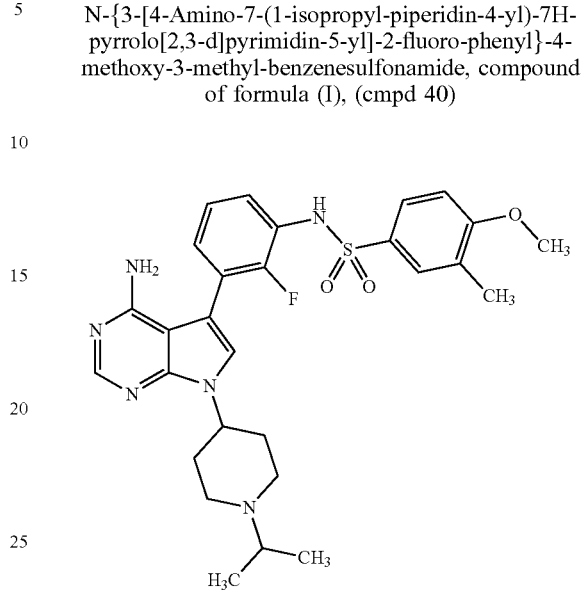

HPLC (254 nm): Rt: 5.03 min.
HRMS (ESI) calcd for $C_{28}H_{33}FN_6O_3S$ [M+H]$^+$ 553.2392, found 553.2408.
$^1$H NMR (500 MHz, DMSO-d6) delta ppm: 1.00 (d, J=6.56 Hz, 6H) 1.84-1.93 (m, 2H) 1.98 (qd, J=11.90, 2.90 Hz, 2H) 2.14 (s, 3H) 2.25-2.35 (m, 2H) 2.76 (spt, J=6.60 Hz, 1H) 2.92 (d, J=11.59 Hz, 2H) 3.84 (s, 3H) 4.51 (tt, J=11.93, 4.31 Hz, 1H) 5.96 (br. s., 2H) 7.06 (d, J=8.69 Hz, 2H) 7.11 (t, J=7.70 Hz, 1H) 7.18 (td, J=7.90, 1.70 Hz, 1H) 7.29 (s, 1H) 7.52 (d, J=1.68 Hz, 1H) 7.58 (dd, J=8.62, 2.21 Hz, 1H) 8.12 (s, 1H) 9.86 (br. s, 1H).

N-{3-[4-Amino-7-(1-ethyl-piperidin-4-yl)-7H-pyrrolo[2,3-d]pyrimidin-5-yl]-2-fluoro-phenyl}-4-methoxy-3-methyl-benzenesulfonamide, compound of formula (I), (cmpd 41)

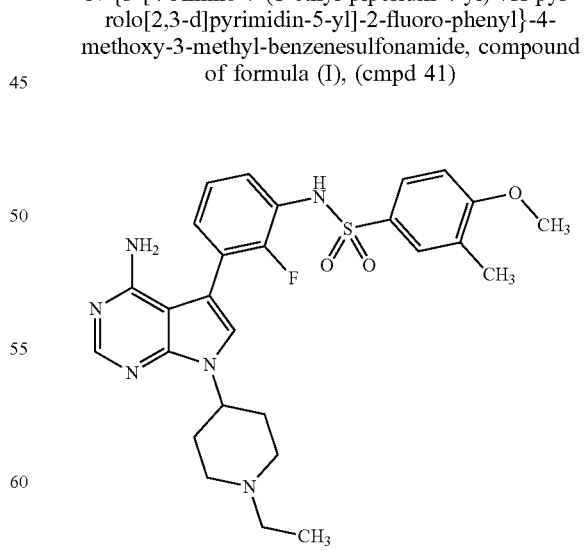

HPLC (254 nm): Rt: 4.72 min.
HRMS (ESI) calcd for $C_{27}H_{31}FN_6O_3S$ [M+H]$^+$ 539.2235, found 539.2239.

4-{4-Amino-5-[2-fluoro-3-(4-methoxy-3-methyl-benzenesulfonylamino)-phenyl]-pyrrolo[2,3-d]pyrimidin-7-yl}-piperidine-1-carboxylic acid tert-butyl ester, compound of formula (I), (cmpd 42)

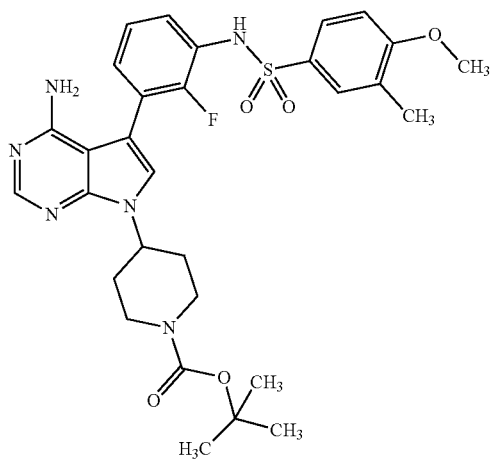 [SMILES: COc1ccc(S(=O)(=O)Nc2cccc(-c3cn(C4CCN(C(=O)OC(C)(C)C)CC4)c4ncnc(N)c34)c2F)cc1C]

MS (ESI) for C$_{30}$H$_{35}$FN$_6$O$_5$S (MW:610.71): [M+H]$^+$ found 611.

N-[3-(4-Amino-7-methyl-7H-pyrrolo[2,3-d]pyrimidin-5-yl)-2-fluoro-phenyl]-4,5-dichloro-2-fluoro-benzenesulfonamide, compound of formula (I), (cmpd 43)

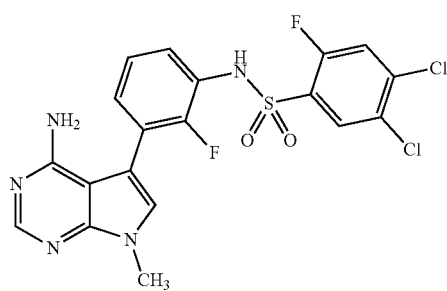 [SMILES: Cn1cc(-c2cccc(NS(=O)(=O)c3cc(Cl)c(Cl)cc3F)c2F)c2c(N)ncnc21]

HPLC (254 nm): Rt: 5.84 min.

HRMS (ESI) calcd for C$_{19}$H$_{13}$Cl$_2$F$_2$N$_5$O$_2$S [M+H]$^+$ 484.0208, found 484.0219.

$^1$H NMR (500 MHz, DMSO-d6) delta ppm: 3.73 (s, 3H) 6.05 (br. s., 2H) 7.14-7.30 (m, 4H) 7.93 (d, J=6.86 Hz, 1H) 8.05 (d, J=9.61 Hz, 1H) 8.16 (s, 1H) 10.84 (br. s., 1H).

N-[3-(4-Amino-7-methyl-7H-pyrrolo[2,3-d]pyrimidin-5-yl)-2-fluoro-phenyl]-2-fluoro-4-methoxy-5-methyl-benzenesulfonamide, compound of formula (I), (cmpd 44)

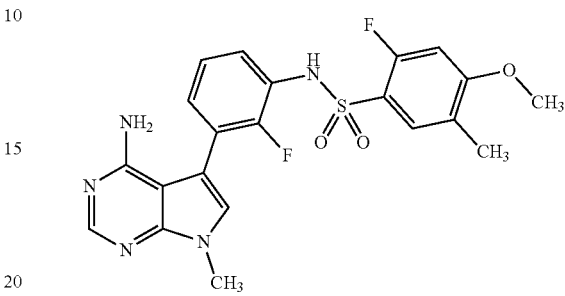

HPLC (254 nm): Rt: 5.52 min.

HRMS (ESI) calcd for C$_2$H$_{19}$F$_2$N$_5$O$_3$S [M+H]$^+$ 460.125, found 460.1243.

$^1$H NMR (500 MHz, DMSO-d6) delta ppm: 2.10 (s, 3H) 3.73 (s, 3H) 3.85 (s, 3H) 5.99 (br. s., 2H) 7.08 (d, J=12.35 Hz, 1H) 7.14-7.24 (m, 3H) 7.25 (s, 1H) 7.51 (d, J=8.08 Hz, 1H) 8.15 (s, 1H) 10.30 (s, 1H).

N-[3-(4-Amino-7-methyl-7H-pyrrolo[2,3-d]pyrimidin-5-yl)-2-fluoro-phenyl]-2,5-dichloro-benzenesulfonamide, compound of formula (I), (cmpd 45)

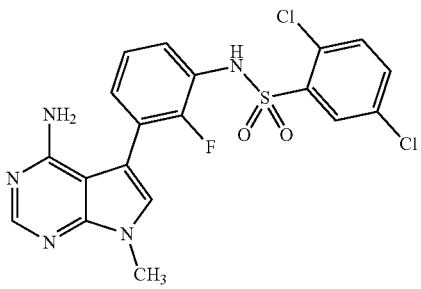 [SMILES: Cn1cc(-c2cccc(NS(=O)(=O)c3cc(Cl)ccc3Cl)c2F)c2c(N)ncnc21]

HPLC (254 nm): Rt: 5.67 min.

HRMS (ESI) calcd for C$_{19}$H$_{14}$Cl$_2$FN$_5$O$_2$S [M+H]$^+$ 466.0302, found 466.0294.

$^1$H NMR (401 MHz, DMSO-d6) delta ppm: 3.73 (s, 3H) 5.97 (br. s., 2H) 7.18-7.25 (m, 3H) 7.26 (s, 1H) 7.67-7.78 (m, 2H) 7.92 (dd, J=2.08, 0.85 Hz, 1H) 8.15 (s, 1H) 10.67 (br. s., 1H).

N-[3-(4-Amino-7-methyl-7H-pyrrolo[2,3-d]pyrimidin-5-yl)-2-fluoro-phenyl]-4-bromo-2,5-difluoro-benzenesulfonamide, compound of formula (I), (cmpd 46)

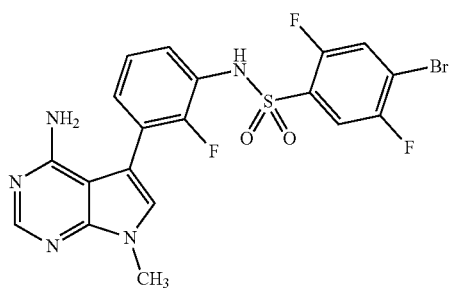 [SMILES: Cn1cc(-c2cccc(NS(=O)(=O)c3cc(F)c(Br)cc3F)c2F)c2c(N)ncnc21]

HPLC (254 nm): Rt: 5.65 min.

HRMS (ESI) calcd for $C_{19}H_{13}BrF_3N_5O_2S$ [M+H]$^+$ 511.9998, found 511.9978.

$^1$H NMR (401 MHz, DMSO-d6) delta ppm: 3.73 (s, 3H) 5.98 (br. s., 2H) 7.10-7.30 (m, 4H) 7.73 (dd, J=7.63, 6.04 Hz, 1H) 8.06 (dd, J=9.03, 5.37 Hz, 1H) 8.15 (s, 1H) 10.77 (br. s., 1H).

5-Chloro-thiophene-2-sulfonic acid [3-(4-amino-7-methyl-7H-pyrrolo[2,3-d]pyrimidin-5-yl)-2-fluoro-phenyl]-amide, compound of formula (I), (cmpd 47)

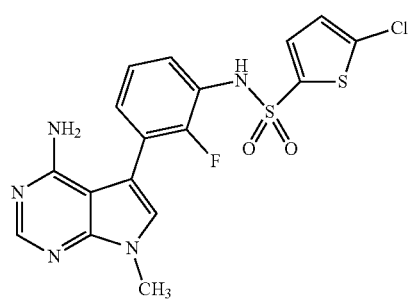 [SMILES: Cn1cc(-c2cccc(NS(=O)(=O)c3ccc(Cl)s3)c2F)c2c(N)ncnc21]

HPLC (254 nm): Rt: 5.46 min.

HRMS (ESI) calcd for $C_{17}H_{13}ClFN_5O_2S_2$ [M+H]$^+$ 438.0256, found 438.0244.

$^1$H NMR (401 MHz, DMSO-d6) delta ppm: 3.74 (s, 3H) 5.99 (br. s., 2H) 7.07-7.33 (m, 5H) 7.43 (d, J=4.03 Hz, 1H) 8.15 (s, 1H) 10.57 (br. s., 1H).

5-Bromo-thiophene-2-sulfonic acid [3-(4-amino-7-methyl-7H-pyrrolo[2,3-d]pyrimidin-5-yl)-2-fluoro-phenyl]-amide, compound of formula (I), (cmpd 48)

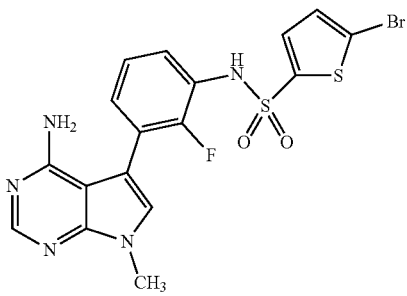 [SMILES: Cn1cc(-c2cccc(NS(=O)(=O)c3ccc(Br)s3)c2F)c2c(N)ncnc21]

HPLC (254 nm): Rt: 5.50 min.

HRMS (ESI) calcd for $C_{17}H_{13}BrFN_5O_2S_2$ [M+H]$^+$ 481.9751, found 481.9739.

$^1$H NMR (401 MHz, DMSO-d6) delta ppm: 3.74 (s, 3H) 5.99 (br. s., 2H) 7.25 (d, J=5.13 Hz, 4H) 7.31-7.36 (m, 1H) 7.36-7.41 (m, 1H) 8.15 (s, 1H) 10.56 (br. s., 1H).

N-[3-(4-Amino-7-methyl-7H-pyrrolo[2,3-d]pyrimidin-5-yl)-2-fluoro-phenyl]-3,5-bis-trifluoromethyl-benzenesulfonamide, compound of formula (I), (cmpd 49)

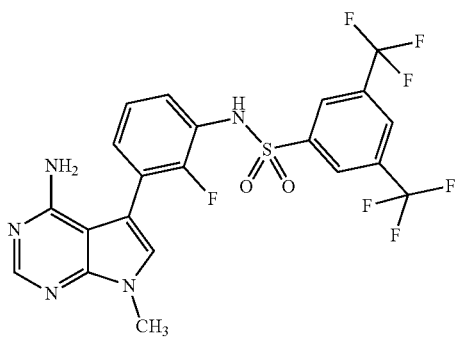 [SMILES: Cn1cc(-c2cccc(NS(=O)(=O)c3cc(C(F)(F)F)cc(C(F)(F)F)c3)c2F)c2c(N)ncnc21]

HPLC (254 nm): Rt: 6.17 min.

HRMS (ESI) calcd for $C_{21}H_{14}F_7N_5O_2S$ [M+H]$^+$ 534.0829, found 534.0824.

$^1$H NMR (401 MHz, DMSO-d6) delta ppm: 3.72 (s, 3H) 6.01 (br. s., 2H) 7.12-7.30 (m, 4H) 8.14 (s, 1H) 8.30 (s, 2H) 8.51 (s, 1H) 10.67 (br. s., 1H).

N-[3-(4-Amino-7-methyl-7H-pyrrolo[2,3-d]pyrimidin-5-yl)-2-fluoro-phenyl]-3-chloro-4-trifluoromethoxy-benzenesulfonamide, compound of formula (I), (cmpd 50)

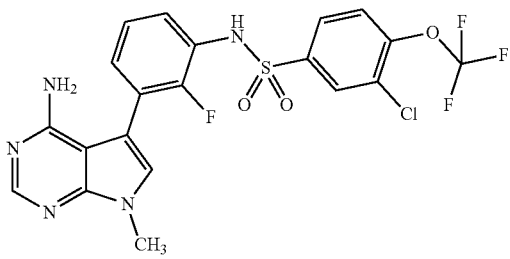 [SMILES: Cn1cc(-c2cccc(NS(=O)(=O)c3ccc(OC(F)(F)F)c(Cl)c3)c2F)c2c(N)ncnc21]

HPLC (254 nm): Rt: 6.14 min.
HRMS (ESI) calcd for $C_{20}H_{14}ClF_4N_5O_3S$ [M+H]$^+$ 516.0515, found 516.0507.
$^1$H NMR (401 MHz, DMSO-d6) delta ppm: 3.72 (s, 3H) 6.01 (br. s., 2H) 7.04-7.29 (m, 4H) 7.72-7.88 (m, 2H) 8.02 (d, J=2.07 Hz, 1H) 8.15 (s, 1H) 10.50 (br. s., 1H).

N-[3-(4-Amino-7-methyl-7H-pyrrolo[2,3-d]pyrimidin-5-yl)-2-fluoro-phenyl]-4-bromo-3-trifluoromethyl-benzenesulfonamide, compound of formula (I), (cmpd 51)

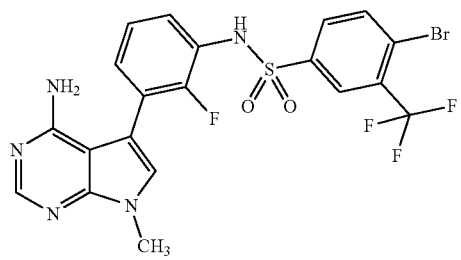 [SMILES: Cn1cc(-c2cccc(NS(=O)(=O)c3ccc(Br)c(C(F)(F)F)c3)c2F)c2c(N)ncnc21]

HPLC (254 nm): Rt: 6.03 min.
HRMS (ESI) calcd for $C_{20}H_{14}BrF_4N_5O_2S$ [M+H]$^+$ 544.0061, found 544.0071.
$^1$H NMR (401 MHz, DMSO-d6) delta ppm: 3.73 (s, 3H) 6.01 (br. s., 2H) 7.05-7.31 (m, 4H) 7.91 (dd, J=8.36, 2.26 Hz, 1H) 8.09 (d, J=2.20 Hz, 1H) 8.11-8.17 (m, 2H) 10.53 (br. s., 1H).

N-[3-(4-Amino-7-methyl-7H-pyrrolo[2,3-d]pyrimidin-5-yl)-2-fluoro-phenyl]-4-bromo-3-methyl-benzenesulfonamide, compound of formula (I), (cmpd 52)

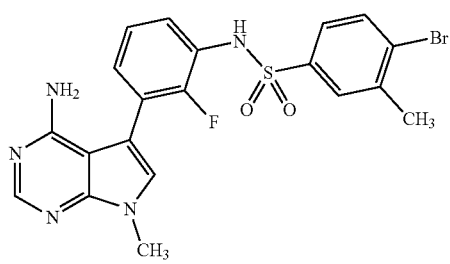 [SMILES: Cc1cc(S(=O)(=O)Nc2cccc(-c3cn(C)c4ncnc(N)c34)c2F)ccc1Br]

HPLC (254 nm): Rt: 5.83 min.
HRMS (ESI) calcd for $C_{20}H_{17}BrFN_5O_2S$ [M+H]$^+$ 490.0343, found 490.033.
$^1$H NMR (401 MHz, DMSO-d6) delta ppm: 2.39 (s, 3H) 3.73 (s, 3H) 5.98 (br. s., 2H) 6.97-7.34 (m, 4H) 7.41-7.59 (m, 1H) 7.74 (d, J=1.95 Hz, 1H) 7.81 (d, J=8.42 Hz, 1H) 8.15 (s, 1H) 10.29 (s, 1H).

N-[3-(4-Amino-7-methyl-7H-pyrrolo[2,3-d]pyrimidin-5-yl)-2-fluoro-phenyl]-3-fluoro-4-methoxy-benzenesulfonamide, compound of formula (I), (cmpd 53)

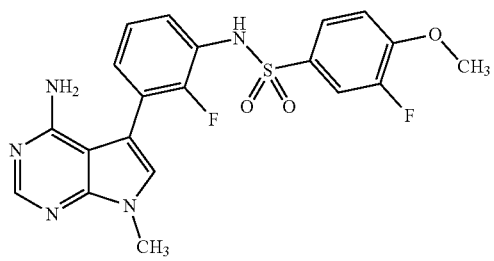

HPLC (254 nm): Rt: 5.19 min.
HRMS (ESI) calcd for $C_{20}H_{17}F_2N_5O_3S$ [M+H]$^+$ 446.1093, found 446.1084.
$^1$H NMR (401 MHz, DMSO-d6) delta ppm: 3.73 (s, 3H) 3.90 (s, 3H) 5.97 (br. s., 2H) 7.16-7.21 (m, 3H) 7.23 (s, 1H) 7.30-7.36 (m, 1H) 7.53-7.62 (m, 2H) 8.15 (s, 1H) 10.18 (s, 1H).

N-[3-(4-Amino-7-methyl-7H-pyrrolo[2,3-d]pyrimidin-5-yl)-2-fluoro-phenyl]-4-bromo-benzenesulfonamide, compound of formula (I), (cmpd 54)

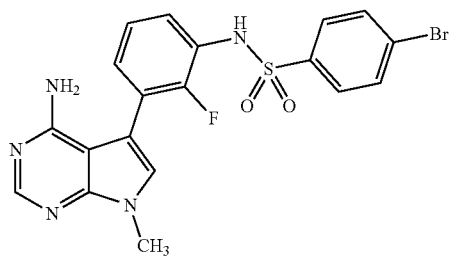 [SMILES: Cn1cc(-c2cccc(NS(=O)(=O)c3ccc(Br)cc3)c2F)c2c(N)ncnc21]

HPLC (254 nm): Rt: 7.95 min.
HRMS (ESI) calcd for $C_{19}H_{15}BrFN_5O_2S$ [M+H]$^+$ 476.0187, found 476.0184.
$^1$H NMR (500 MHz, DMSO-d6) delta ppm: 3.72 (s, 3H) 5.99 (br. s., 2H) 7.14-7.23 (m, 3H) 7.21 (s, 1H) 7.65-7.71 (m, 2H) 7.80 (d, J=8.69 Hz, 2H) 8.14 (s, 1H) 10.37 (br. s., 1H).

N-[3-(4-Amino-7-methyl-7H-pyrrolo[2,3-d]pyrimidin-5-yl)-2-fluoro-phenyl]-4-chloro-benzenesulfonamide, compound of formula (I), (cmpd 55)

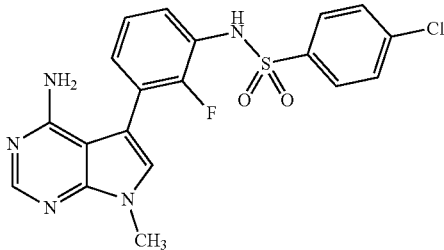

HPLC (254 nm): Rt: 7.70 min.
HRMS (ESI) calcd for $C_{19}H_{15}ClFN_5O_2S$ $[M+H]^+$ 432.0692, found 432.0701.
$^1$H NMR (500 MHz, DMSO-d6) delta ppm: 3.72 (s, 3H) 5.99 (br. s., 2H) 7.22 (s, 1H) 7.13-7.24 (m, 3H) 7.62-7.69 (m, 2H) 7.73-7.80 (m, 2H) 8.14 (s, 1H) 10.37 (br. s., 1H).

N-[3-(4-Amino-7-methyl-7H-pyrrolo[2,3-d]pyrimidin-5-yl)-2-fluoro-phenyl]-4-iodo-benzenesulfonamide, compound of formula (I), (cmpd 56)

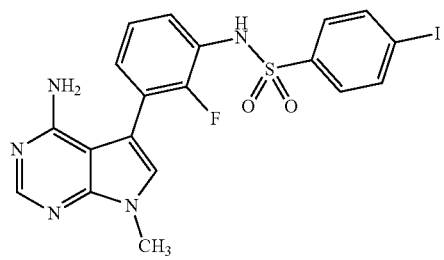 [SMILES: Cn1cc(-c2cccc(NS(=O)(=O)c3ccc(I)cc3)c2F)c2c(N)ncnc21]

HPLC (254 nm): Rt: 8.32 min.
HRMS (ESI) calcd for $C_{19}H_{15}FIN_5O_2S$ $[M+H]^+$ 524.0048, found 524.0042.
$^1$H NMR (500 MHz, DMSO-d6) delta ppm: 3.73 (s, 3H) 6.06 (br. s., 2H) 7.15-7.23 (m, 3H) 7.22 (s, 1H) 7.49-7.54 (m, 2H) 7.92-8.01 (m, 2H) 8.16 (s, 1H) 10.34 (s, 1H).

N-[3-(4-Amino-7-methyl-7H-pyrrolo[2,3-d]pyrimidin-5-yl)-2-fluoro-phenyl]-methanesulfonamide, compound of formula (I), (cmpd 68)

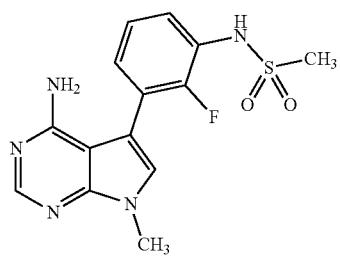 [SMILES: Cn1cc(-c2cccc(NS(C)(=O)=O)c2F)c2c(N)ncnc21]

HPLC (254 nm): Rt: 4.02 min.
HRMS (ESI) calcd for $C_{14}H_{14}FN_5O_2S$ $[M+H]^+$ 336.0925, found 336.0921.

$^1$H NMR (500 MHz, DMSO-d6) delta ppm: 3.05 (s, 3H) 3.75 (s, 3H) 6.07 (br. s., 2H) 7.17-7.23 (m, 1H) 7.25 (t, J=7.80 Hz, 1H) 7.34 (s, 1H) 7.37 (td, J=7.63, 1.83 Hz, 1H) 8.15 (s, 1H) 9.67 (br. s, 1H).

N-[3-(4-Amino-7-methyl-7H-pyrrolo[2,3-d]pyrimidin-5-yl)-2-methyl-phenyl]-5-chloro-2-fluoro-4-methoxy-benzenesulfonamide, compound of formula (I), (cmpd 57)

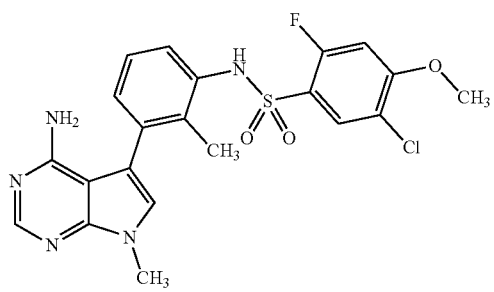 [SMILES: COc1cc(F)c(S(=O)(=O)Nc2cccc(-c3cn(C)c4ncnc(N)c34)c2C)cc1Cl]

HPLC (254 nm): Rt: 5.63 min.
HRMS (ESI) calcd for $C_{21}H_{19}ClFN_5O_3S$ $[M+H]^+$ 476.0954, found 476.095.
1H NMR (500 MHz, DMSO-d6) delta ppm: 2.03 (s, 3H) 3.72 (s, 3H) 3.95 (s, 3H) 5.06-6.53 (m, 2H) 6.99 (dd, J=7.85, 1.45 Hz, 1H) 7.09-7.18 (m, 2H) 7.19 (d, J=7.63 Hz, 1H) 7.37 (d, J=11.90 Hz, 1H) 7.66 (d, J=7.32 Hz, 1H) 8.13 (s, 1H) 10.00 (s, 1H).

N-[3-(4-Amino-7-methyl-7H-pyrrolo[2,3-d]pyrimidin-5-yl)-2-methyl-phenyl]-3-chloro-4-methoxy-benzenesulfonamide, compound of formula (I), (cmpd 58)

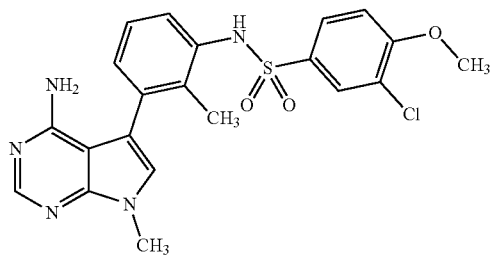 [SMILES: COc1ccc(S(=O)(=O)Nc2cccc(-c3cn(C)c4ncnc(N)c34)c2C)cc1Cl]

HPLC (254 nm): Rt: 5.50 min.
HRMS (ESI) calcd for $C_{21}H_{20}ClN_5O_3S$ $[M+H]^+$ 458.1048, found 458.105.
1H NMR (500 MHz, DMSO-d6) delta ppm: 1.95 (s, 3H) 3.72 (s, 3H) 3.93 (s, 3H) 5.08-6.41 (m, 2H) 6.91 (dd, J=7.85, 1.30 Hz, 1H) 7.03-7.15 (m, 2H) 7.17 (d, J=7.78 Hz, 1H) 7.31 (d, J=8.85 Hz, 1H) 7.57 (dd, J=8.69, 2.29 Hz, 1H) 7.70 (d, J=2.14 Hz, 1H) 8.12 (s, 1H) 9.67 (br. s., 1H).

Propane-1-sulfonic acid [3-(4-amino-7-methyl-7H-pyrrolo[2,3-d]pyrimidin-5-yl)-2-fluoro-phenyl]-amide, compound of formula (I) (cmpd 78)

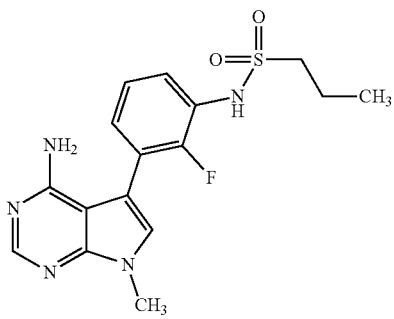 [SMILES: CCCS(=O)(=O)Nc1cccc(-c2cn(C)c3ncnc(N)c23)c1F]

HPLC (254 nm): Rt: 4.65 min.

HRMS (ESI) calcd for $C_{16}H_{18}FN_5O_2S$ [M+H]$^+$ 364.1238, found 364.1232.

1H NMR (500 MHz, DMSO-d6) delta ppm: 0.98 (t, J=7.47 Hz, 3H) 1.76 (sxt, J=7.53 Hz, 2H) 3.10-3.18 (m, 2H) 3.77 (s, 3H) 6.34 (br. s., 2H) 7.19-7.29 (m, 2H) 7.36-7.44 (m, 2H) 8.20 (s, 1H) 9.69 (s, 1H).

N-[3-(4-Amino-7-methyl-7H-pyrrolo[2,3-d]pyrimidin-5-yl)-2-fluoro-phenyl]-4-chloro-2-fluoro-5-methoxy-benzenesulfonamide, compound of formula (I) (cmpd 79)

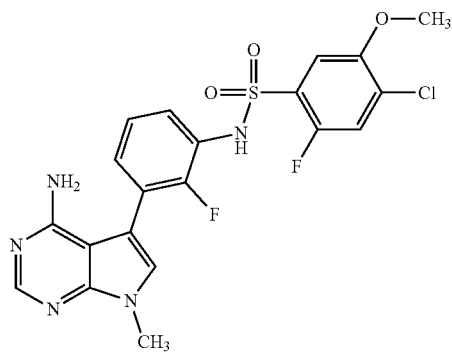 [SMILES: COc1cc(S(=O)(=O)Nc2cccc(-c3cn(C)c4ncnc(N)c34)c2F)c(F)cc1Cl]

HPLC (254 nm): Rt: 5.43 min.

HRMS (ESI) calcd for $C_{20}H_{16}ClF_2N_5O_3S$ [M+H]$^+$ 480.0703, found 480.07.

1H NMR (401 MHz, DMSO-d6) delta ppm: 3.73 (s, 3H) 3.83 (s, 3H) 5.65-6.18 (m, 2H) 7.07-7.21 (m, 1H) 7.23 (s, 1H) 7.36-7.43 (m, 1H) 8.14 (s, 1H).

5-Methyl-thiophene-2-sulfonic acid [3-(4-amino-7-methyl-7H-pyrrolo[2,3-d]pyrimidin-5-yl)-2-fluoro-phenyl]-amide, compound of formula (I) (cmpd 80)

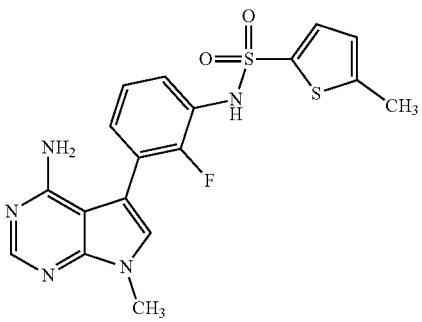 [SMILES: Cc1ccc(S(=O)(=O)Nc2cccc(-c3cn(C)c4ncnc(N)c34)c2F)s1]

HPLC (254 nm): Rt: 5.1 min.

HRMS (ESI) calcd for $C_{18}H_{16}FN_5O_2S_2$ [M+H]$^+$ 418.0802, found 418.0806.

1H NMR (500 MHz, DMSO-d6) delta ppm: 2.47 (d, J=0.76 Hz, 3H) 3.73 (s, 3H) 5.96 (br. s., 2H) 6.87 (dq, J=3.79, 1.02 Hz, 1H) 7.17-7.30 (m, 3H) 7.26 (s, 1H) 7.36 (d, J=3.81 Hz, 1H) 8.15 (s, 1H) 10.35 (s, 1H).

6-Methoxy-pyridine-3-sulfonic acid [3-(4-amino-7-methyl-7H-pyrrolo[2,3-d]pyrimidin-5-yl)-2-fluoro-phenyl]-amide, compound of formula (I) (cmpd 81)

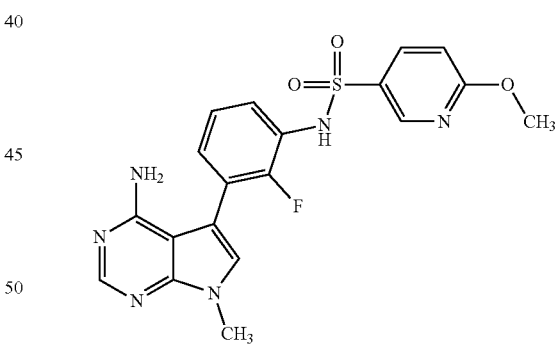

HPLC (254 nm): Rt: 4.84 min.

HRMS (ESI) calcd for $C_{19}H_{17}FN_6O_3S$ [M+H]$^+$ 429.114, found 429.1146.

1H NMR (500 MHz, DMSO-d6) delta ppm: 3.72 (s, 3H) 3.91 (s, 3H) 6.01 (br. s., 2H) 7.01 (dd, J=8.85, 0.61 Hz, 1H) 7.17-7.25 (m, 3H) 7.23 (s, 1H) 8.00 (dd, J=8.77, 2.67 Hz, 1H) 8.14 (s, 1H) 8.51 (dd, J=2.59, 0.61 Hz, 1H) 10.32 (s, 1H).

81

3-Methyl-3H-imidazole-4-sulfonic acid [3-(4-amino-7-methyl-7H-pyrrolo[2,3-d]pyrimidin-5-yl)-2-fluoro-phenyl]-amide, compound of formula (I) (cmpd 82)

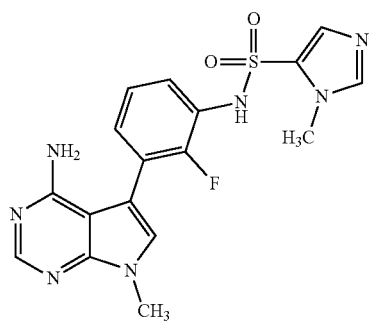 [SMILES: Cn1cncc1S(=O)(=O)Nc1cccc(-c2cn(C)c3ncnc(N)c23)c1F]

HPLC (254 nm): Rt: 3.78 min.

HRMS (ESI) calcd for $C_{17}H_{16}FN_7O_2S$ [M+H]$^+$ 402.1143, found 402.114.

1H NMR (500 MHz, DMSO-d6) delta ppm: 3.67 (s, 3H) 3.74 (s, 3H) 5.98 (br. s., 2H) 7.13-7.17 (m, 1H) 7.16-7.21 (m, 1H) 7.29 (s, 1H) 7.36 (td, J=7.44, 2.21 Hz, 1H) 7.77 (d, J=1.22 Hz, 1H) 7.80 (d, J=0.92 Hz, 1H) 8.15 (s, 1H) 10.05 (s, 1H).

Furan-2-sulfonic acid [3-(4-amino-7-methyl-7H-pyrrolo[2,3-d]pyrimidin-5-yl)-2-fluoro-phenyl]-amide, compound of formula (I) (cmpd 83)

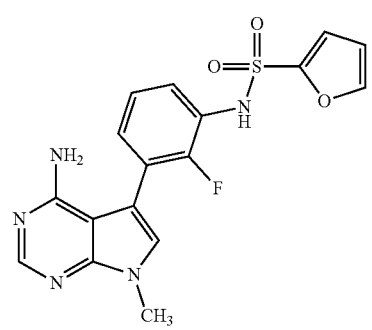 [SMILES: Cn1cc(-c2cccc(NS(=O)(=O)c3ccco3)c2F)c2c(N)ncnc21]

HPLC (254 nm): Rt: 5.22 min.

HRMS (ESI) calcd for $C_{17}H_{14}FN_5O_3S$ [M+H]$^+$ 388.0874, found 388.0884.

1H NMR (500 MHz, DMSO-d6) delta ppm: 3.74 (s, 3H) 5.98 (br. s., 2H) 6.66 (dd, J=3.43, 1.75 Hz, 1H) 7.09 (d, J=3.36 Hz, 1H) 7.18-7.27 (m, 3H) 7.28 (s, 1H) 8.00 (dd, J=1.68, 0.76 Hz, 1H) 8.15 (s, 1H) 10.58 (br. s., 1H).

82

N-[3-(4-Amino-7-methyl-7H-pyrrolo[2,3-d]pyrimidin-5-yl)-2-fluoro-phenyl]-benzenesulfonamide, compound of formula (I) (cmpd 84)

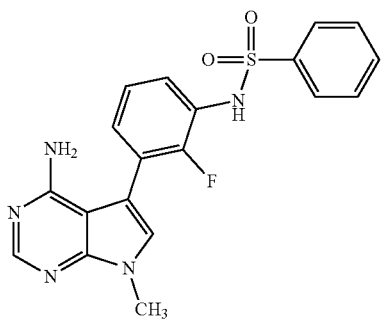 [SMILES: Cn1cc(-c2cccc(NS(=O)(=O)c3ccccc3)c2F)c2c(N)ncnc21]

HPLC (254 nm): Rt: 4.91 min.

HRMS (ESI) calcd for $C_{19}H_{16}FN_5O_2S$ [M+H]$^+$ 398.1082, found 398.1087.

1H NMR (500 MHz, DMSO-d6) delta ppm: 3.72 (s, 3H) 5.94 (br. s., 2H) 7.12-7.25 (m, 3H) 7.21 (s, 1H) 7.53-7.61 (m, 2H) 7.61-7.69 (m, 1H) 7.73-7.80 (m, 2H) 8.14 (s, 1H) 10.27 (s, 1H).

N-[3-(4-Amino-7-methyl-7H-pyrrolo[2,3-d]pyrimidin-5-yl)-2-fluoro-phenyl]-4-chloro-2-fluoro-benzenesulfonamide, compound of formula (I) (cmpd 85)

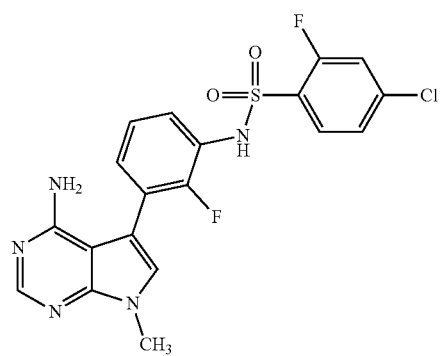 [SMILES: Cn1cc(-c2cccc(NS(=O)(=O)c3ccc(Cl)cc3F)c2F)c2c(N)ncnc21]

HPLC (254 nm): Rt: 5.47 min.

HRMS (ESI) calcd for $C_{19}H_{14}ClF_2N_5O_2S$ [M+H]$^+$ 450.0598, found 450.0593.

1H NMR (500 MHz, DMSO-d6) delta ppm: 3.73 (s, 3H) 5.99 (br. s., 2H) 7.19-7.28 (m, 4H) 7.46 (dd, J=8.54, 1.83 Hz, 1H) 7.73-7.81 (m, 2H) 8.15 (s, 1H) 10.67 (br. s., 1H).

N-[3-(4-Amino-7-methyl-7H-pyrrolo[2,3-d]pyrimidin-5-yl)-2-fluoro-phenyl]-3-cyano-4-methoxy-benzenesulfonamide, compound of formula (I) (cmpd 86)

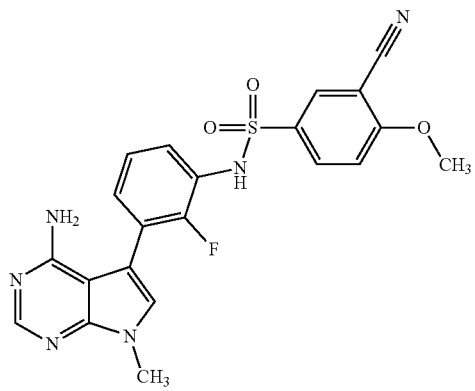 [SMILES: COc1ccc(S(=O)(=O)Nc2cccc(-c3cn(C)c4ncnc(N)c34)c2F)cc1C#N]

HPLC (254 nm): Rt: 5.01 min.

HRMS (ESI) calcd for $C_{21}H_{17}FN_6O_3S$ [M+H]$^+$ 453.114, found 453.1136.

1H NMR (500 MHz, DMSO-d6) delta ppm: 3.73 (s, 3H) 3.99 (s, 3H) 6.03 (br. s., 2H) 7.13-7.23 (m, 3H) 7.24 (s, 1H) 7.43 (d, J=9.15 Hz, 1H) 8.01 (dd, J=9.00, 2.29 Hz, 1H) 8.10 (d, J=2.44 Hz, 1H) 8.15 (s, 1H) 10.30 (s, 1H).

N-[3-(4-Amino-7-methyl-7H-pyrrolo[2,3-d]pyrimidin-5-yl)-2-fluoro-phenyl]-3-bromo-4-methoxy-benzenesulfonamide, compound of formula (I) (cmpd 87)

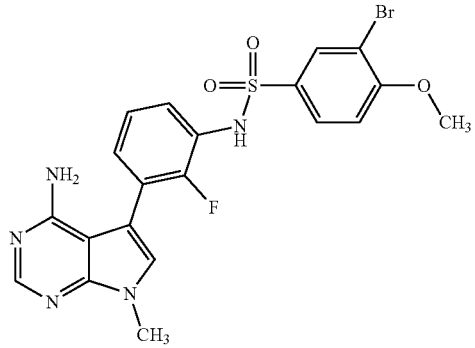 [SMILES: COc1ccc(S(=O)(=O)Nc2cccc(-c3cn(C)c4ncnc(N)c34)c2F)cc1Br]

HPLC (254 nm): Rt: 5.47 min.

HRMS (ESI) calcd for $C_{20}H_{17}BrFN_5O_3S$ [M+H]$^+$ 506.0292, found 506.0297.

1H NMR (500 MHz, DMSO-d6) delta ppm: 3.73 (s, 3H) 3.91 (s, 3H) 6.01 (br. s., 2H) 7.14-7.22 (m, 3H) 7.23 (s, 1H) 7.27 (d, J=8.85 Hz, 1H) 7.73 (dd, J=8.69, 2.29 Hz, 1H) 7.91 (d, J=2.29 Hz, 1H) 8.15 (s, 1H) 10.21 (s, 1H).

For the following compounds, pyridine was used as solvent:

Cyclopropanesulfonic acid [3-(4-amino-7-methyl-7H-pyrrolo[2,3-d]pyrimidin-5-yl)-2-fluoro-phenyl]-amide, compound of formula (I) (cmpd 88)

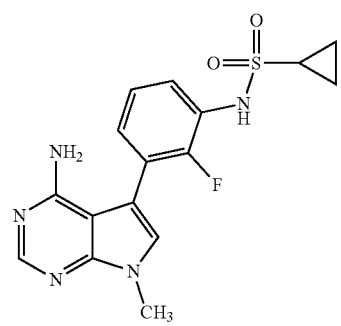 [SMILES: Cn1cc(-c2cccc(NS(=O)(=O)C3CC3)c2F)c2c(N)ncnc21]

HPLC (254 nm): Rt: 4.43 min.

HRMS (ESI) calcd for $C_{16}H_{16}FN_5O_2S$ [M+H]$^+$ 362.1082, found 362.1079.

1H NMR (500 MHz, DMSO-d6) delta ppm: 0.86-0.94 (m, 2H) 0.93-1.01 (m, 2H) 2.67-2.75 (m, 1H) 3.75 (s, 3H) 6.05 (br. s., 2H) 7.21-7.30 (m, 2H) 7.35 (s, 1H) 7.37-7.44 (m, 1H) 8.15 (s, 1H) 9.67 (s, 1H).

Cyclohexanesulfonic acid [3-(4-amino-7-methyl-7H-pyrrolo[2,3-d]pyrimidin-5-yl)-2-fluoro-phenyl]-amide, compound of formula (I) (cmpd 89)

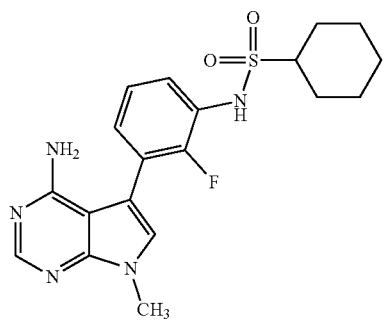 [SMILES: Cn1cc(-c2cccc(NS(=O)(=O)C3CCCCC3)c2F)c2c(N)ncnc21]

HPLC (254 nm): Rt: 5.3 min.

HRMS (ESI) calcd for $C_{19}H_{22}FN_5O_2S$ [M+H]$^+$ 404.1551, found 404.1548.

1H NMR (500 MHz, DMSO-d6) delta ppm: 1.14 (tt, J=12.80, 3.00 Hz, 1H) 1.26 (qt, J=12.70, 3.15 Hz, 2H) 1.42 (qd, J=12.38, 3.13 Hz, 2H) 1.61 (d, J=12.20 Hz, 1H) 1.78 (dt, J=12.96, 3.13 Hz, 2H) 2.11 (d, J=10.83 Hz, 2H) 3.06 (tt, J=11.71, 3.09 Hz, 1H) 3.75 (s, 3H) 6.06 (br. s., 2H) 7.18-7.23 (m, 1H) 7.22-7.26 (m, 1H) 7.33 (s, 1H) 7.41 (td, J=7.51, 2.21 Hz, 1H) 8.15 (s, 1H) 9.64 (s, 1H).

N-[3-(4-Amino-thieno[3,2-c]pyridin-3-yl)-2-fluoro-phenyl]-5-chloro-2-fluoro-4-methoxy-benzenesulfonamide, compound of formula (I), (cmpd 59)

Scheme 1

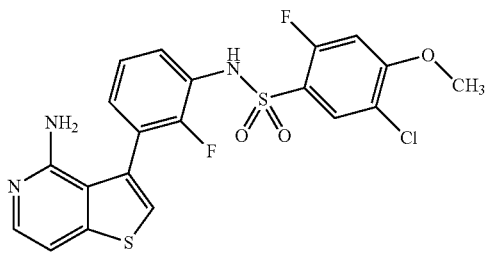

3-(3-Amino-2-fluoro-phenyl)-thieno[3,2-c]pyridin-4-ylamine, compound of formula (VII)

Scheme 1, Step b

To a solution of 3-bromo-thieno[3,2-c]pyridin-4-ylamine (80 mg, 0.35 mmol) in DME (3.2 mL) and water (0.32 mL), Cs$_2$CO$_3$ (342 mg, 1.05 mmol) and 2-fluoro-3-(4,4,5,5-tetramethyl-[1,3,2]dioxaborolan-2-yl)-phenylamine (207 mg, 0.87 mmol) were added. The mixture was sonicated for 5 minutes before adding Pd(dppf)Cl$_2$ (20 mg) and microwave heating at 100° C. for 1.5 h. The mixture was diluted with AcOEt and washed with a saturated solution of NaHCO$_3$ and brine. The organic layer was dried with Na$_2$SO$_4$ and evaporated to dryness. The residue was purified by flash column chromatography over silica gel eluting with DCM-MeOH 2%. 3-(3-amino-2-fluoro-phenyl)-thieno[3,2-c]pyridin-4-ylamine was so isolated (68 mg).

HPLC (254 nm): Rt: 4.55 min.

HRMS (ESI) calcd for C$_{13}$H$_{11}$FN$_3$S [M+H]$^+$ 260.0652, found 260.0654.

1H NMR (500 MHz, DMSO-d6) delta ppm 5.38 (s, 4H) 6.52 (ddd, J=7.44, 6.37, 1.45 Hz, 1H) 6.88 (td, J=8.27, 1.60 Hz, 1H) 6.99 (t, J=7.70 Hz, 1H) 7.26 (d, J=5.64 Hz, 1H) 7.51 (s, 1H) 7.81 (d, J=5.64 Hz, 1H).

N-[3-(4-Amino-thieno[3,2-c]pyridin-3-yl)-2-fluoro-phenyl]-5-chloro-2-fluoro-4-methoxy-benzenesulfonamide, compound of formula (I) (cmpd 59)

Scheme 1, Step f

To a solution of 3-(3-amino-2-fluoro-phenyl)-thieno[3,2-c]pyridin-4-ylamine (40 mg, 0.15 mmol) in DCM (2.5 mL), pyridine (15 microL) and 5-chloro-2-fluoro-4-methoxy sulfonyl chloride (50 mg, 0.19 mmol) were added. The mixture was stirred at room temperature for 1 day and then at reflux for 15 hours. After diluting with DCM, the solution was washed with a saturated solution of NaHCO$_3$ and water. The organic layer was then dried with Na$_2$SO$_4$ and evaporated to dryness. The residue was purified by flash column chromatography over silica gel eluting with a gradient of 1:1-4:6 hexane/AcOEt, yielding the title compound (12.3 mg).

HPLC (254 nm): Rt: 6.20 min.

HRMS (ESI) calcd for C$_{20}$H$_{15}$ClF$_2$N$_3$O$_3$S$_2$ [M+H]$^+$ 482.0206, found 482.0202.

1H NMR (500 MHz, DMSO-d6) delta ppm 3.93 (s, 3H) 5.15-5.32 (m, 2H) 7.23-7.33 (m, 3H) 7.38 (d, J=11.90 Hz, 1H) 7.39-7.44 (m, 1H) 7.52 (s, 1H) 7.73 (d, J=7.32 Hz, 1H) 7.83 (d, J=5.64 Hz, 1H) 10.67 (br. s., 1H)

Analogously the following compound was obtained:

N-[3-(4-Amino-thieno[3,2-c]pyridin-3-yl)-2-fluoro-phenyl]-4-methoxy-3-methyl-benzenesulfonamide, compound of formula (I), (cmpd 60)

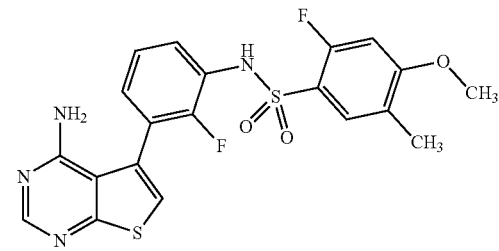 [SMILES: COc1cc(F)c(S(=O)(=O)Nc2cccc(-c3csc4ncnc(N)c34)c2F)cc1C]

HPLC (254 nm): Rt: 6.15 min.

HRMS (ESI) calcd for C$_{21}$H$_{19}$FN$_3$O$_3$S$_2$ [M+H]$^+$ 444.0847, found 444.0847.

1H NMR (500 MHz, DMSO-d6) delta ppm 2.19 (s, 3H) 3.87 (s, 3H) 5.22 (br. s., 2H) 7.12 (d, J=8.39 Hz, 1H) 7.22-7.30 (m, 2H) 7.32 (d, J=5.64 Hz, 1H) 7.41 (td, J=7.32, 2.59 Hz, 1H) 7.53 (s, 1H) 7.57-7.61 (m, 2H) 7.86 (d, J=5.64 Hz, 1H) 10.19 (br. s., 1H).

EXAMPLE 5

N-{3-[4-Amino-1-(1-methyl-piperidin-4-yl)-1H-pyrazolo[3,4-d]pyrimidin-3-yl]-2-fluoro-phenyl}-5-chloro-2-fluoro-4-methoxy-benzenesulfonamide, compound of formula (I), (cmpd 61)

Scheme 1

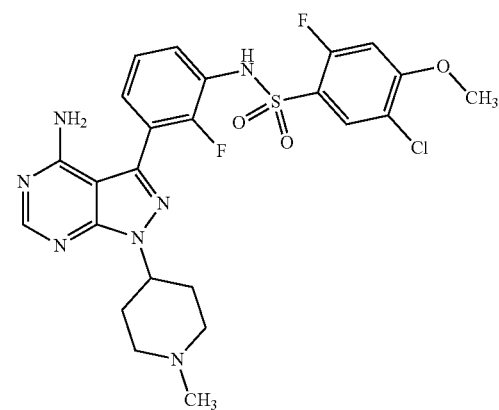 [SMILES: COc1cc(F)c(S(=O)(=O)Nc2cccc(-c3nn(C4CCN(C)CC4)c4ncnc(N)c34)c2F)cc1Cl]

N-[3-(4-Amino-1-piperidin-4-yl-1H-pyrazolo[3,4-d]pyrimidin-3-yl)-2-fluoro-phenyl]-5-chloro-2-fluoro-4-methoxy-benzenesulfonamide, compound of formula (I), (cmpd 62)

Scheme 1

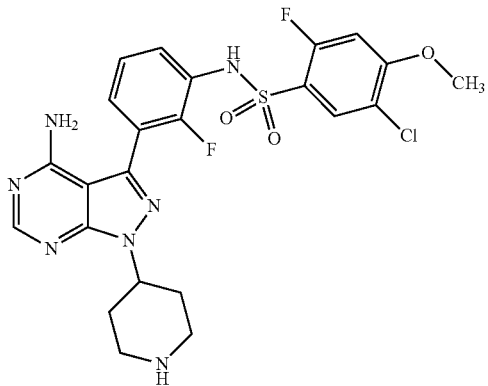

To 4-{4-amino-3-[3-(5-chloro-2-fluoro-4-methoxy-benzenesulfonylamino)-2-fluoro-phenyl]-pyrazolo[3,4-d]pyrimidin-1-yl}-piperidine-1-carboxylic acid tert-butyl ester (155 mg, 0.239 mmol) in dioxane (4 mL) was added HCl in dioxane 4M (4 mL, 16 mmol) and stirred at room temperature overnight. The organic was removed under vacuum and the residue taken up with water and treated with aqueous NaOH 2N until pH of the solution was >9. The resulting solid was filtered and triturated with Et$_2$O to furnish the title compound (100 mg) as white solid.

HPLC (254 nm): Rt: 4.64 min.
HRMS (ESI) calcd for C$_{23}$H$_{22}$ClF$_2$N$_7$O$_3$S [M+H]$^+$ 550.1234, found 550.1238.
1H NMR (401 MHz, DMSO-d6) delta ppm: 1.92 (m, J=10.74 Hz, 2H) 2.03-2.24 (m, 2H) 2.80 (td, J=12.42, 1.65 Hz, 2H) 3.18 (m, J=12.57 Hz, 2H) 3.86 (s, 3H) 4.81 (tt, J=11.52, 4.23 Hz, 1H) 6.62 (td, J=6.87, 1.53 Hz, 1H) 6.88 (t, J=7.69 Hz, 1H) 7.05 (d, J=11.35 Hz, 1H) 7.18 (td, J=8.27, 1.65 Hz, 1H) 7.68-7.72 (m, 1H) 8.21 (s, 1H).

Analogously the following compounds were obtained:

N-[3-(4-Amino-1-piperidin-4-yl-1H-pyrazolo[3,4-d]pyrimidin-3-yl)-2-fluoro-phenyl]-3-chloro-4-methoxy-benzenesulfonamide, compound of formula (II), (cmpd 63)

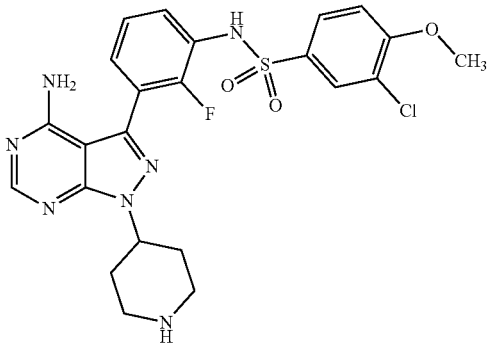 [SMILES: COc1ccc(S(=O)(=O)Nc2cccc(-c3nn(C4CCNCC4)c4ncnc(N)c34)c2F)cc1Cl]

HPLC (254 nm): Rt: 4.57 min.

HRMS (ESI) calcd for C$_{23}$H$_{23}$ClFN$_7$O$_3$S [M+H]$^+$ 532.1329, found 532.1341.
1H NMR (401 MHz, DMSO-d6) delta ppm: 1.97-2.07 (m, 2H) 2.12-2.29 (m, 2H) 3.01 (td, J=12.76, 2.56 Hz, 2H) 3.88 (s, 3H) 4.94 (tt, J=11.31, 4.32 Hz, 1H) 6.81 (t, J=6.77 Hz, 1H) 6.98 (t, J=7.81 Hz, 1H) 7.18 (d, J=8.67 Hz, 1H) 7.21-7.27 (m, 1H) 7.67 (dd, J=8.54, 2.20 Hz, 1H) 7.69-7.72 (m, 1H) 8.22-8.24 (m, 1H).

N-[3-(4-Amino-7-piperidin-4-yl-7H-pyrrolo[2,3-d]pyrimidin-5-yl)-2-fluoro-phenyl]-4-methoxy-3-methyl-benzenesulfonamide, compound of formula (I), (cmpd 64)

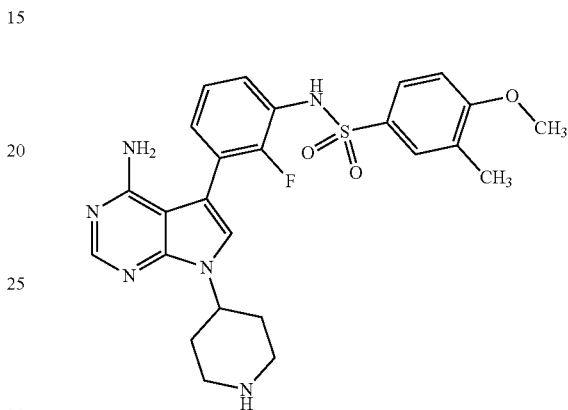

HPLC (254 nm): Rt: 4.79 min.
HRMS (ESI) calcd for C$_{25}$H$_{27}$FN$_6$O$_3$S [M+H]$^+$ 511.1922, found 511.1918.
1H NMR (500 MHz, DMSO-d6) delta ppm: 2.11-2.18 (m, 5H) 2.23-2.34 (m, 2H) 3.06-3.21 (m, 2H) 3.85 (s, 3H) 4.91-5.01 (m, 1H) 7.09 (d, J=8.69 Hz, 1H) 7.17-7.28 (m, 4H) 7.55 (s, 2H) 7.60 (d, J=1.83 Hz, 1H) 7.65 (dd, J=8.62, 2.36 Hz, 1H) 8.45 (s, 1H) 8.78 (m, J=9.46 Hz, 1H) 8.99 (d, J=9.91 Hz, 1H) 10.12 (s, 1H).

N-{3-[4-Amino-1-(1-methyl-piperidin-4-yl)-1H-pyrazolo[3,4-d]pyrimidin-3-yl]-2-fluoro-phenyl}-5-chloro-2-fluoro-4-methoxy-benzenesulfonamide, compound of formula (I) (cmpd 61)

Scheme 1
To N-[3-(4-amino-1-piperidin-4-yl-1H-pyrazolo[3,4-d]pyrimidin-3-yl)-2-fluoro-phenyl]-5-chloro-2-fluoro-4-methoxy-benzenesulfonamide (26 mg, 0.047 mmol) in DCM (2 mL) was added formaldehyde solution in water 37% (21 microL, 0.280 mmol), AcOH (3 microL, 0.052 mmol) and stirred 10 min at room temperature. Then NaBH(OAc)$_3$ (66 mg, 0.302 mmol) was added and the mixture was stirred at room temperature for 5 h. The reaction was diluted with DCM and treated with saturated aqueous NaHCO3. The aqueous layer was extracted with DCM and the combined organic phase washed with brine, dried over Na$_2$SO$_4$ and evaporated. The crude was purified by silica gel chromatography which was eluted with DCM:MeOH:NH$_3$=95:5:0.5% to furnish the title compound (17 mg) as white solid.
HPLC (254 nm): Rt: 4.75 min.
HRMS (ESI) calcd for C$_{24}$H$_{24}$ClF$_2$N$_7$O$_3$S [M+H]$^+$ 564.1391, found 564.1385.
1H NMR (401 MHz, DMSO-d6) delta ppm: 1.98 (m, J=10.86 Hz, 2H) 2.14-2.31 (m, 2H) 2.34-2.48 (m, 5H) 3.10

(m, J=10.86 Hz, 2H) 3.91 (s, 3H) 4.74 (m, J=11.11, 11.11 Hz, 1H) 4.70-4.70 (m, 0H) 7.18 (d, J=6.47 Hz, 2H) 7.22-7.38 (m, 2H) 7.73 (d, J=7.45 Hz, 1H) 8.23 (s, 1H) 9.37-10.81 (m, 1H).

Analogously the following compounds were obtained:

N-{3-[4-Amino-1-(1-isopropyl-piperidin-4-yl)-1H-pyrazolo[3,4-d]pyrimidin-3-yl]-2-fluoro-phenyl}-5-chloro-2-fluoro-4-methoxy-benzenesulfonamide, compound of formula (I), (cmpd 65)

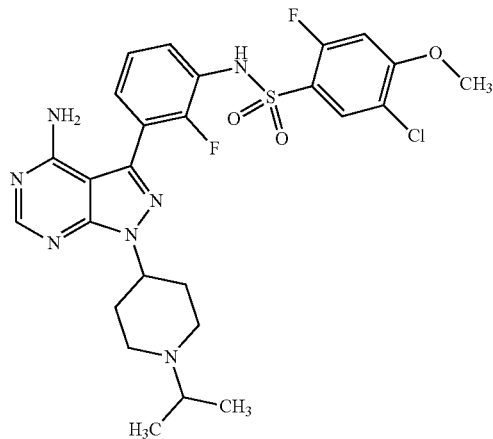 [SMILES: COc1cc(F)c(S(=O)(=O)Nc2cccc(-c3nn(C4CCN(C(C)C)CC4)c4ncnc(N)c34)c2F)cc1Cl]

HPLC (254 nm): Rt: 4.99 min.
HRMS (ESI) calcd for $C_{26}H_{28}ClF_2N_7O_3S$ [M+H]$^+$ 592.1704, found 592.1702.
1H NMR (401 MHz, DMSO-d6) delta ppm: 1.09-1.19 (m, 6H) 2.07 (br. s., 2H) 2.27 (m, J=9.89 Hz, 2H) 2.70-3.25 (m, 5H) 3.91 (s, 3H) 4.84 (br. s., 1H) 7.15 (br. s., 2H) 7.20-7.35 (m, 2H) 7.73 (d, J=7.45 Hz, 1H) 8.13-8.33 (m, 1H).

N-{3-[4-Amino-1-(1-methyl-piperidin-4-yl)-1H-pyrazolo[3,4-d]pyrimidin-3-yl]-2-fluoro-phenyl}-3-chloro-4-methoxy-benzenesulfonamide, compound of formula (I), (cmpd 66)

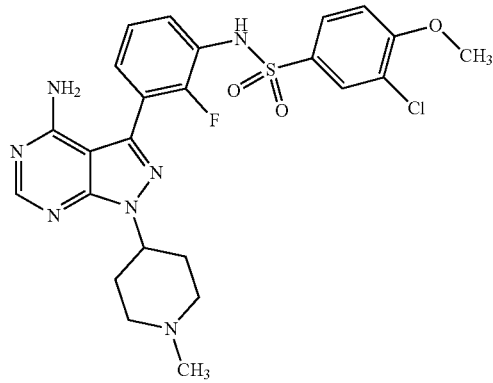 [SMILES: COc1ccc(S(=O)(=O)Nc2cccc(-c3nn(C4CCN(C)CC4)c4ncnc(N)c34)c2F)cc1Cl]

HPLC (254 nm): Rt: 4.61 min.
HRMS (ESI) calcd for $C_{24}H_{25}ClFN_7O_3S$ [M+H]$^+$ 546.1485, found 546.1485.
1H NMR (500 MHz, DMSO-d6) delta ppm: 1.93 (m, J=10.98 Hz, 2H) 2.12-2.24 (m, 2H) 2.26-2.42 (m, 5H) 3.02 (m, J=9.00 Hz, 2H) 3.91 (s, 3H) 4.59-4.79 (m, 1H) 7.07-7.36 (m, 4H) 7.71 (dd, J=8.77, 2.21 Hz, 1H) 7.79 (d, J=2.29 Hz, 1H) 8.22 (s, 1H) 9.58-10.49 (m, 1H).

EXAMPLE 6

N-[3-(4-Amino-7-methyl-7H-pyrrolo[2,3-d]pyrimidin-5-yl)-2-cyano-phenyl]-5-chloro-2-fluoro-4-methoxy-benzenesulfonamide, compound of formula (I), (cmpd 90)

Scheme 2

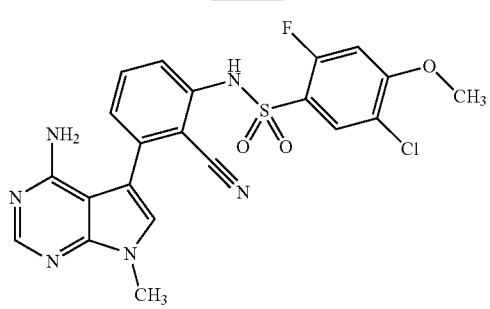

5-Chloro-N-[3-(4-chloro-7-methyl-7H-pyrrolo[2,3-d]pyrimidin-5-yl)-2-cyano-phenyl]-2-fluoro-4-methoxy-benzenesulfonamide, compound of formula (XIV)

Scheme 2, Step c3

In a Schlenk tube, to 4-chloro-7-methyl-5-(4,4,5,5-tetramethyl-[1,3,2]dioxaborolan-2-yl)-7H-pyrrolo[2,3-d]pyrimidine (118 mg, 0.403 mmol), N-(3-bromo-2-cyano-phenyl)-5-chloro-2-fluoro-4-methoxy-benzenesulfonamide (85 mg, 0.202 mmol), $Cs_2CO_3$ (217 mg, 0.666 mmol) and 1,1'-bis(diphenylphosphino)ferrocene]dichloropalladium (II), complex with dichloromethane (1:1) (17 mg, 0.020 mmol) were added DMF (5 mL). The reaction mixture was degassed with nitrogen, heated to 100° C. overnight and then filtered through a celite pad. The filtrate was evaporated under reduced pressure; the crude was taken up with DCM, washed with saturated aqueous $NaHCO_3$, brine and dried over $Na_2SO_4$. The organic was evaporated and the crude purified by silica gel chromatography which was eluted with AcOEt:hexane=7:3 to furnish the title compound (40 mg) as white solid.

HPLC (254 nm): Rt: 5.55 min.
HRMS (ESI) calcd for $C_{21}H_{14}Cl_2FN_5O_3S$ [M+H]$^+$ 506.0251, found 506.0251.
$^1$H NMR (500 MHz, DMSO-d6) delta ppm: 3.92 (s, 3H) 3.95 (s, 3H) 7.22-7.35 (m, 1H) 7.38 (d, J=11.90 Hz, 1H) 7.44-7.54 (m, 1H) 7.63 (d, J=7.32 Hz, 1H) 7.70 (t, J=7.85 Hz, 1H) 7.96 (s, 1H) 8.72 (s, 1H) 11.00 (br. s., 1H).

N-[3-(4-Amino-7-methyl-7H-pyrrolo[2,3-d]pyrimidin-5-yl)-2-cyano-phenyl]-5-chloro-2-fluoro-4-methoxy-benzenesulfonamide, compound of formula (I), (cmpd 90)

Scheme 2, Step h1

To a 5 mL microwave vial charged with dioxane (0.5 mL) was added 5-chloro-N-[3-(4-chloro-7-methyl-7H-pyrrolo[2,3-d]pyrimidin-5-yl)-2-cyano-phenyl]-2-fluoro-4-methoxybenzenesulfonamide (21 mg, 0.041 mmol), ammonium hydroxide (2.5 mL, 19.11 mmol) and sealed. The reaction vessel was heated under microwave irradiation for 180 min at 130° C. The mixture was diluted with water and extracted with DCM. The combined organic phase was washed with brine, dried over $Na_2SO_4$ and evaporated. The solid obtained was triturated with $Et_2O$ to afford the title compound (6.8 mg) as white solid.

HPLC (254 nm): Rt: 4.79 min.

HRMS (ESI) calcd for $C_{21}H_{16}ClFN_5O_3S$ $[M+H]^+$ 487.075, found 487.0754.

$^1$H NMR (500 MHz, DMSO-d6) delta ppm: 3.74 (s, 3H) 3.87 (s, 3H) 4.93-6.30 (m, 1H) 6.51 (d, J=6.86 Hz, 1H) 7.08-7.16 (m, 1H) 7.16-7.23 (m, 1H) 7.31 (s, 1H) 7.74 (d, J=7.32 Hz, 1H) 8.14 (s, 1H).

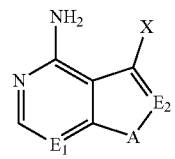

(II)

wherein E1 and E2 are independently CH or N;

A is O, S or NR5, wherein

R5 is hydrogen or an optionally substituted group selected from straight or branched (C1-C8) alkyl, (C2-C8) alkenyl, (C2-C8) alkynyl, (C3-C8) cycloalkyl, (C3-C8) cycloalkenyl, heterocyclyl, aryl and heteroaryl; and

---

---

The invention claimed is:

1. A process for preparing a compound of formula (I)

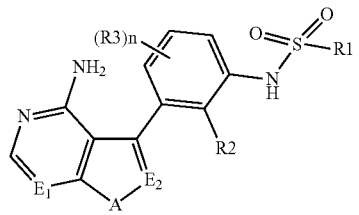

(I)

wherein n is 0, 1 or 2;

R1 is an optionally substituted group selected from straight or branched (C1-C8) alkyl, (C2-C8) alkenyl, (C2-C8) alkynyl, (C3-C8) cycloalkyl, (C3-C8) cycloalkenyl, heterocyclyl, aryl and heteroaryl;

R2 and R3 are independently halogen, cyano, OR4 or an optionally substituted group selected from straight or branched (C1-C8) alkyl, (C2-C8) alkenyl, (C2-C8) alkynyl and (C3-C8) cycloalkyl, wherein R4 is an optionally substituted group selected from straight or branched (C1-C8) alkyl, (C2-C8) alkenyl, (C2-C8) alkynyl and (C3-C8) cycloalkyl;

E1 and E2 are independently CH or N;

A is O, S or NR5, wherein

R5 is hydrogen or an optionally substituted group selected from straight or branched (C1-C8) alkyl, (C2-C8) alkenyl, (C2-C8) alkynyl, (C3-C8) cycloalkyl, (C3-C8) cycloalkenyl, heterocyclyl, aryl and heteroaryl;

or a pharmaceutically acceptable salt thereof, which comprises the step of cross-coupling of an intermediate of formula (II)

X is halogen or a leaving group, alternatively with the following compounds:

Step a) a derivative of formula (IV)

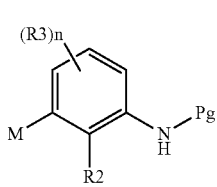

(IV)

wherein R2 and R3 are independently halogen, cyano, OR4 or an optionally substituted group selected from straight or branched (C1-C8) alkyl, (C2-C8) alkenyl, (C2-C8) alkynyl and (C3-C8) cycloalkyl, wherein R4 is an optionally substituted group selected from straight or branched (C1-C8) alkyl, (C2-C8) alkenyl, (C2-C8) alkynyl and (C3-C8) cycloalkyl;

n is 0, 1 or 2;

M is an organometal group and Pg is a nitrogen protecting group; followed by

Step e) selective removing of the Pg group from the resultant intermediate of formula (V)

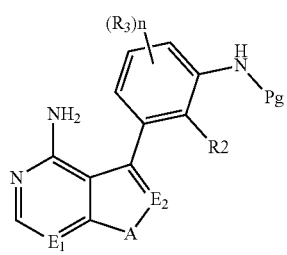

(V)

wherein E1, E2, A, R2, R3, n and Pg are as defined above; and

Step f) reacting the resultant intermediate of formula (VII)

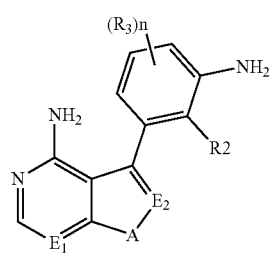

(VII)

wherein E1, E2, A, R2, R3 and n are as defined above, with a derivative of formula (XI)

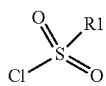

(XI)

wherein R1 is as defined above, to obtain a compound of formula (I)

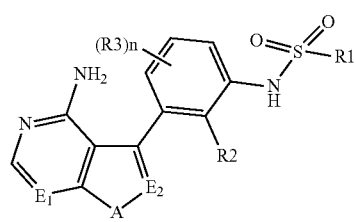

(I)

as defined above;
OR:
Step b) a derivative of formula (VI)

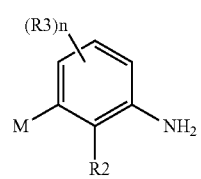

(VI)

wherein R2, R3, n and M are as defined above; followed by

Step f) reacting the resultant intermediate of formula (VII), as defined above, with a derivative of formula (XI), as defined above, to obtain a compound of formula (I)

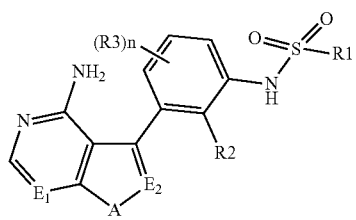

(I)

as defined above;
OR:
Step c) a derivative of formula (VIII)

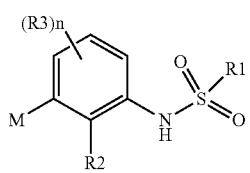

(VIII)

wherein R1, R2, R3, n and M are as defined above;
OR:
Step d) a derivative of formula (IX)

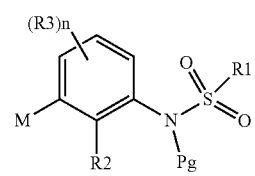

(IX)

wherein R1, R2, R3, n, Pg and M are as defined above; followed by:

Step g) selective removing of the Pg group from the resultant intermediate of formula (X)

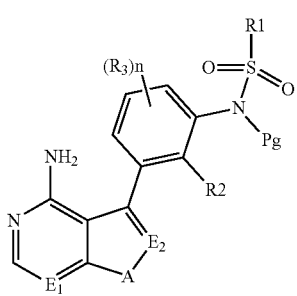

(X)

wherein E1, E2, A, R1, R2, R3, n and Pg are as defined above, to obtain a compound of formula (I)
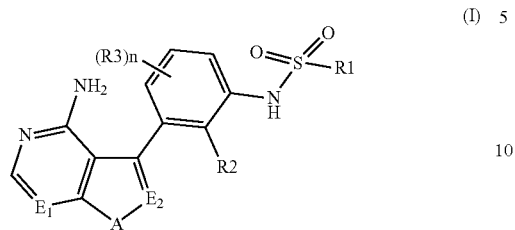
(I)
as defined in claim above;
optionally converting said compound of formula (I) into another compound of formula (I), converting said compound of formula (I) into a pharmaceutically acceptable salt thereof, or converting said salt into a free compound (I).
* * * * *